(12) United States Patent
Dai et al.

(10) Patent No.: US 8,729,257 B2
(45) Date of Patent: May 20, 2014

(54) HYBRID LIPID COMPOUNDS BASED ON PENTAERYTHRITOL, INTERMEDIATES, PREPARATION METHODS AND USE THEREOF

(75) Inventors: Zhifei Dai, Harbin (CN); Xiaolong Liang, Harbin (CN); Xiuli Yue, Harbin (CN)

(73) Assignee: Harbin Institute of Technology, Harbin (CN)

( * ) Notice: Subject to any disclaimer, the term of this patent is extended or adjusted under 35 U.S.C. 154(b) by 24 days.

(21) Appl. No.: 13/384,032

(22) PCT Filed: Jul. 19, 2010

(86) PCT No.: PCT/CN2010/075269
§ 371 (c)(1),
(2), (4) Date: Jan. 13, 2012

(87) PCT Pub. No.: WO2011/006453
PCT Pub. Date: Jan. 20, 2011

(65) Prior Publication Data
US 2012/0116064 A1   May 10, 2012

(30) Foreign Application Priority Data

| Jul. 17, 2009 | (CN) | 2009 1 0072538 |
| Dec. 15, 2009 | (CN) | 2009 1 0073423 |
| Jul. 9, 2010 | (CN) | 2010 1 0222232 |
| Jul. 9, 2010 | (CN) | 2010 1 0222238 |
| Jul. 13, 2010 | (CN) | 2010 1 0224640 |

(51) Int. Cl.
  *C07D 487/22* (2006.01)
  *C07D 323/04* (2006.01)
  *C07J 51/00* (2006.01)

(52) U.S. Cl.
  USPC ............ 540/145; 549/214; 552/505; 560/39; 560/43

(58) Field of Classification Search
  USPC ........ 540/145; 549/214; 552/505; 560/39, 43
  See application file for complete search history.

(56) References Cited

FOREIGN PATENT DOCUMENTS

| CN | 101109901 | 1/2008 |
| CN | 101613365 | 12/2009 |
| WO | 2008112150 A1 | 9/2008 |

*Primary Examiner* — Rebecca Anderson
(74) *Attorney, Agent, or Firm* — Greer, Burns & Crain, Ltd.

(57) ABSTRACT

This invention relates to a novel class of hybrid lipid compound based on pentaerythritol, their intermediates, preparation methods and uses thereof. Different kinds of functional groups such as alkyl chain, siloxane group, azobenzene, porphyrins, cholesterol, benzene ring and carboxyl were introduced into the four hydroxyl groups of pentaerythritol through chemical reaction to obtain the final hybrid lipid compounds based on pentaerythritol. Cerasomes prepared from such lipids have uniform size, silicate network surface, good stability and biocompatibility, and the leakage of drugs is not easy. The present liposome can be used as functional materials such as drugs or drug carriers, or used for optical storage and molecular devices, simulation, design and synthesis of artificial systems, nano-composite membrane materials and the removal of organic pollutants, etc., in addition, the preparation method of the present invention is simple, and it is easy for industrial production.

15 Claims, 7 Drawing Sheets

HYBRID LIPID COMPOUNDS BASED ON PENTAERYTHRITOL, INTERMEDIATES, PREPARATION METHODS AND USE THEREOF

This application is a U.S. National Stage under 35 U.S.C. §371 of International Application No. PCT/CN2010/075269, filed Jul. 19, 2010, which claims priority from Chinese Patent Application No. 200910072538.2, filed Jul. 17, 2009; Chinese Patent Application No. 200910073423.5, filed Dec. 15, 2009; Chinese Patent Application No. 201010222232.3, filed Jul. 9, 2010; Chinese Patent Application No. 201010222238.0, filed Jul. 9, 2010; and Chinese Patent Application No. 201010224640.2, filed Jul. 13, 2010.

FIELD OF THE INVENTION

The present invention belongs to the field of biomedical materials in materials science, specifically relates to hybrid lipid compounds, intermediates, preparation methods and use thereof which these lipids use pentaerythritol as the skeleton and contain aliphatic chain and siloxane groups.

BACKGROUND OF THE PRESENT DISCLOSURE

Liposome is an artificial membrane, when the amphiphilic molecules such as phospholipids and sphingolipids are dispersed in the aqueous phase, the hydrophobic tails of the molecules tend to aggregate together to prevent away from the aqueous phase, while the hydrophilic heads expose to the aqueous phase, phospholipids in water spontaneously form molecular organized assemblies relying on hydrophobic interaction, and form a bilayer structure of closed vesicles. Liposomes consist of a continuous bilayer or multi-layer lipid, each layer is lipid bilayer membrane, interlayer and liposome core are the aqueous phase, while the bilayer is the oil phase. Liposomes can be used as an experimental model of biomembrane, they are often used as carriers of drugs, enzymes or other agents in research and therapy, which are made more effective delivery to the target cells, and released through cell fusion.

Liposome shows many advantages, such as simple preparation, non-toxic and non-immunogenic response, in vivo degradation, easy to accomplish targeting, improving and prolonging the drug efficacy, moderating toxicity, avoiding drug resistance and changing the route of drug administration. In addition, it shows amphiphilic properties, hydrophilic and hydrophobic drugs can be both entrapped, water-soluble drugs can be loaded into the aqueous phase of the liposome, and oil-soluble drugs or amphiphilic drugs can be loaded into the lipid bilayer, so liposome has broad applicability for various drugs. Since the 1970s, liposomes have attracted much attention in the application of drug carriers.

However, liposomes have the limitation of instability which hampers its practical application. Specifically during storage, liposomes may be destroyed due to the reasons of drug leakage, aggregation of particles and oxidation or hydrolysis of phospholipids and so on. In the body, due to the interaction with blood albumin, conditioning factors, antibodies and other substances, liposomes may be ruptured, causing rapid leakage of encapsulated drugs, which are quickly degraded by some enzymes and swallowed by some phagocytic cells, and cannot effectively reach the targeted tissue to play their role. Therefore, the development of stable liposomes as drug carriers is a prerequisite for practical application, which shows great significance.

In recent years, a variety of functional liposomes have been gradually developed, such as temperature-sensitive liposomes, pH-sensitive liposomes, light-sensitive liposomes and so on, resulting in the possibility of site-fixed, time-regular, quantitative release of the drug. Among them, the light-sensitive liposome has unique advantages, when the drug is embedded in such type of material and delivered into a specific location of the body, configuration of light sensitive group can be changed simply by external light irradiation, leading to controlled release of the entrapped drug. Currently, many of the light-control materials reported are azobenzene derivatives, and introduction of azobenzene derivatives into liposome may reach the results of site-fixed, time-regular, quantitative release of drugs, but there are still some problems. For example, the use of azobenzene-containing surfactants as light-control material is prone to cause phase separation and fusion of liposome (Chem. Lett. (1981) 1001-1004), while the introduction of azobenzene containing phospholipids as light-controlled release materials will decrease the stability of liposome, lead to a sudden release of drugs, thus making it difficult for practical application (Photochem. Photobiol. 62 (1995) 24-29).

Cholesterol is an important component of cell membranes. The most important function of cholesterol is regulating physical and chemical properties of cell membrane (Yeagle P L. Biochim Biophys Acta 1985, 822 (3-4), 267-87; Yeagle P L. In: Yeagle P L, editor. Biology of cholesterol. Boca Raton (FL, USA): CRC Press, 1988. p. 121-146). In the cell membrane, cholesterol can interact with phospholipids or sphingolipids membrane and thus affect their properties. Increased levels of cholesterol in the lipid bilayer will expand and eventually eliminate coordination of the gel liquid crystal phase transition of the lipid bilayer (Lewis R N A H, McElhaney R N. In: Yegle P L, editor. The structure of biological membranes. Boca Raton (FL, USA): CRC Press, 1992. p. 73-156; Maulik P R, Shipley G G. Biophys J 1996, 70, 2256-2265). Cholesterol in the phospholipid bilayer is presented at an intermediate state, when above the phase transition temperature, the membrane fluidity is decreased, and when below the phase transition temperature, the membrane fluidity is increased (Demel R A, de Kruijff B. Biochim Biophys Acta 1976, 457 (2), 109-132). In the biologically relevant liquid crystal state, the arrangement of cholesterol in the membrane is relative ordered, so that movement rate of the alkyl chain of phospholipids decreases. In the membrane relatively ordered state, the membrane will be made more dense, thereby the mechanical properties of the membrane is increased and the permeation performance is decreased (Lund-Katz S, Laboda H M, McLean L R, Phillips M C. Biochemistry 1988, 27 (9), 3416-3423). In addition, cholesterol in organisms and traditional liposomes is generally in a free state. In the practical research and application, free cholesterol tends to quickly move out from the liposome membrane (Kan, C C; Yan, J.;

Bittman, R. Biochemistry 1992, 31, 1866-1874; Hamilton, J A Curr. Opin. Lipidol. 2003, 14, 263-271), which makes the stability of liposomes decrease and severely limits the application of liposome as drug carriers.

Porphyrin and its derivatives are macrocyclic molecules containing four conjugated pyrrole rings. It has a very wide range of applications in medicine, biochemistry, analytical chemistry, synthetic chemistry, and materials science because of its unique performance and easy modification, especially porphyrin derivatives, which have unique electronic structure and optical properties. In recent years, it has attracted much attention in medicine, optical storage, molecular devices, simulation design and synthesis of artificial systems for simulating charge separation, electron transfer and signal transduction. However, porphyrin derivative is generally a rigid molecule, it is difficult to be molded, and also its water solubility is relatively poor, which to some extent limits its practical application (J. Photochem. Photobiol., B 2002, 66, 89-106). In addition, when porphyrin derivatives including metal complexes are directly applied to the organism, there are also many problems in the safety and effectiveness.

The porphyrin molecule is embedded in the micelle, liposome, low-density lipid protein, polymer micelles or hydrophilic polymers and other carriers to improve its water solubility and biocompatibility. But the micelle carrier system is often prone to elicit acute hypersensibility (anaphylactic) reactions in vivo (Br. Med. J. 1980, 280, 1353-1353), the liposome is prone to opsonization and subsequent capture by the major defense system of the body (J. Pharm. Sci. 1995, 84, 166-173), and polymer shows poor tumor regression and increased accumulation in normal tissues (J. Pharm. Pharmacol. 2001, 53, 155-166). All the above carriers have a common drawback, in which the porphyrin derivatives embedded are easy to leak out, resulting in phototoxic side effects. The carrier-embedded silica-based nanoparticles with a high degree of stability, good biocompatibility and water dispersion can overcome the above disadvantages arising from other carriers, can be easily modified with different functional groups, and are not vulnerable to microbial attack. (J. Am. Chem. Soc. 2003, 125, 7860-7865).

In addition, encapsulation efficiency is a practical measurement for liposome's application as drug carriers. There are many ways to improve the encapsulation efficiency of liposome at present (Chinese Pharmaceutical Industry 2002, 33 (11), 564-568), and the way through intermolecular interactions or electrostatic attraction to improve liposome's encapsulation efficiency has significant advantages. Among them, liposomes with benzene rings can generate intermolecular conjugation with a number of drugs with similar groups, such as camptothecin, etc., which effectively increase the drug-embedded efficiency (Journal of Controlled Release, 2008, 127, 231-238). Liposomes derived from lipid containing carboxylic groups have many free carboxyl groups on the surface. On one hand, it facilitates coupling with drugs containing hydroxyl or amino groups such as doxorubicin. On the other hand, such liposomes can take a wealth of negative charge under specific pH values, which are well suited for the entrapment of drugs through electrostatic attraction. Thus the encapsulation and drug loading efficiency can be greatly improved. Meanwhile, liposomes with rich carboxyl groups on the surface can also facilitate the modification of a variety of targeting molecules to improve their targeting effect.

Currently, most of the liposomes are prepared by phospholipid, electrostatic, hydrophobic and van der Waals interactions between these liposomes with plasma proteins, conditioning factors, antibodies and other substances, which often leads to destabilization of liposomes, which generally makes liposomes be quickly removed before reaching the target in the circulation and encapsulated drug be quickly released prior to reaching their target tissue. This not only makes the drug unable effectively to play its role, but also may cause serious side effects. In addition, the drug can interact with the phospholipid of liposome (for example, anthracycline adriamycin showed surfactant or detergent-like effects to the phospholipid bilayer), which will lead to drug leakage during storage and make the liposome more unstable. The liposomes have shortcomings such as in vivo instability and storage instability, thus limiting the clinical application and industrial production of liposome. Although research of liposome has been carried out for decades, development of liposome-drug formulations is still very few, and poor stability of liposome is a serious problem in its commercialization process. Therefore, the development of stable liposomes as drug carriers is a prerequisite to practical application, which shows great significance.

Based on the above considerations, in the present invention, the inventors designed and synthesized a new class of hybrid lipids, the molecular structure of such lipids contains —Si(OEt)$_3$ or —Si(OCH$_3$)$_3$ groups. In aqueous solution such lipids can self-assemble to form vesicle structure with a lipid bilayer, and there is a stable Si—O—Si network structure on the vesicular surface and covalent bonding with the surface of the liposome, which greatly enhances its stability and water solubility.

Based on these novel hybrid lipids, the inventors have made a series of related research, for example, an azobenzene unit was introduced into the molecular structure of the novel hybrid lipids, and the lipid bilayer permeability can be easily controlled by light irradiation to achieve controlled release of drugs; cholesterol groups were covalent bonded with the novel hybrid lipids, and lipid bilayer fluidity and permeability can be further adjusted, thus formulation can effectively prevent the loss of cholesterol and can be used as a model for studying structure and function of cell membrane; benzene rings or carboxylic acid groups were bonded with new hybrid lipids, thus encapsulated hydrophobic or hydrophilic drugs can interact by conjugated effects or electrostatic attraction, thereby enhancing drug encapsulation efficiency; functional porphyrin moiety was covalent bonded with the novel hybrid lipids, which makes the porphyrin unit be orderly arranged in the bilayer structure of the formed vesicles, and then introduction of different metals through the coordination will develop a series of functional nanomaterials.

SUMMARY OF THE PRESENT INVENTION

The primary purpose of the present invention is to provide hybrid lipid compounds based on pentaerythritol and their intermediates, preparation methods and use thereof in view of the above problems, the lipid in the present invention can be hydrolyzed and condensed to form the corresponding liposome with silicate network surface (called cerasome); the prepared cerasomes show advantages of high stability, good biocompatibility, low toxicity and even non-toxicity, and difficulty of leaking the drug.

To achieve these goals, one aspect of the present invention provides a hybrid lipid compound based on pentaerythritol with a constructional formula

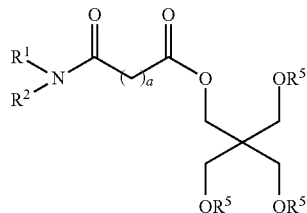

Wherein:
$R^1$ is $C_6$-$C_{18}$ alkyl, $R^2$ is $C_6$-$C_{18}$ alkyl, $R^5$ is one among the group consisting of —CO(CH$_2$)$_5$N(CH$_3$)$_2$(CH$_2$)$_3$Si(X)$_3$Y, —CO(CH$_2$)$_2$CONH(CH$_2$)$_3$Si(X)$_3$, —CO(CH$_2$)$_3$CONH(CH$_2$)$_3$Si(X)$_3$ and —CONH(CH$_2$)$_3$Si(X)$_3$, in which X is ethoxy or methoxy, Y is halogenated group; and a is 2 or 3.

Another aspect of the present invention provides a hybrid lipid compound based on pentaerythritol with a constructional formula

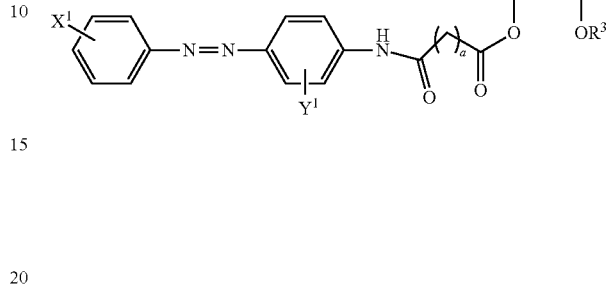

Wherein:
$R^1$ is $C_6$-$C_{18}$ alkyl, $R^2$ is $C_6$-$C_{18}$ alkyl, $R^3$ is one among the group consisting of —CO(CH$_2$)$_2$CONH(CH$_2$)$_3$Si(X)$_3$, —CO(CH$_2$)$_3$CONH(CH$_2$)$_3$Si(X)$_3$ and —CONH(CH$_2$)$_3$Si(X)$_3$, in which X is ethoxy or methoxy, a is 2 or 3, $X^1$ is one among the group consisting of —H, —CH$_3$, CH$_3$O—, halogenated group and —NO$_2$, $Y^1$ is one among the group consisting of —H, —CH$_3$, CH$_3$O— and halogenated group, when $Y^1$ is attached at the 2-position to the azobenzene unit, $Y^1$ is —H or halogenated group, while when $Y^1$ is attached at the 3-position of the azobenzene unit, $Y^1$ is —H, —CH$_3$, or CH$_3$O—.

Another aspect of the present invention provides a hybrid lipid compound based on pentaerythritol with a constructional formula

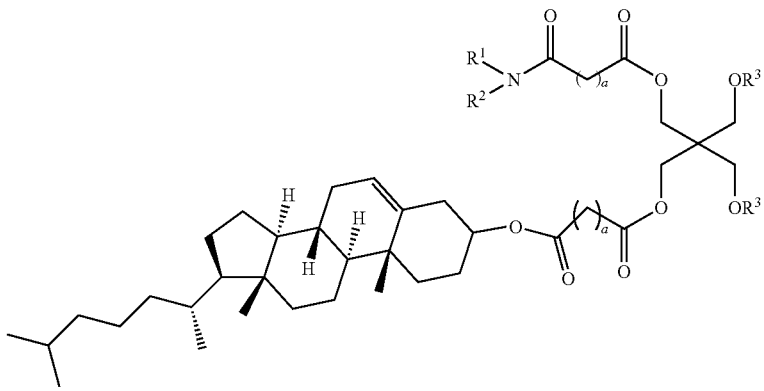

Wherein:
$R^1$ is $C_6$-$C_{18}$ alkyl, $R^2$ is $C_6$-$C_{18}$ alkyl, $R^3$ is one among the group consisting of —CO(CH$_2$)$_2$CONH(CH$_2$)$_3$Si(X)$_3$, —CO(CH$_2$)$_3$CONH(CH$_2$)$_3$Si(X)$_3$ and —CONH(CH$_2$)$_3$Si(X)$_3$, in which X is ethoxy or methoxy, and a is 2 or 3.

Another aspect of the present invention provides a hybrid lipid compound based on pentaerythritol with a constructional formula

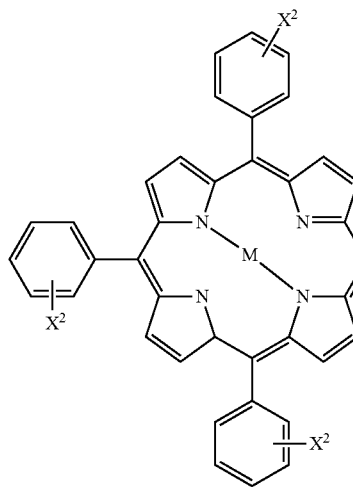
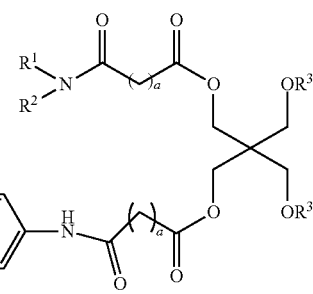

Wherein:

$R^1$ is $C_6$-$C_{18}$ alkyl, $R^2$ is $C_6$-$C_{18}$ alkyl, $R^3$ is one among the group consisting of —CO(CH$_2$)$_2$CONH(CH$_2$)$_3$Si(X)$_3$, —CO(CH$_2$)$_3$CONH(CH$_2$)$_3$Si(X)$_3$ and —CONH(CH$_2$)$_3$Si(X)$_3$, in which X is ethoxy or methoxy, a is 2 or 3; $X^2$ is one among the group consisting of —H, —CH$_3$, CH$_3$O— and halogenated group; M is metal ion coordinated with porphyrin ring, M is one among the group consisting of Iron, Zinc, Magnesium, Manganese, Cobalt, Copper, Molybdenum, Chromium, Gadolinium, Nickel, Vanadium, Aluminum, Gallium and Iridium.

Another aspect of the present invention provides a hybrid lipid compound based on pentaerythritol with a constructional formula

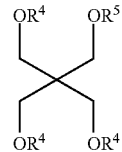

Wherein:

$R^4$ is $C_6$-$C_{18}$ alkyl, $R^5$ is one among the group consisting of —CO(CH$_2$)$_5$N(CH$_3$)$_2$(CH$_2$)$_3$Si(X)$_3$Y, —CO(CH$_2$)$_2$CONH(CH$_2$)$_3$Si(X)$_3$, —CO(CH$_2$)$_3$CONH(CH$_2$)$_3$Si(X)$_3$ and —CONH(CH$_2$)$_3$Si(X)$_3$, in which X is ethoxy or methoxy, Y is halogenated group.

Another aspect of the present invention provides a hybrid lipid compound based on pentaerythritol with a constructional formula

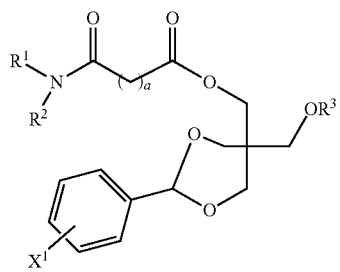
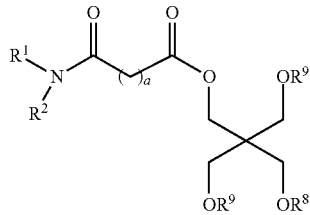

Wherein:

$R^1$ is $C_6$-$C_{18}$ alkyl, $R^2$ is $C_6$-$C_{18}$ alkyl, $R^8$ is one among the group consisting of CO(CH$_2$)$_2$CONH(CH$_2$)$_3$Si(X)$_3$, —CO(CH$_2$)$_3$CONH(CH$_2$)$_3$Si(X)$_3$ and —CONH(CH$_2$)$_3$Si(X)$_3$, in which X is ethoxy or methoxy, $R^9$ is selected among the group consisting of —CO(CH$_2$)$_2$COOH and —CO(CH$_2$)$_3$COOH, a is 2 or 3.

Wherein, the said halogenated group is selected among the group consisting of Fluorine, Chlorine, Bromine, Iodine.

In particular, $R^1$ is one among the group consisting of hexyl, octyl, undecyl, dodecyl, tridecyl, tetradecyl, fifteen alkyl, hexadecyl, seventeen alkyl and octadecyl. $R^2$ is one among the group consisting of hexyl, octyl, undecyl, dodecyl, tridecyl, tetradecyl, fifteen alkyl, hexadecyl, seventeen alkyl and octadecyl.

Another aspect of the present invention provides a preparation method of a hybrid lipid compound based on pentaerythritol with a constructional formula Wherein:

$R^1$ is $C_6$-$C_{18}$ alkyl, $R^2$ is $C_6$-$C_{18}$ alkyl, $R^3$ is one among the group consisting of —CO(CH$_2$)$_2$CONH(CH$_2$)$_3$Si(X)$_3$, —CO(CH$_2$)$_3$CONH(CH$_2$)$_3$Si(X)$_3$ and —CONH(CH$_2$)$_3$Si(X)$_3$, in which X is ethoxy or methoxy, a is 2 or 3. $X^1$ is one among the group consisting of —H, —CH$_3$, CH$_3$O—, halogenated group and —NO$_2$.

Another aspect of the present invention provides a hybrid lipid compound based on pentaerythritol with a constructional formula

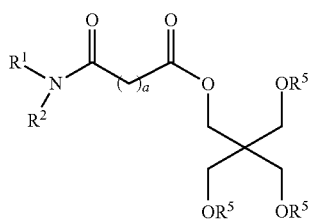

which comprises following steps:
1) forming a compound 1 with a constructional formula

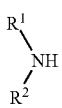

by reacting alkyl amines and alkyl bromide under reflux through substitution reaction, wherein the alkyl amines is $R^1$—$NH_2$, and the alkyl bromide is $R^2$—Br, in which $R^1$ is $C_6$-$C_{18}$, alkyl chains and $R^2$ is $C_6$-$C_{18}$ alkyl chains;
2) forming a compound with a constructional formula

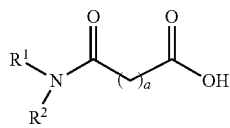

by reacting the compound 1 with succinic anhydride or glutaric anhydride through nucleophilic reaction, wherein, a is 2 or 3; then forming a compound with a constructional formula

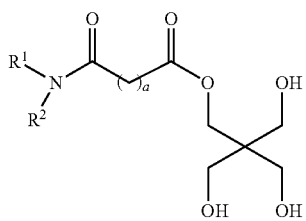

by reacting the compound 2 with excess 4 to 6 times of pentaerythritol through esterification reaction, wherein a is 2 or 3;
3) forming a hybrid lipid compound with a constructional formula

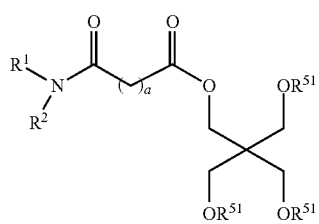

by reacting the compound 3 with 3-Isocyanatopropyltriethoxysilane or 3-Isocyanatopropyltrimethoxysilane through nucleophilic reaction, wherein $R^{51}$ is —$CONH(CH_2)_3Si(X)_3$, in which X is ethoxy or methoxy;

or forming a hybrid lipid compound with a constructional formula

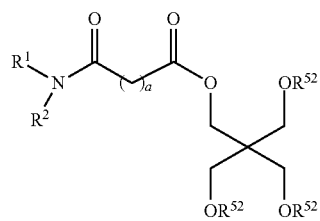

by reacting the compound 3 with 6-Bromohexanoyl chloride through esterification reaction, following reacting with dimethylamine gas saturated tetrahydrofuran solution through nucleophilic reaction, and then reacting with 3-Bromopropyltriethoxysilane or 3-Bromopropyltrimethoxysilane through nucleophilic reaction, wherein $R^{52}$ is —$CO(CH_2)_5N(CH_3)_2$ $(CH_2)_3Si(X)_3Y$, X is ethoxy or methoxy, and Y is halogenated group;

or forming a hybrid lipid compound with a constructional formula

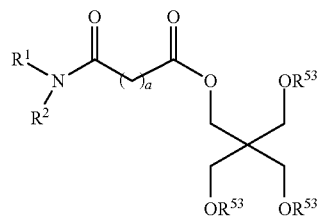

by reacting the compound 3 with succinic anhydride or glutaric anhydride through nucleophilic reaction, following reacting with 3-aminopropyltriethoxysilane or 3-aminopropyltrimethoxysilane through condensation reaction, and then dehydrating, wherein $R^{53}$ is one among the group consisting of —$CO(CH_2)_2CONH(CH_2)_3Si(X)_3$ and —$CO(CH_2)_3CONH(CH_2)_3Si(X)_3$, in which X is ethoxy or methoxy.

Wherein, the said halogenated group is one among the group consisting of Fluorine, Chlorine, Bromine, Iodine.

In particular, $R^1$ is one among the group consisting of hexyl, octyl, undecyl, dodecyl, tridecyl, tetradecyl, fifteen alkyl, hexadecyl, seventeen alkyl and octadecyl. $R^2$ is one among the group consisting of hexyl, octyl, undecyl, dodecyl, tridecyl, tetradecyl, fifteen alkyl, hexadecyl, seventeen alkyl and octadecyl.

Wherein, the time of the said refluxing in step "1)" is 5 days, the reaction time in step "3)" is 2-3 days.

Another aspect of the present invention provides a preparation method of a hybrid lipid compound based on pentaerythritol with a constructional formula

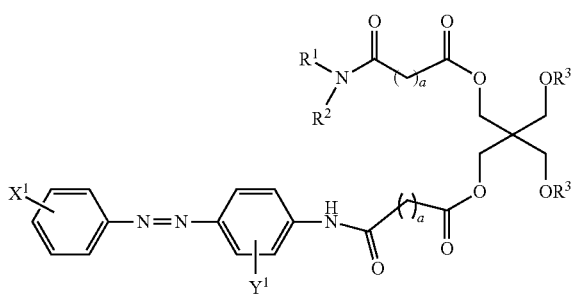

which comprises following steps:
1) forming a compound 2 with a constructional formula

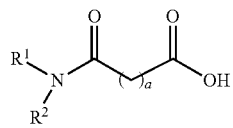

by reacting a compound 1 with a constructional formula

with a compound 4 with a constructional formula

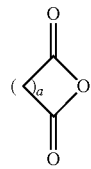

in polar organic solvent under 25-70° C. for 24-48 h, following washing in turn with acidic water and water, and then recrystallizing, wherein the molar ratio of the compound 1 to the compound 4 is 1:1.5-4, a is 2 or 3;
2) forming a compound 6 with a constructional formula

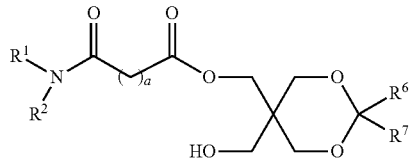

by reacting the compound 2 with N,N'-dicyclohexylcarbodiimide (DCC), 4-dimethylaminopyridine (DMAP) and a compound 5 with a constructional formula

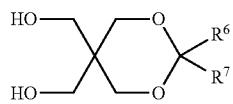

in polar organic solvent under 50-80° C. for 12-36 h, wherein the molar ratio of the compound 2, DCC, DMAP and the compound 5 is 1:1-3:0.8-1.2:3-6, $R^6$ is one among the group consisting of —H, phenyl and —$CH_3$, $R^7$ is one among the group consisting of —H, phenyl and —$CH_3$; 3) forming a compound 7 with a constructional formula

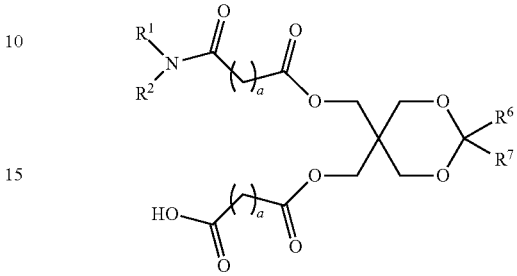

by reacting the compound 6 with 4-dimethylaminopyridine (DMAP), deacid reagent and the compound 4 in aprotic organic solvent under 25-70° C. for 24-48 h, following washing in turn with acidic water and water, and then purifying through column chromatography, wherein the molar ratio between the compound 6, DMAP, deacid reagent and the compound 4 is 1:0.4-1:1-6:2-5, and a is 2 or 3.

4) forming a compound 8 with a constructional formula

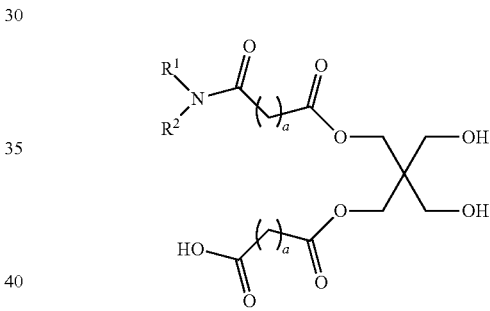

by reacting the compound 7 with hydrogen in the presence of catalyst in a mixed reaction solvent of tetrahydrofuran and methanol or ethanol under 25-80° C. for 12-48 h, wherein the molar ratio of the compound 7 to the catalyst is 1:0.4-0.6, hydrogen pressure is 1.0-1.2 MPa, the volume ratio of tetrahydrofuran to methanol or ethanol is 3-4:1, the catalyst is palladium/carbon or palladium hydroxide/carbon;

5) forming a compound 10 with a constructional formula

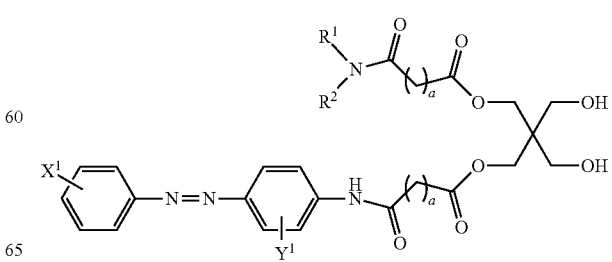

by reacting a compound 9 with a constructional formula

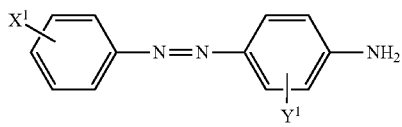

with the compound 8 and DCC in aprotic organic solvent under 25-45° C. for 24-60 h, wherein the molar ratio between the compound 8, DCC and the compound 9 is 1:1.2-1.5:1.1-2;
6) forming a hybrid lipid compound with a constructional formula

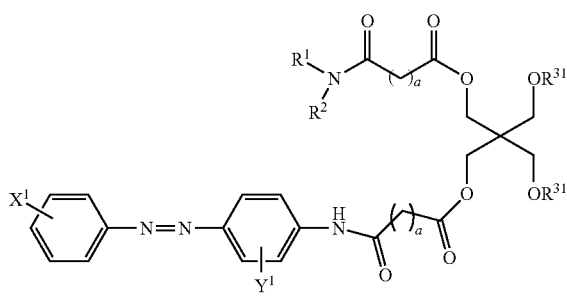

by reacting a compound 11 with a constructional formula

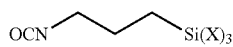

with the compound 10 and dibutyltin dilaurate in aprotic organic solvents under 40-70° C. for 48-72 h, wherein the molar ratio between the compound 10, the compound 11 and Dibutyltin dilaurate is 1:2-4:0.2-0.8, $R^{31}$ is —CONH$(CH_2)_3Si(X)_3$, in which X is ethoxy or methoxy;
or forming a compound 12 with a constructional formula

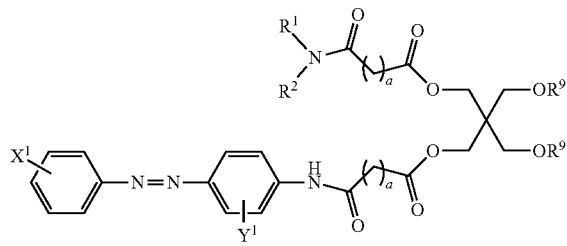

by reacting the compound 10 with DMAP, deacid reagent and the compound 4 in aprotic organic solvent under 25-70° C. for 24-48 h, following washing in turn with acidic water and water, and then purifying through column chromatography, wherein $R^9$ is one among the group consisting of —CO$(CH_2)_2$COOH and —CO$(CH_2)_3$COOH, the molar ratio between the compound 10, DMAP, deacid reagent and the compound 4 is 1:0.8-2:3-8:4-8;

finally, forming a hybrid lipid compound with a constructional formula

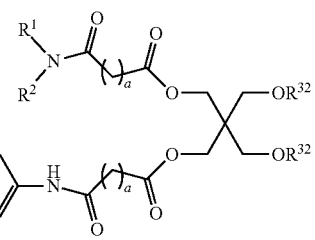

by reacting a compound 13 with a constructional formula

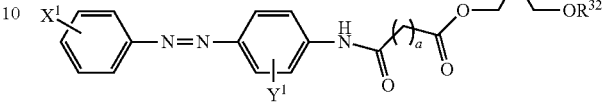

with the compound 12 and DCC in aprotic organic solvent under 25-40° C. for 24-36 h, wherein $R^{32}$ is one among the group consisting of —CO$(CH_2)_2$CONH$(CH_2)_3$Si$(X)_3$ and —CO$(CH_2)_3$CONH$(CH_2)_3$Si$(X)_3$, in which X is ethoxy or methoxy, the molar ratio between the compound 12, DCC and the compound 13 is 1:1-2:1.5-2.0.

Wherein, when $Y^1$ is attached at the 2-position to the azobenzene unit, $Y^1$ is —H, or halogenated group; when $Y^1$ is attached at the 3-position of the azobenzene unit, $Y^1$ is —H, —$CH_3$, or $CH_3$O—.

Wherein, $R^7$ is —H when $R^6$ is phenyl, or $R^7$ is —$CH_3$ when $R^6$ is —$CH_3$.

Wherein, the said halogenated group is one among the group consisting of Fluorine, Chlorine, Bromine, Iodine; $R^1$ is one among the group consisting of hexyl, octyl, undecyl, dodecyl, tridecyl, tetradecyl, fifteen alkyl, hexadecyl, seventeen alkyl and octadecyl; $R^2$ is selected among the groups consisting of hexyl, octyl, undecyl, dodecyl, tridecyl, tetradecyl, fifteen alkyl, hexadecyl, seventeen alkyl and octadecyl.

Wherein, the polar organic solvent in step "1)" is one among the group consisting of tetrahydrofuran, acetone, dimethylformamide and acetonitrile, the molar ratio of the compound 1 to the compound 4 is 1:2-2.5.

The polar organic solvent in step "2)" is one among the group consisting of tetrahydrofuran, acetone, dimethylformamide and acetonitrile, the molar ratio of the compound 2, DCC, DMAP and the compound 5 is 1:1.5-2:0.9-1.1:4-5.

In step "3)", the molar ratio of the compound 6, DMAP, deacid agent and the compound 4 is 1:0.4-0.6:3-5:3-4.

In step "6)", the molar ratio of the compound 10, the compound 11 and Dibutyltin dilaurate is 1:2-2.5:0.3-0.5, the molar ratio of the compound 10, DMAP, the deacid agent and the compound 4 is 1:1-1.5:5-6:6-7.

In particular, the said deacid agent is triethylamine or pyridine.

In particular, the said polar organic solvent is one among the group consisting of tetrahydrofuran, acetone, dimethylformamide and acetonitrile, the said aprotic organic solvent is one among the group consisting of benzene, toluene, methylene chloride, chloroform, DMSO and DMF.

Another aspect of the present invention provides a preparation method of a hybrid lipid compound based on pentaerythritol with a constructional formula

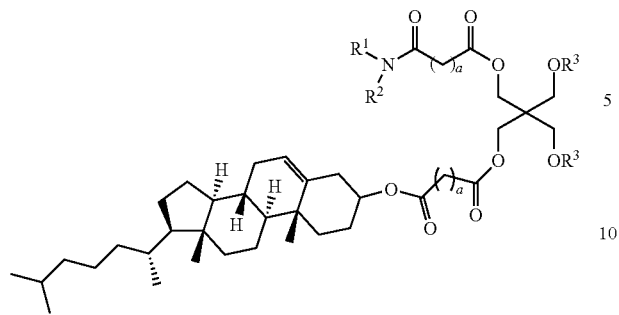

5

10 which comprises following steps:
1) forming a compound 15 with a constructional formula

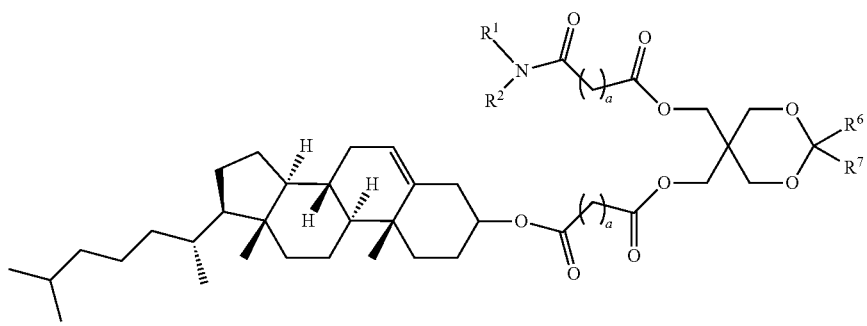

by reacting a compound 14 with a constructional formula

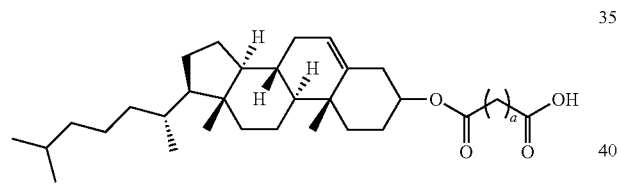

35

40 with the compound 6, DCC and DMAP in polar organic solvents under 50-80° C. for 12-36 h, wherein the molar ratio between the compound 6, DCC, DMAP and the compound 14 is 1:1-3:0.8-1.2:1-3, a is 2 or 3, $R^6$ is phenyl or —$CH_3$, $R^7$ is —H or —$CH_3$;

2) forming a compound 16 with a constructional formula

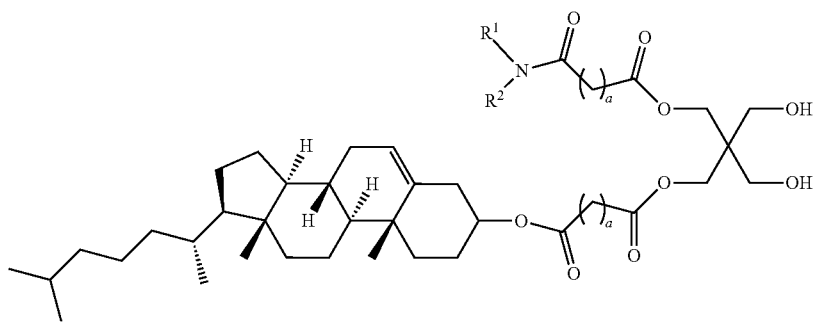

by reacting the compound 15 with hydrogen in the presence of catalyst in a mixed reaction solvent of tetrahydrofuran and methanol or ethanol under 25-80° C. for 12-48 h, wherein the molar ratio of the compound 15 to catalyst is 1:0.4-0.6, hydrogen pressure is 1.0-1.2 MPa, the volume ratio of tetrahydrofuran to methanol or ethanol is 3-4:1, the catalyst is palladium/carbon or palladium hydroxide/carbon;

3) forming a hybrid lipid compound with a constructional formula

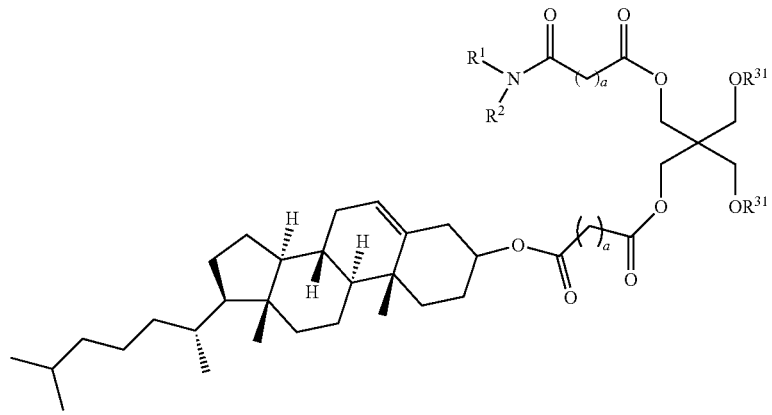

by reacting the compound 16 with the compound 11 and Dibutyltin dilaurate in aprotic organic solvent under 40-70° C. for 48-72 h, wherein $R^{31}$ is —$CONH(CH_2)_3Si(X)_3$, in which X is ethoxy or methoxy, the molar ratio between the compound 16, the compound 11 and Dibutyltin dilaurate is 1:2-4:0.2-0.8;

4) forming a compound 17 with a constructional formula

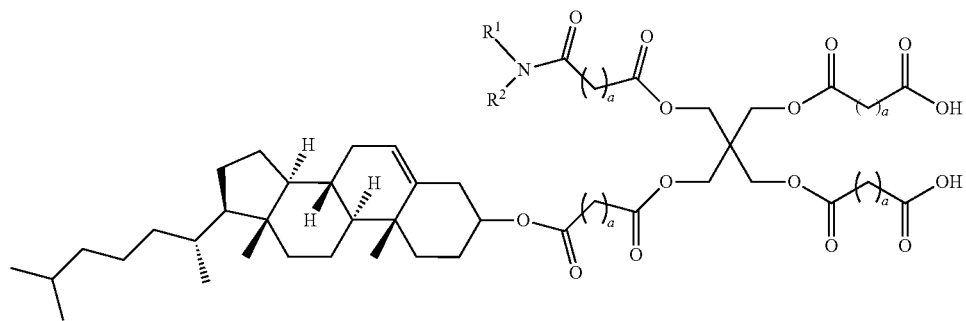

by reacting the compound 16 with DMAP, deacid reagent and the compound 4 in aprotic organic solvents under 25-70° C. for 24-48 h, following washing in turn with acidic water and water, and then purifying through column chromatography, wherein the molar ratio between the compound 16, DMAP, the deacid reagent and the compound 4 is 1:0.8-2:3-8:4-8, a is 2 or 3;

5) forming a hybrid lipid compound with a constructional formula

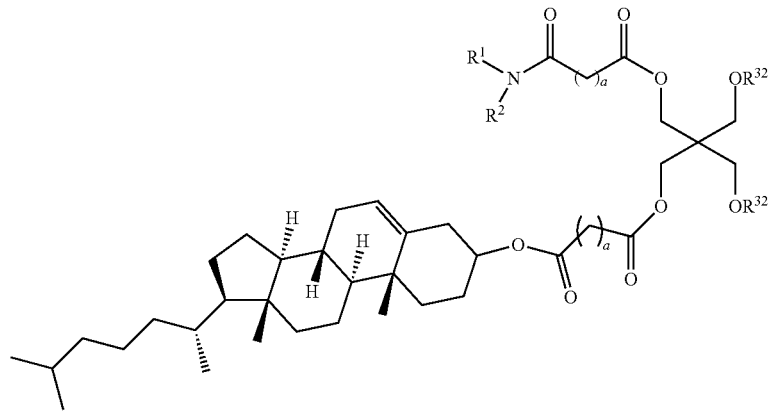

by reacting the compound 17 with the compound 13 and DCC in aprotic organic solvent under 25-40° C. for 24-36 h, wherein $R^{32}$ is one among the group consisting of —CO$(CH_2)_2CONH(CH_2)_3Si(X)_3$ and —CO$(CH_2)_3CONH(CH_2)_3Si(X)_3$, in which X is ethoxy or methoxy, the molar ratio between the compound 17, DCC and the compound 13 is 1:1-2:2.0-2.5.

Wherein, $R^1$ is one among the group consisting of hexyl, octyl, undecyl, dodecyl, tridecyl, tetradecyl, fifteen alkyl, hexadecyl, seventeen alkyl and octadecyl; $R^2$ is one among the group consisting of hexyl, octyl, undecyl, dodecyl, tridecyl, tetradecyl, fifteen alkyl, hexadecyl, seventeen alkyl and octadecyl.

Wherein, the said polar organic solvent in step "1)" is one among the group consisting of tetrahydrofuran, acetone, dimethylformamide and acetonitrile, the molar ratio between the compound 6, DCC DMAP and the compound 14 is 1:1.5-2: 0.9-1.1:1.2-2.5; in step "3)", the molar ratio between the compound 16, the compound 11 and dibutyltin dilaurate is 1:2-2.5:0.3-0.5; in step "4)", the said deacid agent is triethylamine or pyridine, the molar ratio between the compound 16, DMAP, the deacid agent and the compound 4 is 1:1-1.5:5-6: 6-7.

In particularly, the said polar organic solvent is one among the group consisting of tetrahydrofuran, acetone, dimethylformamide and acetonitrile, the said aprotic organic solvent is one among the group consisting of benzene, toluene, methylene chloride, chloroform, DMSO and DMF.

Another aspect of the present invention provides a preparation method of a hybrid lipid compound based on pentaerythritol with a constructional formula

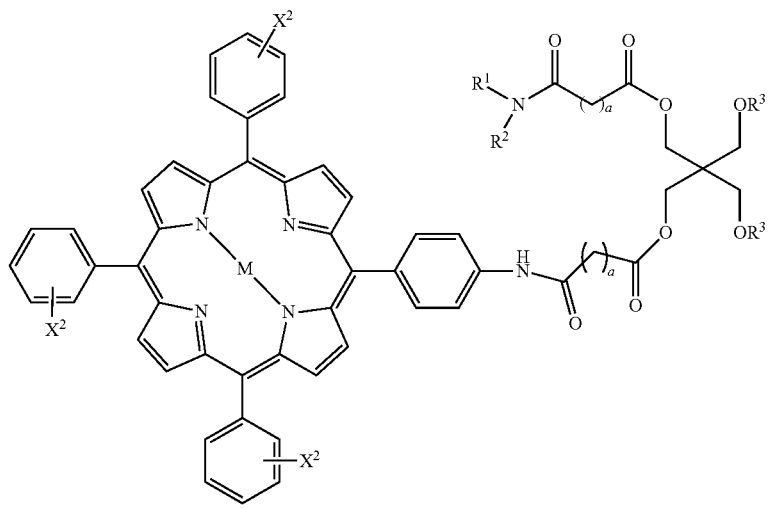

which comprises following steps:
1) forming a compound 19 with a constructional formula
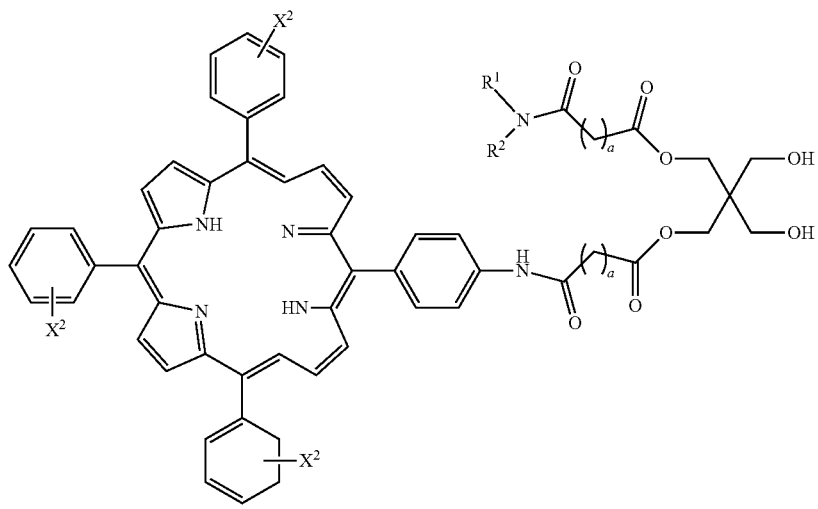
by reacting a compound 18 with a constructional formula
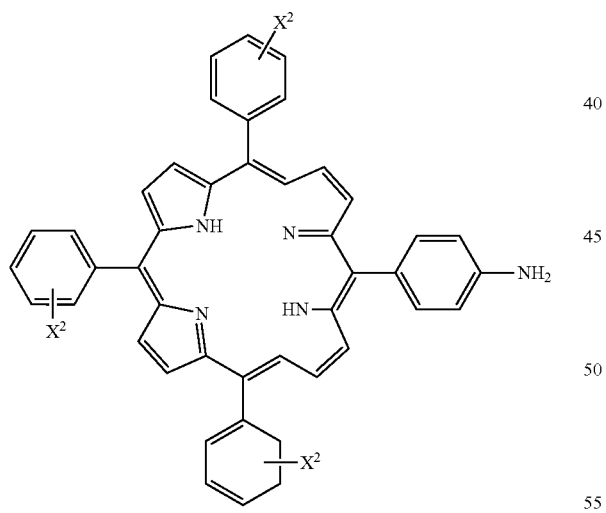
with the compound 8 and DCC in aprotic organic solvents under 25-45° C. for 24-72 h, wherein the molar ratio between the compound 8, DCC and the compound 18 is 1:1.2-1.5:1.1-1.2, a is 2 or 3, $X^2$ is one among the group consisting of —H, —CH$_3$, CH$_3$O— and halogen;

2) forming a hybrid lipid compound 20 with a constructional formula

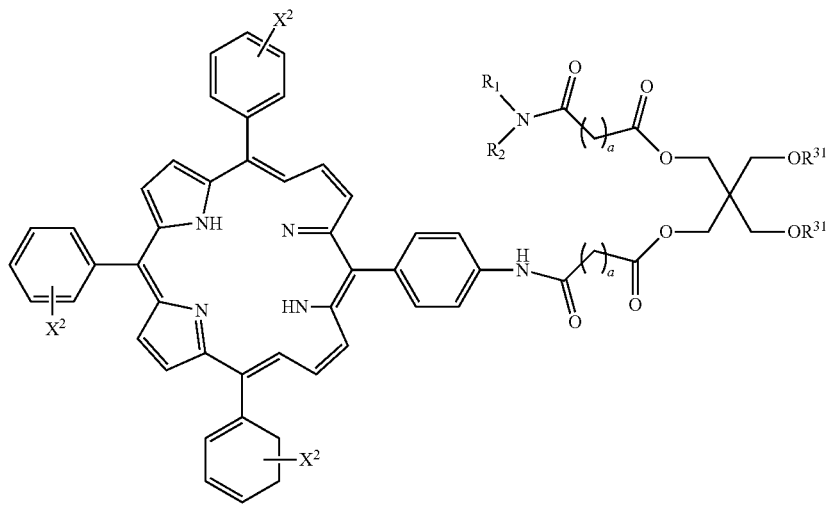

by reacting the compound 11 with the compound 19 and dibutyltin dilaurate in aprotic organic solvents under 40-80° C. for 36-72 h, wherein $R^{31}$ is —CONH(CH$_2$)$_3$Si(X)$_3$, in which X is ethoxy or methoxy, the molar ratio between the compound 19, the compound 11 and dibutyltin dilaurate is 1:2-5:0.2-1.0;

3) forming a compound 21 with a constructional formula

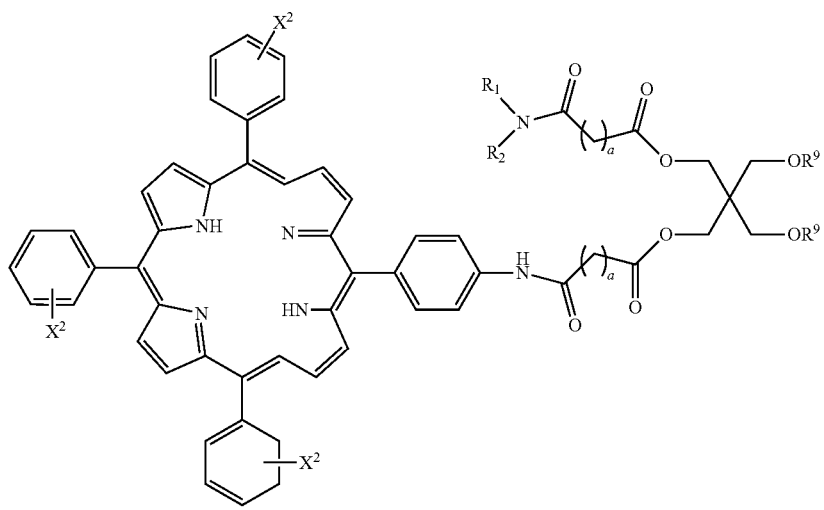

by reacting the compound 19 with DMAP, deacid reagent and the compound 4 in aprotic organic solvent under 25-70° C. for 24-48 h, following washing in turn with acidic water and water, then purifying through Column chromatography, wherein $R^9$ is selected among the group consisting of —CO(CH$_2$)$_2$COOH and —CO(CH$_2$)$_3$COOH, the molar ratio between the compound 19, DMAP, the deacid reagent and the compound 4 is 1:0.8-2:3-9:3-10, the deacid agent is triethylamine or pyridine;

4) forming a hybrid lipid compound 22 with a constructional formula

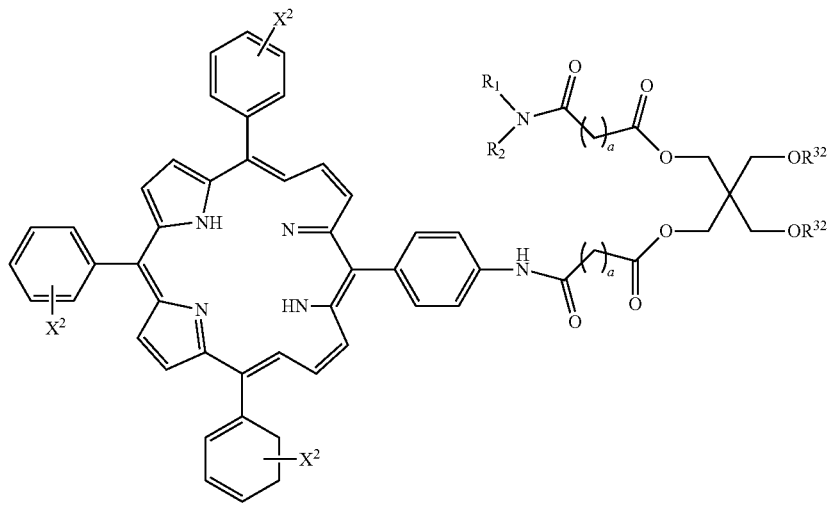

by reacting the compound 13 with compound 21 and DCC in aprotic organic solvents under 25-45° C. for 24-48 h, wherein $R^{32}$ is selected among the group consisting of —CO(CH$_2$)$_2$CONH(CH$_2$)$_3$Si(X)$_3$ and —CO(CH$_2$)$_3$CONH(CH$_2$)$_3$Si(X)$_3$, in which X is ethoxy or methoxy, the molar ratio between the compound 21, DCC and the compound 13 is 1:1-2:1.5-2.0;

5) forming a hybrid lipid compound with a constructional formula

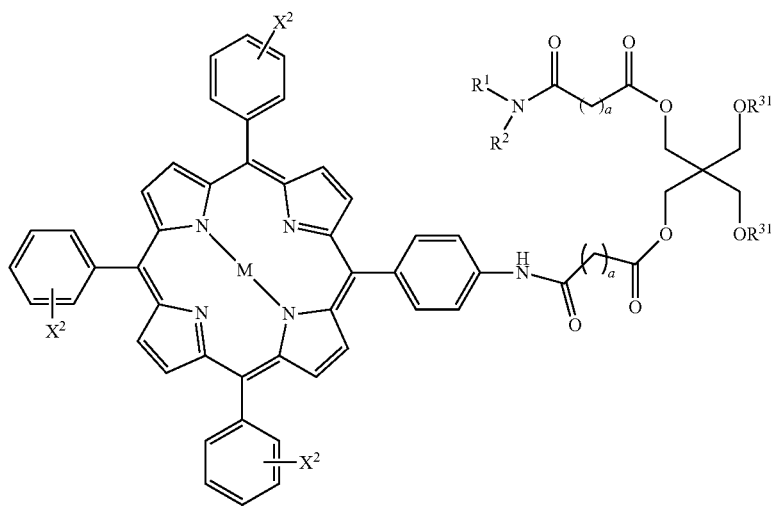

by reacting a Metal salts compound 23 having the formula of $MY^2$ with the compound 20 in organic solvent under 25-180° C. for 2-48 h, and later removing reaction solvent in vacuum, then washing, the crude product was purified by column chromatography, wherein the molar ratio of the compound 20 and the compound 23 is 1:5-25, $R^{31}$ is —CONH(CH$_2$)$_3$Si(X)$_3$, in which X is ethoxy or methoxy; or forming a hybrid lipid compound with a constructional formula

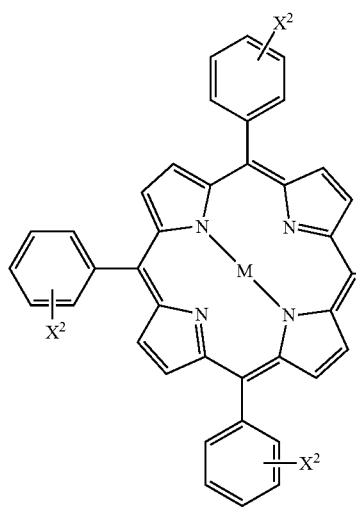
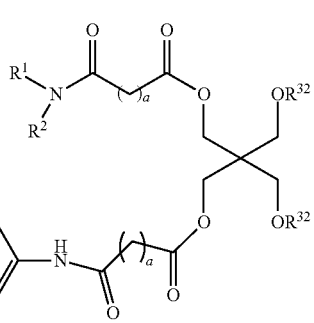

by reacting a Metal salts compound 23 having the formula of $MY^2$ with the compound 22 under 25-180° C. for 2-48 h, following removing reaction solvent in vacuum, later washing with water, the crude product was then purified by column chromatography, wherein the molar ratio of the compound 22 and the compound 23 is 1:5-25, $R^{32}$ is one among the group consisting of —CO(CH$_2$)$_2$CONH(CH$_2$)$_3$Si(X)$_3$ and —CO(CH$_2$)$_3$CONH(CH$_2$)$_3$Si(X)$_3$, in which X is ethoxy or methoxy; $X^2$ is one among the group consisting of —H, —CH$_3$, CH$_3$O— and halogen, M is the metal ion coordinated with porphyrin ring, and $Y^2$ is the anion which formed metal salts with M.

Wherein, the said halogenated group is one among the group consisting of Fluorine, Chlorine, Bromine, Iodine, $R^1$ is one among the group consisting of hexyl, octyl, undecyl, dodecyl, tridecyl, tetradecyl, fifteen alkyl, hexadecyl, seventeen alkyl or octadecyl; $R^2$ is one among the group consisting of hexyl, octyl, undecyl, dodecyl, tridecyl, tetradecyl, fifteen alkyl, hexadecyl, seventeen alkyl or octadecyl; M is one among the group consisting of Iron, Zinc, Magnesium, Manganese, Cobalt, Copper, Molybdenum, Chromium, Gadolinium, Nickel, Vanadium, Aluminum, Gallium or Iridium; The anion is halogen anion or acetate ion.

In particularly, the said apolatic organic solvent is one among the group consisting of benzene, toluene, dichloromethane, chloroform, DMSO and DMF.

In step "2)", wherein the molar ratio of the compound 19, the compound 11 and dibutyltin dilaurate is 1:2-3:0.3-0.6; in step "3)", wherein the molar ratio of the compound 19, DMAP, the deacid agent and the compound 4 is 1:1-1.5:5-6:5-8; in step "5)", wherein the apolatic organic solvent is one among DMSO, dimethyl formamide, methanol, ethanol, methylene chloride and chloroform; in step "5", wherein the molar ratio of the compound 20 to the compound 23 is 1:10-15, and the molar ratio of the compound 22 to the compound 23 is 1:10-15.

Another aspect of the present invention provides a preparation method of a hybrid lipid compound based on pentaerythritol with a constructional formula

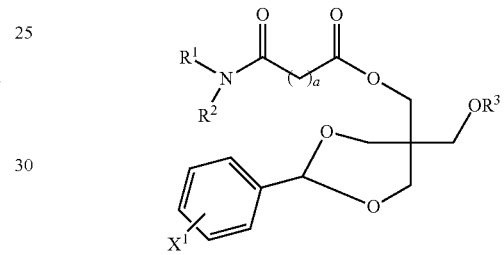

which comprises the following steps:

1) forming a compound 2 with a constructional formula

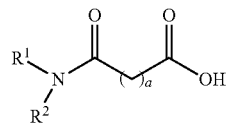

by reacting a compound 1 with a constructional formula

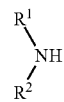

with a compound 4 a constructional formula

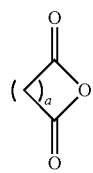

in polar organic solvent under 25-70° C. for 24-48 h, following washing in turn with acidic water and water, then recrystallizing, wherein the molar ratio of the compound 1 to the compound 4 is 1:1.5-4, a is 2 or 3, $R^1$ is $C_6$-$C_{18}$ alkyl, and $R^2$ is $C_6$-$C_{18}$ alkyl;

2) forming a compound 25 with a constructional formula

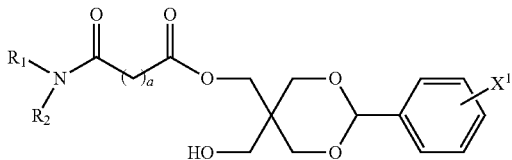

by reacting a compound 24 with a constructional formula

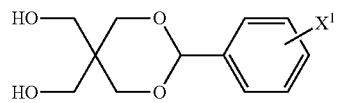

with the compound 2, N,N'-dicyclohexylcarbodiimide and 4-dimethylaminopyridine in polar organic solvent under 50-80° C. for 12-36 h, wherein X1 is —H, —$CH_3$, $CH_3O$—, halogen or —$NO_2$, the molar ratio between the compound 2, N,N'-dicyclohexylcarbodiimide, 4-dimethylaminopyridine and the compound 24 is 1:1-3:0.8-1.2:3-6;

3) forming a hybrid lipid compound with a constructional formula

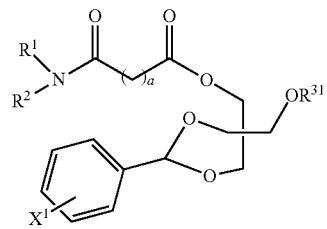

by reacting the compound 25, the compound 11 and dibutyltin dilaurate in nonpolar organic solvent under 40-70° C. for 48-72 h, wherein $R^{31}$ is —$CONH(CH_2)_3Si(X)_3$, in which X is ethoxy or methoxy, and the molar ratio between the compound 25, the compound 11 and dibutyltin dilaurate is 1:1-2: 0.2-0.8;

4) forming a compound 26 with a constructional formula

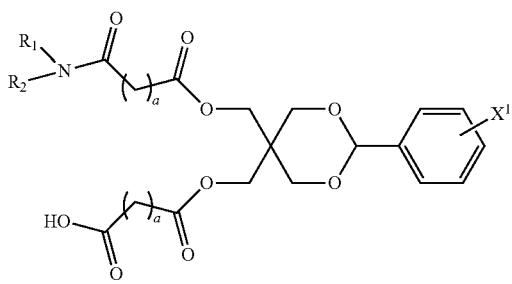

by reacting the compound 25 with 4-dimethylaminopyridine, deacid reagent and the compound 4 in aprotic organic solvent under 25-70° C. for 24-48 h, following washing in turn with acidic water and water, then recrystallizing, wherein the molar ratio between the compound 25, 4-dimethylaminopyridine, the deacid agent and the compound 4 is 1:0.4-1:1-6: 2-5;

5) forming a hybrid lipid compound with a constructional formula

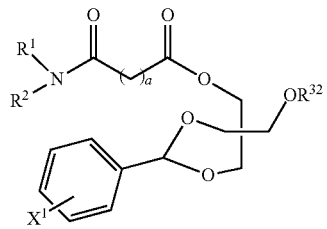

by reacting the compound 26 with the compound 13 and N,N'-dicyclohexylcarbodiimide in aprotic organic solvent, under 25-40° C. for 24-36 h, wherein $R^{32}$ is —$CO(CH_2)_2CONH(CH_2)_3Si(X)_3$ or —$CO(CH_2)_3CONH(CH_2)_3Si(X)_3$, in which X is ethoxy or methoxy; and the molar ratio between the compound 26, N,N'-dicyclohexylcarbodiimide and the compound 13 is 1:1-2:1.1-1.5.

Wherein, in step "1)", the molar ratio of the compound 1 to the compound 4 is 1:2-2.5; in step "2)", the molar ratio between the compound 2, DCC, DMAP and the compound 24 is 1:1.5-2:0.9-1.1:4-5; in step "3)", the molar ratio between the compound 25, the compound 11 and dibutyltin dilaurate is 1:1-1.25:0.3-0.5; in step "4", the molar ratio between the compound 25, DMAP, the deacid agent and the compound 4 is 1:0.4-0.6:3-5:3-4.

In particularly, the said polar organic solvent is one among the group consisting of tetrahydrofuran, acetone, dimethylformamide and acetonitrile; the said apolatic organic solvent is one among the group consisting of Benzene, toluene, dichloromethane, chloroform, DMSO and DMF; the deacid agent is triethylamine or pyridine.

Another aspect of the present invention provides a preparation method of a hybrid lipid based on pentaerythritol with a constructional formula

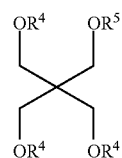

which comprises the following steps:
1) forming a compound 27 with a constructional formula

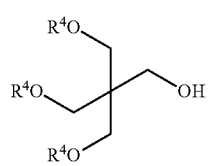

by reacting pentaerythritol and alkyl bromide with a constructional formula of $R^4$—Br in alkaline condition through nucleophilic substitution reaction, wherein the molar ratio of pentaerythritol to alkyl bromide is 1:3, and $R^4$ is $C_6$-$C_{18}$ alkyl;

2) forming a hybrid lipid compound with a constructional formula

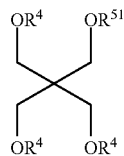

by reacting the compound 27 with 3-isocyanatopropyltriethoxysilane or 3-isocyanatopropyltrimethoxysilane through nucleophilic reactions, wherein $R^{51}$ is —CONH(CH$_2$)$_3$Si(X)$_3$, in which X is ethoxy or methoxy;

or forming a hybrid lipid compound with a constructional formula

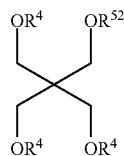

by reacting the compound 27 with 6-Bromohexanoyl chloride through esterification reaction, following reacting with dimethylamine gas saturated tetrahydrofuran solution through nucleophilic reaction, and then reacting with 3-Bromopropyltriethoxysilane or 3-Bromopropyltrimethoxysilane through nucleophilic reaction, wherein $R^{52}$ is —CO(CH$_2$)$_5$N(CH$_3$)$_2$(CH$_2$)$_3$Si(X)$_3$Y, in which X is ethoxy or methoxy and Y is halogenated group;

or forming a hybrid lipid compound with a constructional formula

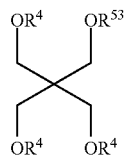

by reacting the compound 27 with succinic anhydride or glutaric anhydride through nucleophilic reaction, following reacting with 3-aminopropyltriethoxysilane or 3-aminopropyltrimethoxysi lane through nucleophilic reaction, wherein $R^{53}$ is —CO(CH$_2$)$_2$CONH(CH$_2$)$_3$Si(X)$_3$ or —CO(CH$_2$)$_3$CONH(CH$_2$)$_3$Si(X)$_3$, in which X is ethoxy or methoxy.

Wherein, the said halogenated group is one among the group consisting of Fluorine, Chlorine, Bromine, Iodine; $R^4$ is one among the group consisting of hexyl, octyl, undecyl, dodecyl, tridecyl, tetradecyl, fifteen alkyl, hexadecyl, seventeen alkyl or octadecyl.

Another aspect of the present invention provides a preparation method of a hybrid lipid based on pentaerythritol with a constructional formula

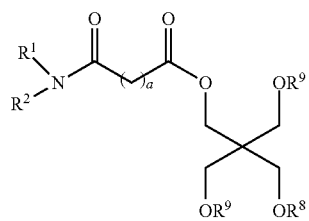

which comprises the following steps:

1) forming a compound 8 with a constructional formula

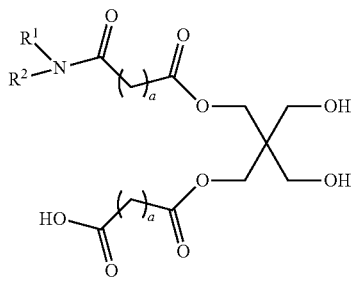

by reacting the compound 26 with hydrogen in the presence of catalyst in a mixed reaction solvent of tetrahydrofuran and methanol or ethanol under 25-80° C. for 12-48 h, wherein the molar ratio of the compound 26 to the catalyst is 1:0.4-0.6, hydrogen pressure is 1.0-1.2 MPa, the volume ratio of tetrahydrofuran to methanol or ethanol is 3-4:1, the catalyst is palladium/carbon or palladium hydroxide/carbon, a is 2 or 3, $R^1$ is $C_6$-$C_{18}$ alkyl, and $R^2$ is $C_6$-$C_{18}$ alkyl;

2) forming a hybrid lipid compound 28 with a constructional formula

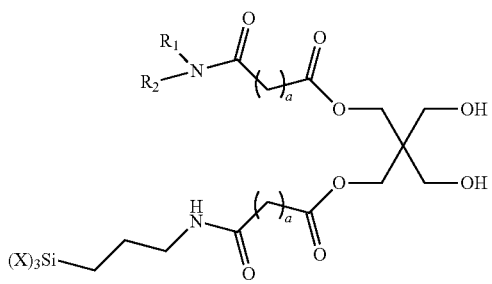

by reacting the compound 13 with a constructional formula

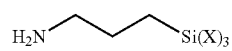

with the compound 8 and N,N'-dicyclohexylcarbodiimide in aprotic organic solvent under 25-40° C. for 24-36 h, wherein the molar ratio between the compound 8, N,N'-dicyclohexylcarbodiimide and the compound 13 is 1:1-2:1.1-1.5, and X is ethoxy or methoxy;

3) forming a hybrid lipid compound with a constructional formula

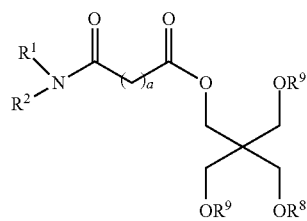

by reacting the compound 28 with deacid reagent, 4-dimethylaminopyridine and the compound 4 in aprotic organic solvent under 25-70° C. for 24-48 h, following washing in turn with acidic water and water, then purifying through column chromatography, wherein $R^9$ is —$CO(CH_2)_2COOH$ or —$CO(CH_2)_3COOH$, $R^8$ is —$CO(CH_2)_2CONH(CH_2)_3Si(X)_3$ or —$CO(CH_2)_3CONH(CH_2)_3Si(X)_3$, in which X is ethoxy or methoxy, a is 2 or 3, and the molar ratio of compound 28, 4-dimethylaminopyridine, the deacid reagent and the compound 4 is 1:0.4-1:1-6:4-8.

Wherein, in step "3)", the molar ratio of the compound 28, DMAP, the deacid agent and the compound 4 is 1:0.4-0.6:3-5:5-7.

In particular, the polar organic solvent is one among the group consisting of tetrahydrofuran, acetone, dimethylformamide and acetonitrile; the aprotic organic solvent is one among the group consisting of Benzene, toluene, Dichloromethane, chloroform, DMSO and DMF; the deacid agent is triethylamine or pyridine.

Wherein, $R^1$ is one among the group consisting of hexyl, octyl, undecyl, dodecyl, tridecyl, tetradecyl, fifteen alkyl, hexadecyl, seventeen alkyl and octadecyl; $R^2$ is one among the group consisting of hexyl, octyl, undecyl, dodecyl, tridecyl, tetradecyl, fifteen alkyl, hexadecyl, seventeen alkyl and octadecyl.

Another aspect of the present invention is to provide the cerasome self-assembly from the above hybrid lipids based on pentaerythritol by sol-gel reaction.

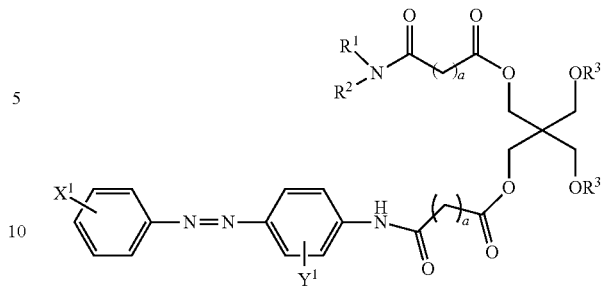

Wherein:
$R^1$ is $C_6$-$C_{18}$ alkyl, $R^2$ is $C_6$-$C_{18}$ alkyl, $R^3$ is one among the group consisting of —$CO(CH_2)_2CONH(CH_2)_3Si(X)_3$, —$CO(CH_2)_3CONH(CH_2)_3Si(X)_3$ and —$CONH(CH_2)_3Si(X)_3$, in which X is ethoxy or methoxy, a is 2 or 3, $X^1$ is one among the group consisting of —H, —$CH_3$, $CH_3O$—, halogenated group and —$NO_2$; $Y^1$ is one among the group consisting of —H, —$CH_3$, $CH_3O$— and halogenated group.

Another aspect of the present invention provides use of hybrid lipid compound based on pentaerythritol, wherein the cerasome derived from the hybrid lipid compound is used as drug or drug carrier for inflammatory diseases, neurological diseases, atherosclerosis and cancer treatment, the hybrid lipid compound with a constructional formula

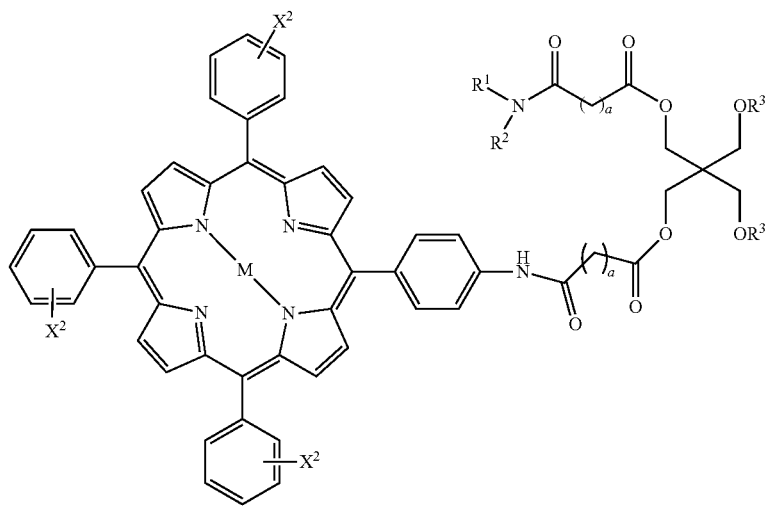

Wherein any cerasome derived from the hybrid lipid compounds based on pentaerythritol, have a silicate network surface.

Another aspect of the present invention provides use of the hybrid lipid compound based on pentaerythritol as light-control materials for controlling drug release from the liposome, the hybrid lipid compound with a constructional formula Wherein $R^1$ is $C_6$-$C_{18}$ alkyl, $R^2$ is $C_6$-$C_{18}$ alkyl, $R^3$ is one among the group consisting of —$CO(CH_2)_2CONH(CH_2)_3Si(X)_3$, —$CO(CH_2)_3CONH(CH_2)_3Si(X)_3$ and —$CONH(CH_2)_3Si(X)_3$, in which X is ethoxy or methoxy; $X^2$ is one among the group consisting of —H, —$CH_3$, $CH_3O$— and halogen; M is the metal ion coordinated with porphyrin ring.

Another aspect of the present invention provides use of hybrid lipid compound based on pentaerythritol, wherein the cerasome derived from the hybrid lipid compound is used as functional materials for optical storage and molecular devices, the hybrid lipid compound with a constructional formula

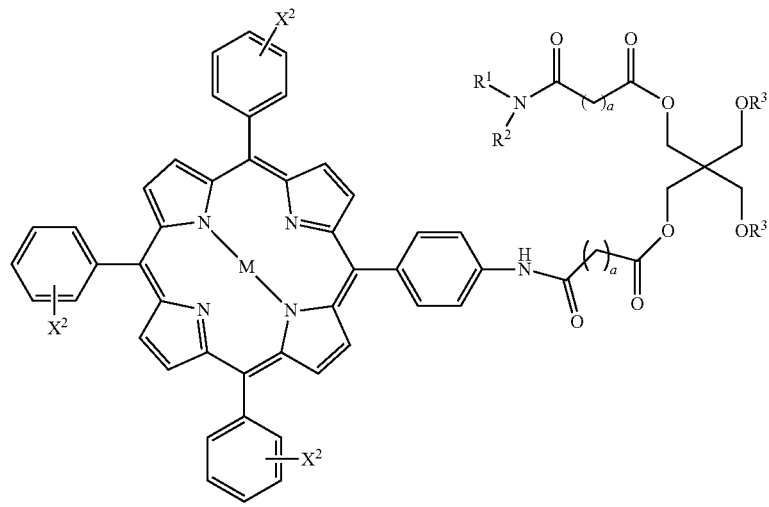

Wherein $R^1$ is $C_6$-$C_{18}$ alkyl, $R^2$ is $C_6$-$C_{18}$ alkyl, $R^3$ is one among the group consisting of —CO(CH$_2$)$_2$CONH (CH$_2$)$_3$Si(X)$_3$, O(CH$_2$)$_3$CONH(CH$_2$)$_3$Si(X)$_3$ and —CONH (CH$_2$)$_3$Si(X)$_3$, in which X is ethoxy or methoxy; $X^2$ is one among the group consisting of —H, —CH$_3$, CH$_3$O— and halogen; M is the metal ion coordinated with porphyrin ring.

Another aspect of the present invention provides use of hybrid lipid compound based on pentaerythritol, wherein the liposome derived from the hybrid lipid compound is used as functional materials for simulation design and synthesis of artificial systems, the hybrid lipid compound with a constructional formula

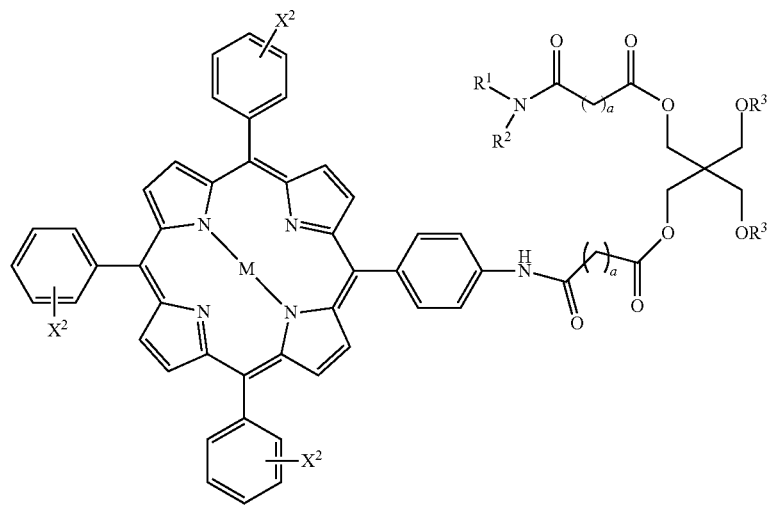

Wherein $R^1$ is $C_6$-$C_{18}$ alkyl, $R^2$ is $C_6$-$C_{18}$ alkyl, $R^3$ is one among the group consisting of —CO(CH$_2$)$_2$CONH(CH$_2$)$_3$Si (X)$_3$, —CO(CH$_2$)$_3$CONH(CH$_2$)$_3$Si(X)$_3$ and —CONH (CH$_2$)$_3$Si(X)$_3$, in which X is ethoxy or methoxy; $X^2$ is one among the group consisting of —H, —CH$_3$, CH$_3$O— and halogen; M is the metal ion coordinated with porphyrin ring.

Another aspect of the present invention provides use of hybrid lipid compound based on pentaerythritol as light-control materials for controlling drug release from liposome.

Another aspect of the present invention provides the use of hybrid lipid compound based on pentaerythritol, which is used for the preparation of Nano-composite membrane materials.

Another aspect of the present invention provides use of hybrid lipid compound based on pentaerythritol, which is used for the removal of organic pollutants in the environment.

To achieve the purpose of the present invention, another aspect of the present invention provides a hybrid lipid compound based on pentaerythritol with a constructional formula

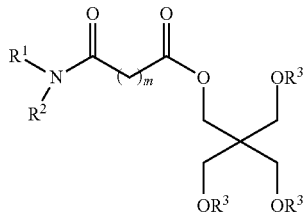

Wherein:

$R^1$ is $C_6$-$C_{18}$ alkyl, $R^2$ is $C_6$-$C_{18}$ alkyl, $R^3$ is one among the group consisting of $CO(CH_2)_m CONH(CH_2)_3 Si(X)_3$, $CO(CH_2)_5 N(CH_3)_2 (CH_2)_3 Si(X)_3 Y$ or $CONH(CH_2)_3 Si(X)_3$, in which m is 2 or 3, X is ethoxy or methoxy, Y is the halogenated group;

A method for making the above hybrid lipid compound comprises the following steps:

1) forming a compound 1 with a constructional formula

by reacting alkyl amines and alkyl bromide under heating reflux for 5 days, 2) forming a compound with a constructional formula

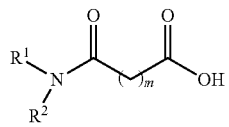

By reacting

with succinic anhydride or glutaric anhydride through nucleophilic reaction;

then forming a compound with a constructional formula

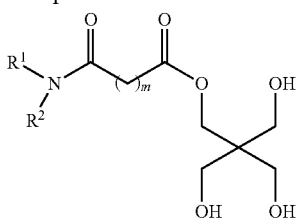

by reacting

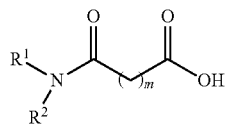

with excess 4 to 6 times of pentaerythritol through esterification reaction;

3) forming a hybrid lipid compound with a constructional formula

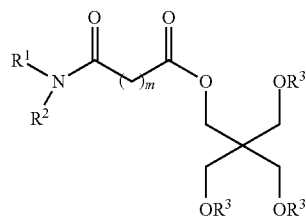

by reacting the

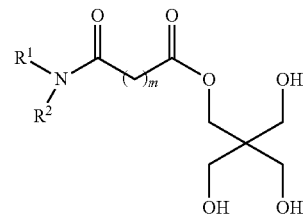

with 3-isocyanatopropyltriethoxysilane or 3-isocyanatopropyltrimethoxysilane through nucleophilic reaction for 2-3 days, wherein $R^3$ is —$CONH(CH_2)_3 Si(X)_3$—;

Or by reacting

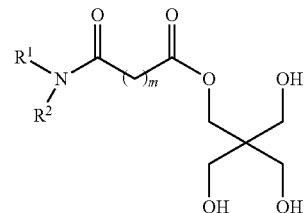

with 6-Bromohexanoyl chloride through esterification reaction, followed by reacting with dimethylamine gas saturated tetrahydrofuran solution through nucleophilic reaction, and then reacting with 3-Bromopropyltriethoxysilane or 3-Bromopropyltrimethoxysilane through nucleophilic reaction, wherein $R^3$ is —$CO(CH_2)_5 N(CH_3)_2 (CH_2)_3 Si(X)_3 Y$.

Or by reacting

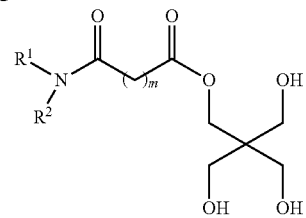

with succinic anhydride or glutaric anhydride through nucleophilic reaction, following reacting with 3-aminopropyltriethoxysilane or 3-aminopropyltrimethoxysilane through condensation reaction, wherein $R^3$ is —$CO(CH_2)_m CONH(CH_2)_3 Si(X)_3$.

Another aspect of the present invention provides a hybrid lipid compound based on pentaerythritol with a constructional formula

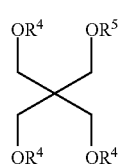

Wherein:

$R^4$ is $C_5$-$C_{18}$ alkyl, $R^5$ is one among the group consisting of $CONH(CH_2)_3Si(X)_3$, $CO(CH_2)_m CONH(CH_2)_3Si(X)_3$ and $CO(CH_2)_5N(CH_3)_2(CH_2)_3Si(X)_3Y$, in which m is 2 or 3, X is ethoxy or methoxy, Y is the halogenated group.

A method for making the above hybrid lipid compound comprises the following steps:

1) forming a compound with a constructional formula

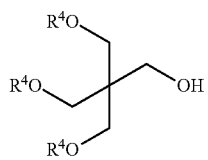

by reacting pentaerythritol and 3 times of alkyl bromide with a constructional formula of $R^4$—Br in alkaline conditions for 6 hours;

2) forming a hybrid lipid compound with a constructional formula

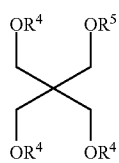

by reacting

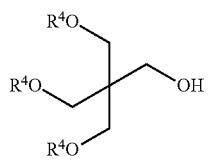

with 3-Isocyanatopropyltriethoxysilane or 3-Isocyanatopropyltrimethoxysilane for 2-3 days, wherein $R^5$ is —CONH$(CH_2)_3Si(X)_3$;

or by reacting

![structure]

with 6-Bromohexanoyl chloride through esterification reaction, following reacting with dimethylamine gas saturated tetrahydrofuran solution through nucleophilic reaction, and then reacting with 3-Bromopropyltriethoxysilane or 3-Bromopropyltrimethoxysilane through nucleophilic reaction, wherein $R^5$ is —$CO(CH_2)_5N(CH_3)_2(CH_2)_3Si(X)_3Y$;

or by reacting

![structure]

with succinic anhydride or glutaric anhydride through nucleophilic reaction, following reacting with 3-aminopropyltriethoxysilane or 3-aminopropyltrimethoxysilane through nucleophilic reaction wherein $R^5$ is —$CO(CH_2)_m CONH(CH_2)_3Si(X)_3$.

A hybrid lipid compound containing azobenzene unit based on pentaerythritol of the present invention with a constructional formula

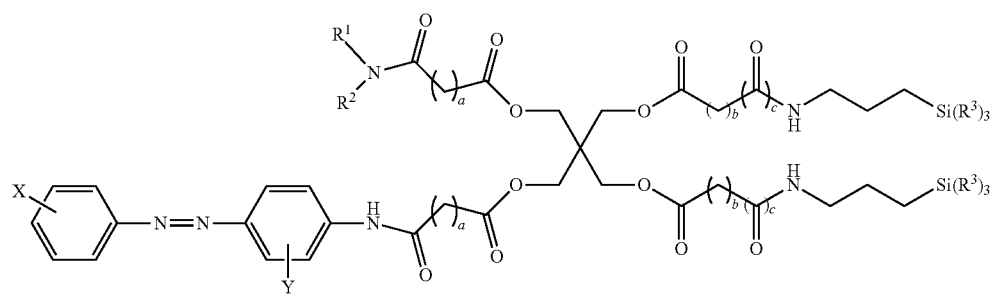

Wherein:

$R^1$ is $C_6$-$C_{18}$ alkyl, $R^2$ is $C_6$-$C_{18}$ alkyl, $R^1$ and $R^2$ can be the same or different, $R^3$ is OEt or $OCH_3$, a is 2 or 3; b is 2 or 3, c is 1, and c is 0 when b is 0, X is one among the group consisting of H, $CH_3$, $CH_3O$, F, Cl, Br and $NO_2$, Y is one among the group consisting of H, $CH_3$, $CH_3O$, F, Cl and Br, when Y is at the 2-position of amino group, it is H, $CH_3$ or $CH_3O$, when Y is at the 3-position of amino group, it is H, F, Cl or Br.

The synthesis route of the present invention is described according to the following scheme:

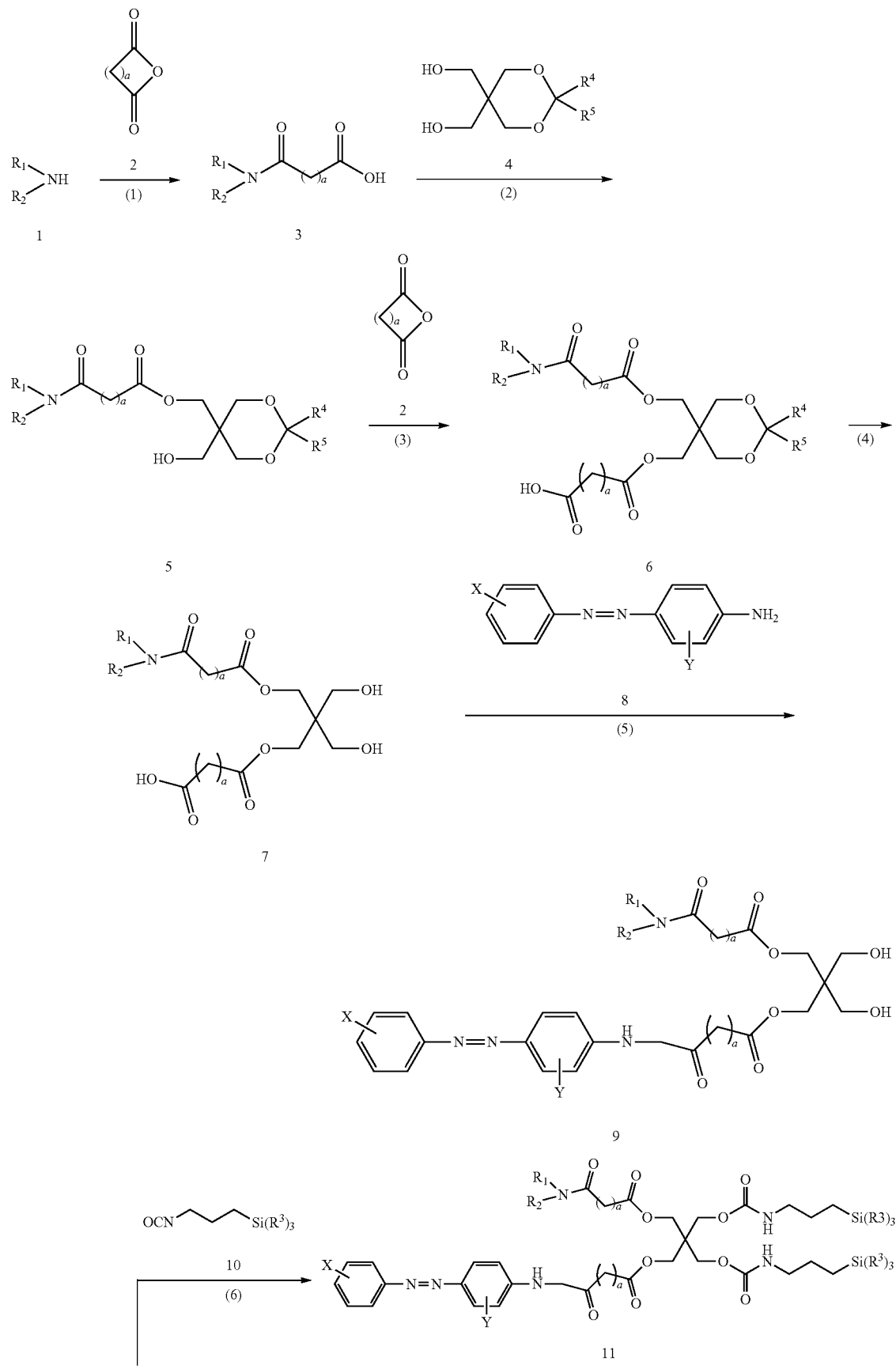

-continued

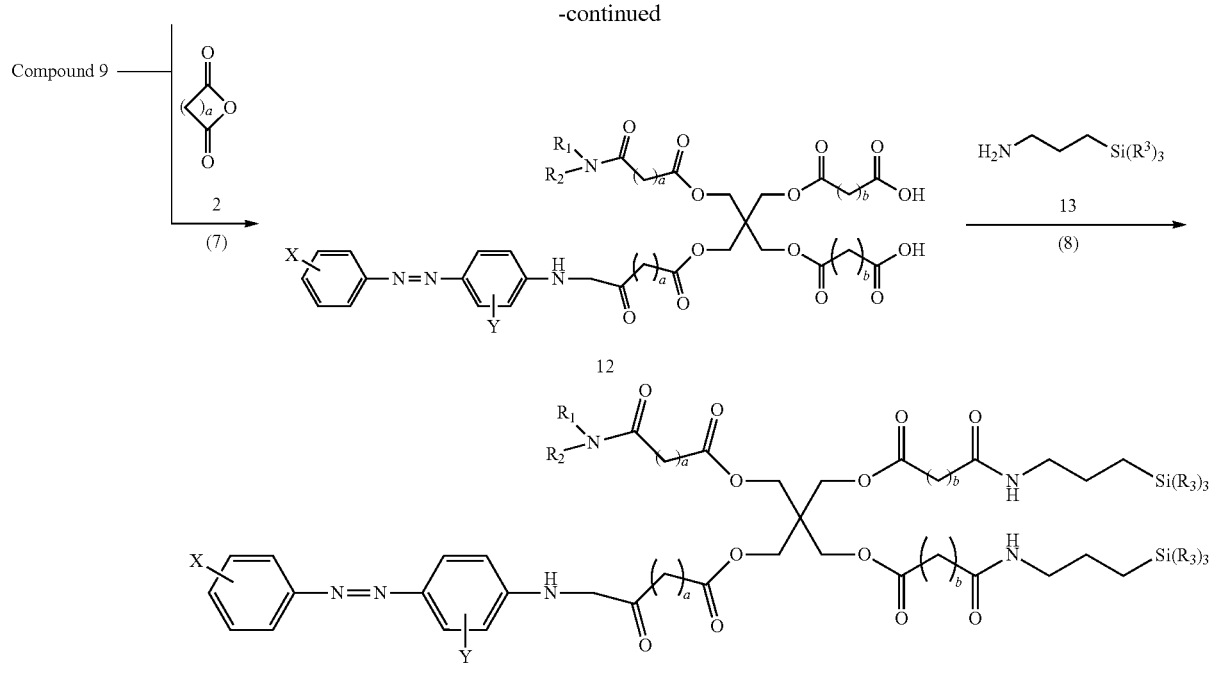

Wherein, $R^1$ is $C_6$-$C_{18}$ alkyl, $R^2$ is $C_6$-$C_{18}$ alkyl, $R^1$ and $R^2$ can be the same or different, $R^3$ is OEt or $OCH_3$, a is 2 or 3; b is 2 or 3, c is 1, and c is 0 when b is 0, When $R_4$ is Ph, then $R_5$ is H; When $R_4$ is $CH_3$, then $R_5$ is $CH_3$; X is one among the group consisting of H, $CH_3$, $CH_3O$, F, Cl, Br and $NO_2$, Y one among the group consisting of H, $CH_3$, $CH_3O$, F, Cl and Br; when Y is at the 2-position of amino group, it is one among H, $CH_3$ and $CH_3O$, when Y is at the 3-position of amino group, it is one among H, F, Cl and Br.

The synthesis of the compound 1 is described in the publication (*J. Am. Chem. Soc.* 118, 8524-8530, 1996), the synthesis of the compound 4 is described in the publication (Chinese organic chemistry, 2005, 9, 1049-1052), and the synthesis of the compound 8 is described in the publication (*Journal of Qingdao University of Science and Technology.* 2008, 29(2), 110-113).

The process of the present invention comprises:

(1) In polar organic solvent, by reacting a compound 1 and a compound 2 at 25-70° C. for 24-48 hours, following washing in turn with acidic water and water, and recrystalling to obtain a compound 3. The molar ratio of the compound 1 to the compound 2 is 1:1.5-4, the preferred ratio is 1:2-2.5, and the said polar organic solvents can be tetrahydrofuran, acetone, acetonitrile, dimethylformamide, etc.

(2) In polar organic solvent, by reacting the compound 3, DCC, DMAP and a compound 4 at 50-80° C. for 12-36 hours to obtain a compound 5. The molar ratio of the compound 3, DCC, DMAP and the compound 4 is 1:1-3:0.8-1.2: 3-6, the preferred molar ratio is 1:1.5-2:0.9-1.1:4-5, and the said polar organic solvents can be tetrahydrofuran, acetone, acetonitrile, dimethyl formamide, etc.

(3) In aprotic organic solvent, by reacting the compound 5, DMAP, deacid agent and the compound 2 at 25-70° C. for 24-48 hours, following washing in turn with acidic water and water, then purifying by column chromatography to obtain a compound 6. The molar ratio of the compound 5, DMAP, the deacid agent and the compound 2 is 1:0.4-1:1-6:2-5, the preferred ratio is 1:0.4-0.6:3-5:3-4, and the said aprotic organic solvent can be benzene, toluene, methylene chloride, chloroform, the deacid agent is triethylamine or pyridine, etc.

(4) In a mixed solvent of tetrahydrofuran and methanol or ethanol, by reacting the compound 6 and hydrogen in the presence of the catalyst at 25-80° C. for 12-48 hours to obtain a compound 7. The mass ratio of the compound 6 to the catalyst is 1:0.4-0.6, hydrogen pressure is 1.0-1.2 MPa, volume ratio of mixed solvent of tetrahydrofuran to methanol or ethanol is 3-4:1, and the catalyst is Pd/C or hydroxide palladium/carbon.

(5) In aprotic organic solvent, by reacting the compound 7, DCC and a compound 8 at 25-45° C. for 24-60 hour to obtain a compound 9. The molar ratio of the compound 7, DCC and the compound 8 is 1:1.2-1.5:1.1-2. The aprotic organic solvent can be benzene, toluene, methylene chloride, chloroform and so on.

(6) In aprotic organic solvents, by reacting the compound 9, a compound 10 and dibutyltin dilaurate at 40-70° C. for 48-72 hours to obtain a compound 11. The molar ratio of the compound 9, the compound 10 and dibutyltin dilaurate is 1:2-4: 0.2-0.8, the preferred molar ratio is 1:2-2.5:0.3-0.5, and the aprotic organic solvent can be benzene, toluene, methylene chloride, chloroform, etc.

(7) In aprotic organic solvents, by reacting the compound 9, DMAP, deacid agent and the compound 2 at 25-70° C. for 24-48 hours, following washing in turn with acidic water and water, then purifying by column chromatography to obtain a compound 12. The molar ratio of the compound 9, DMAP, deacid agent and the compound 2 is 1:0.8-2:3-8:4-8, and the preferred molar ratio is 1:1-1.5:5-6:6-7. The aprotic organic solvent can be benzene, toluene, methylene chloride, chloroform, etc., and the deacid agent can be triethylamine or pyridine, etc.

(8) In aprotic organic solvent, by reacting the compound 12, DCC and a compound 13 at 25-40° C. for 24-36 hours to obtain a compound 14. The molar ratio of the compound 12, DCC and the compound 13 is 1:1-2:1.5-2.0. The aprotic organic solvents can be benzene, toluene, methylene chloride, chloroform, etc.

A hybrid lipid compound containing cholesterol unit based on pentaerythritol of the present invention with a constructional formula

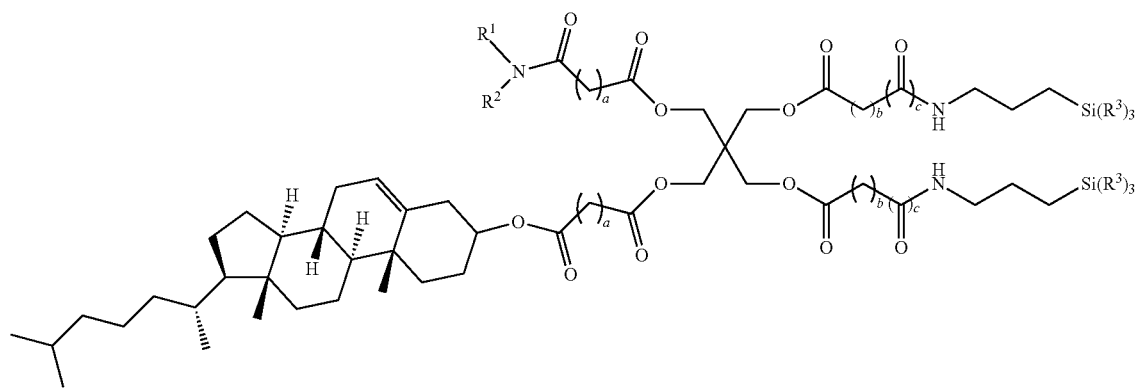

Wherein:
$R^1$ is $C_6$-$C_{15}$ alkyl, $R^2$ is $C_6$-$C_{18}$ alkyl, $R^1$ and $R^2$ can be the same or different, $R^3$ is OEt or $OCH_3$, a is 2 or 3; b is 2 or 3, c is 1, and c is 0 when b is 0.

The synthesis route of the present invention is described according to the following scheme:

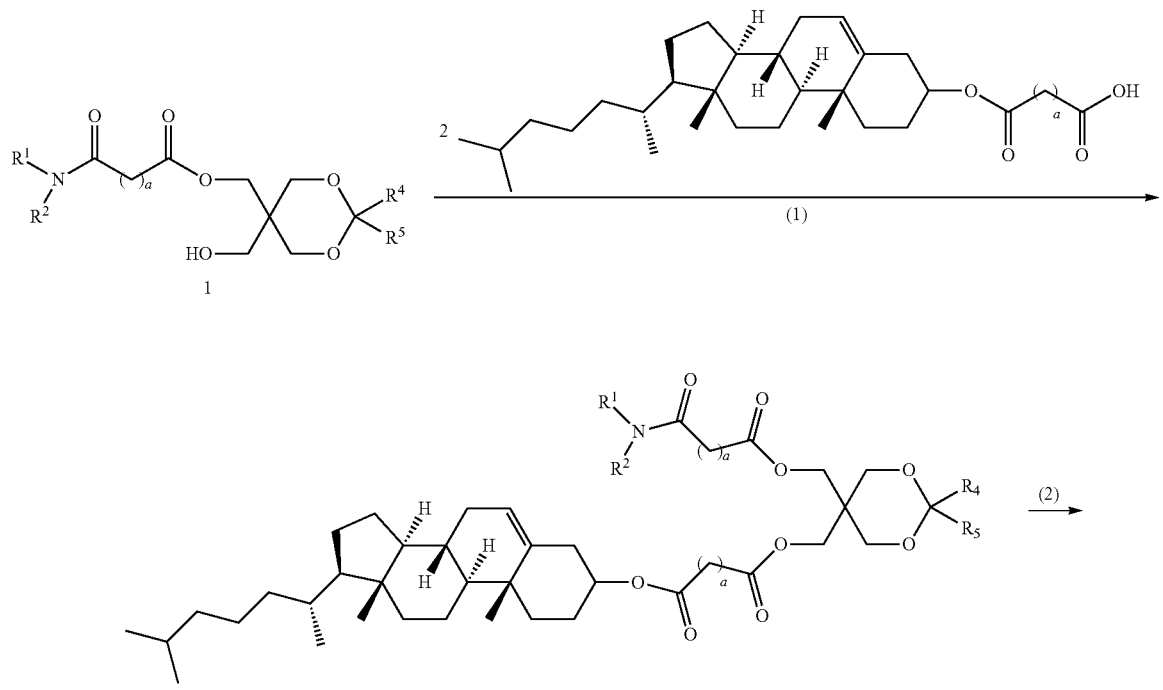

-continued
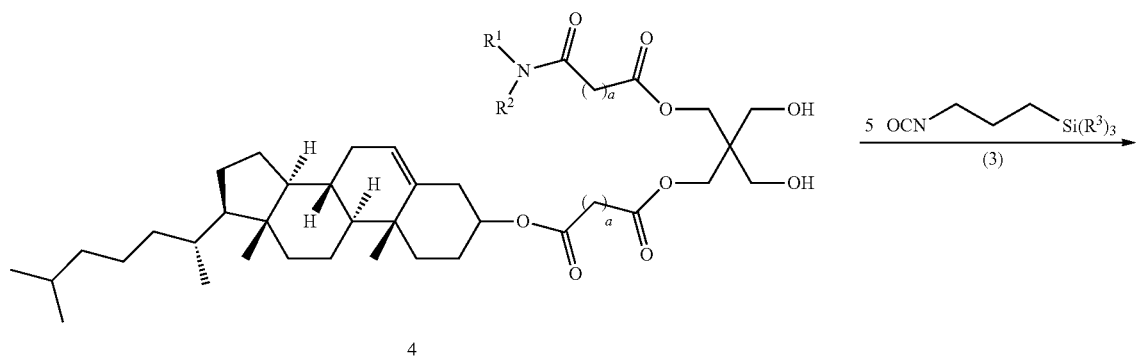
4
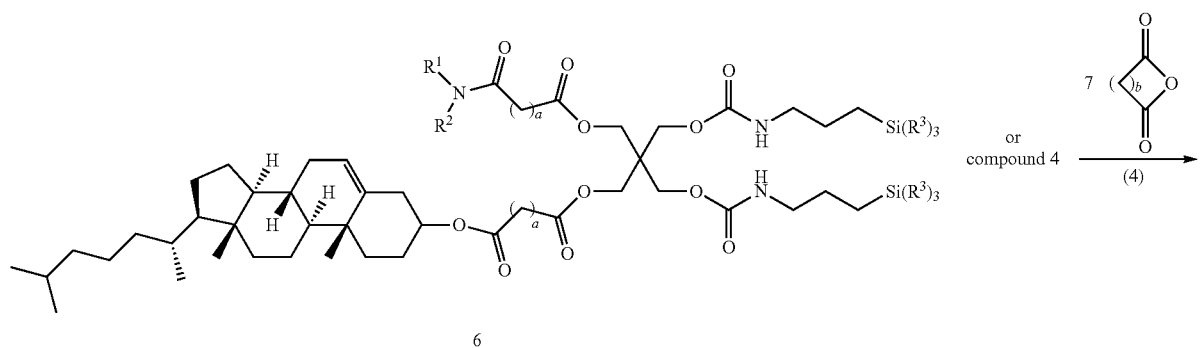
6
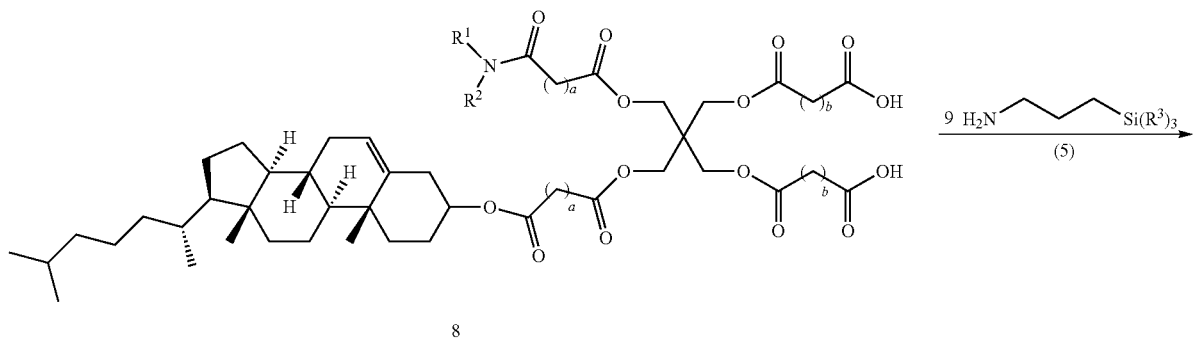
8
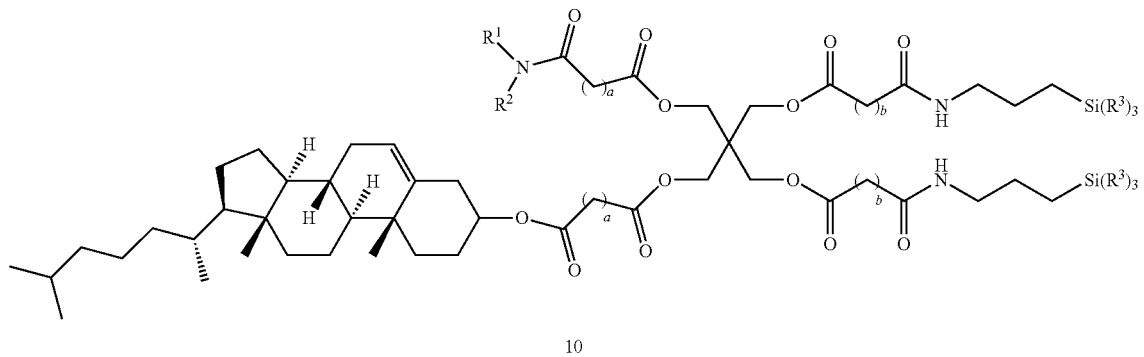
10 wherein
$R^1$ is $C_6$-$C_{18}$ alkyl, $R^2$ is $C_6$-$C_{18}$ alkyl, $R^1$, $R^2$ can be the same or different, $R^3$ is OEt or OCH$_3$, a is 2 or 3; b is 2 or 3, c is 1, and c is 0 when b is 0.

The synthesis of the compound 1 is described in the applied patent application (application number: 200910073423.5), the synthesis of the compound 2 is described in the publication (*Carbohydrate Polymers* 2006, 65, 337-345; *European Polymer Journal* 2008, 44, 55-565).

The process of the present invention comprises:

(1) In the polar organic solvent, by reacting a compound 1, DCC, DMAP and a compound 2 at 50-80° C. for 12-36 hours to obtain a compound 3. The molar ratio of the compound 1, DCC, DMAP and the compound 2 is 1:1-3:0.8-1.2:1-3, and the preferred molar ratio is 1:1.5-2:0.9-1.1:1.2-2.5. The polar organic solvents can be tetrahydrofuran, acetone, acetonitrile, dimethyl formamide, etc.

(2) in a mixed solvent of tetrahydrofuran and methanol or ethanol, by reacting the compound 3, hydrogen in the presence of catalyst at 25-80° C. for 12-48 hours to obtain a compound 4. The mass ratio of the compound 3 to the catalyst is 1:0.4-0.6, hydrogen pressure is 1.0-1.2 MPa, the volume ratio of mixed solvent of tetrahydrofuran and methanol or ethanol is 3-4:1, and the catalyst is Pd/C or hydroxide palladium/carbon.

(3) In aprotic organic solvent, by reacting the compound 4, a compound 5 and dibutyltin dilaurate at 40-70° C. for 48-72 hours to obtain a compound 6. The molar ratio of the compound 4, the compound 5 and dibutyltin dilaurate is 1:2-4: 0.2-0.8, the preferred molar ratio is 1:2-2.5:0.3-0.5, and the aprotic organic solvent can be benzene, toluene, methylene chloride, chloroform, etc.

(4) In aprotic organic solvent, by reacting the compound 4, DMAP, deacid agent and a compound 7 at 25-70° C. for 24-48 hours, following washing in turn with acidic water and water, then purifying by column chromatography to obtain a compound 8. The molar ratio of the compound 4, DMAP, deacid agent and the compound 7 is 1:0.8-2:3-8:4-8, and the preferred molar ratio is 1:1-1.5:5-6:6-7. The aprotic organic solvent can be benzene, toluene, methylene chloride, chloroform, etc, and the deacid agent can be triethylamine or pyridine, etc.

(5) In aprotic organic solvent, by reacting the compound 8, DCC and a compound 9 at 25-40° C. for 24-36 hours to obtain a compound 10. The molar ratio of the compound 8, DCC and the compound 9 is 1:1-2:2.0-2.5. The aprotic organic solvent can be benzene, toluene, methylene chloride, chloroform, etc.

A hybrid lipid compound containing porphyrin unit based on pentaerythritol of the present invention with a constructional formula

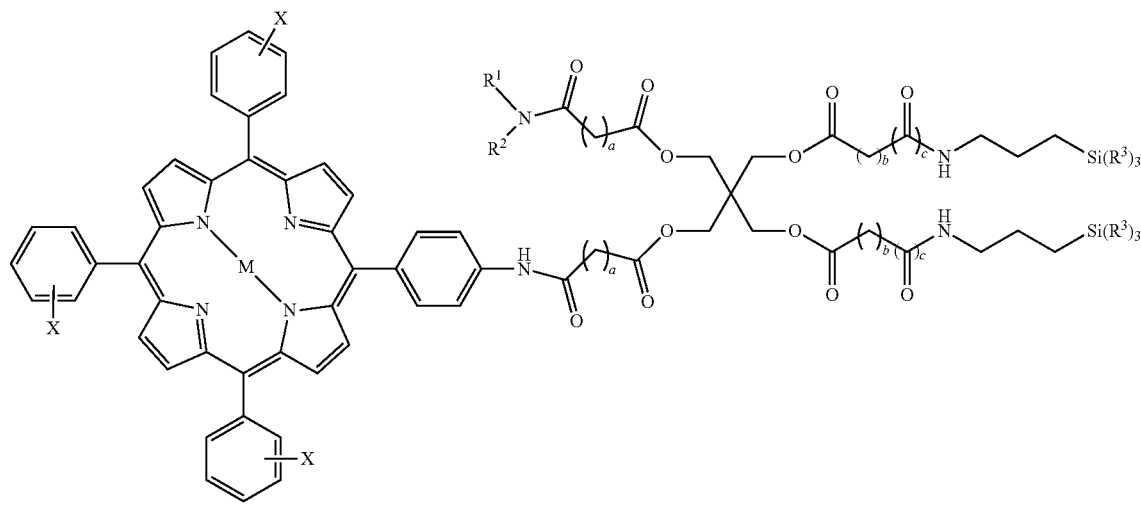

Wherein:
$R^1$ is $C_6$-$C_{18}$ alkyl, $R^2$ is $C_6$-$C_{18}$ alkyl, $R^1$ and $R^2$ can be the same or different, $R^3$ is OEt or OCH$_3$, a is 2 or 3; b is 2 or 3, c is 1, and c is 0 when b is 0, X is one among the group consisting of H, CH$_3$, CH$_3$O, halogen, M represents two hydrogen or all the metals ion coordinated with porphyrin ring, such as iron (Fe), Zinc (Zn), Magnesium (Mg), Manganese (Mn), Cobalt (Co), Copper (Cu), Molybdenum (Mo), Chromium (Cr), Gadolinium (Gd), Iridium (Ir).

The synthesis route of the present invention is described according to the following scheme:

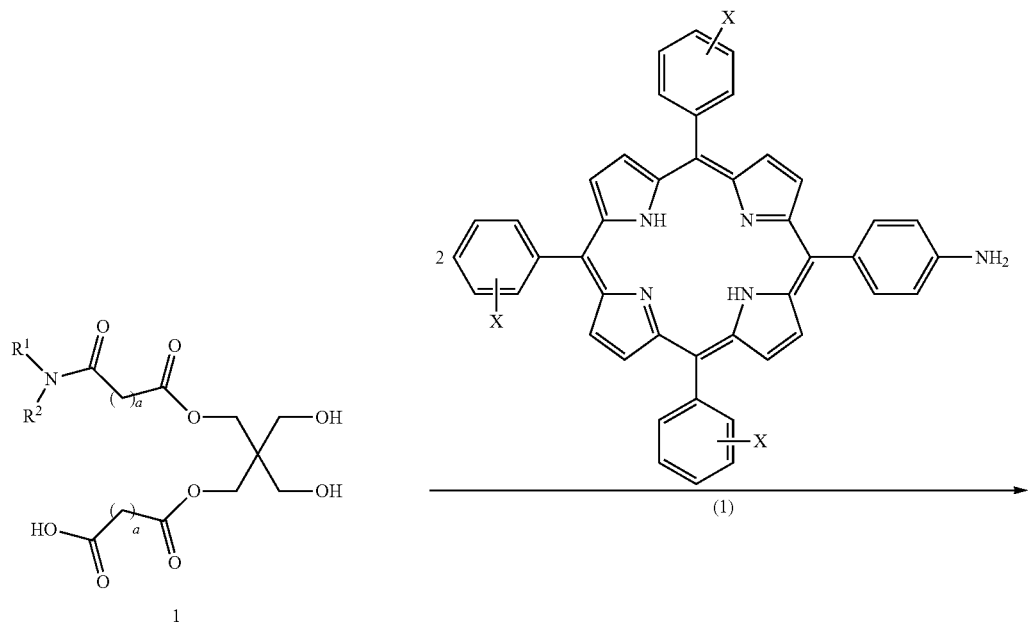
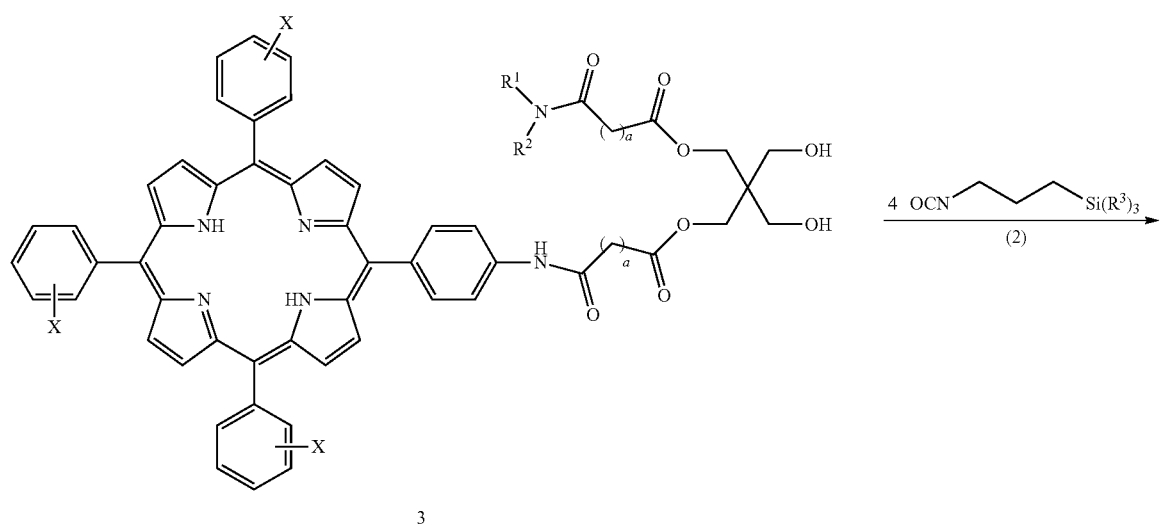
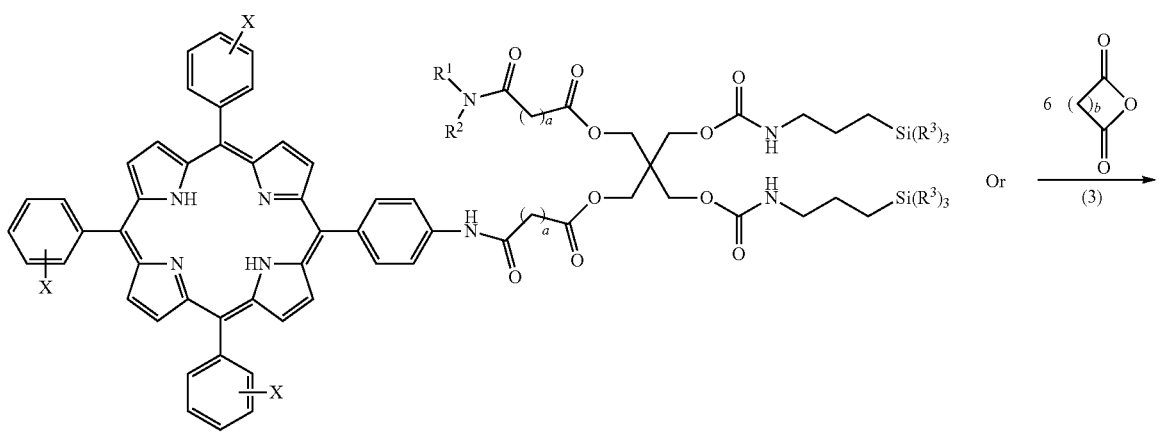

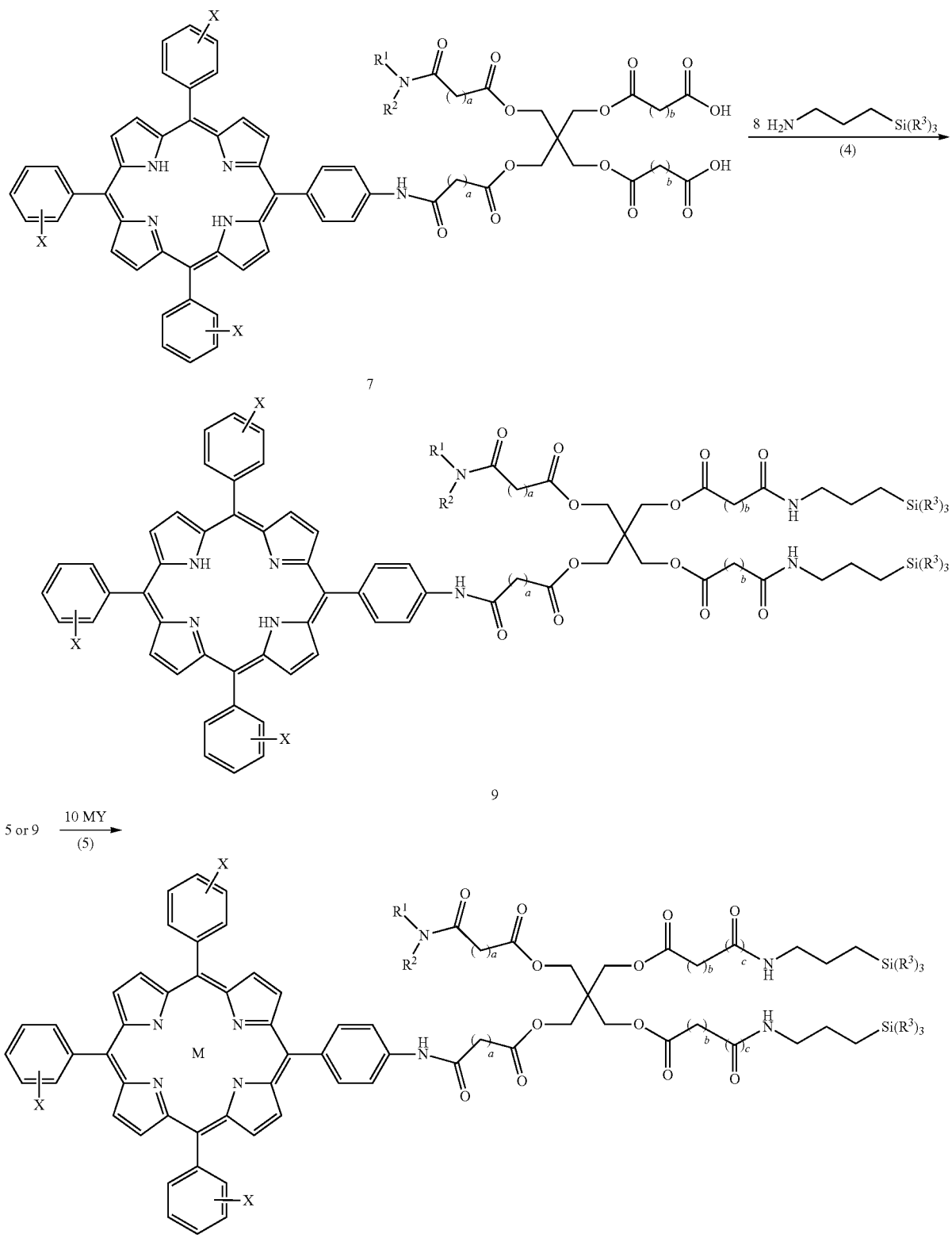
Wherein, $R^1$ is $C_6$-$C_{18}$ alkyl, $R^2$ is $C_6$-$C_{18}$ alkyl, $R^1$ and $R^2$ can be the same or different, $R^3$ is OEt or $OCH_3$, a is 2 or 3; b is 2 or 3, c is 1, and c is 0 when b is 0, X is one among the group consisting of H, $CH_3$, $CH_3O$, halogen, M represents two hydrogen or all the metals ion coordinated with porphyrin ring, such as iron (Fe), Zinc (Zn), Magnesium (Mg), Manganese (Mn), Cobalt (Co), Copper (Cu), Molybdenum (Mo), Chromium (Cr), Gadolinium (Gd), Iridium (Ir). Y is the anion formed metal salts with M, and the anion is halogen anion or acetate ions.

The synthesis method of the compound 1 is described in the applied patent application (application number: 200910073423.5). The synthesis method of the compound 2 is described in the publication (*Chemical Reagents*, 1994, 16(2), 105-106; *Tetrahedron* 2004, 60, 2757-2763).

The process of the present invention comprises:
(1) In aprotic organic solvent, by reacting a compound 1, DCC and a compound 2 at 25-45° C. for 24-72 hours to yield a compound 3. The molar ratio of the compound 1, DCC and the compound 2 is 1:1.2-1.5:1.1-2. The aprotic organic solvents can be benzene, toluene, methylene chloride, chloroform, DMSO or DMF, etc.
(2) In aprotic organic solvent, by reacting the compound 3, a compound 4 and dibutyltin dilaurate at 40-80° C. for 36-72 hours to afford a compound 5. The molar ratio of the compound 3, the compound 4 and dibutyltin dilaurate is 1: 2-5: 0.2-1.0, and the preferred molar ratio is 1:2-3:0.3-0.6. The aprotic organic solvents can be benzene, toluene, methylene chloride, chloroform, etc.
(3) In aprotic organic solvent, by reacting the compound 3, DMAP, deacid agent and a compound 6 at 25-75° C. for 24-48 hours, following washing in turn with acidic water and water, then purifying by column chromatography to afford a compound 7. The molar ratio of the compound 3, DMAP, the deacid agent and the compound 6 is 1:0.8-2:3-9:3-10, and the preferred molar ratio is 1:1-1.5:5-6:5-8. The aprotic organic solvent can be benzene, toluene, methylene chloride, chloroform, and the deacid agent can be triethylamine or pyridine, etc.
(4) In aprotic organic solvent, by reacting the compound 7, DCC and a compound 8 at 25-45° C. for 24-48 hours to yield a compound 9. The molar ratio of the compound 7, DCC and the compound 8 is 1:1-2:1.5-2.0. The aprotic organic solvents can be benzene, toluene, methylene chloride, chloroform and so on.
(5) In organic solvent, by reacting the compound 5 or the compound 9 with a compound 10 at 25-180° C. for 2-48 hours, then removing reaction solvent in vacuum and washing with water, the crude product was purified by column chromatography to afford a compound 11. The molar ratio of the compound 5 or the compound 9 to the compound 10 is 1:5-25, and the preferred molar ratio is 1:10-15. The preferred temperature is the boiling point of the corresponding organic solvent. The organic solvent can be DMSO, DMF, methanol, ethanol, dichloromethane, chloroform, etc.

A hybrid lipid containing benzene unit based on pentaerythritol of the present invention with a constructional formula

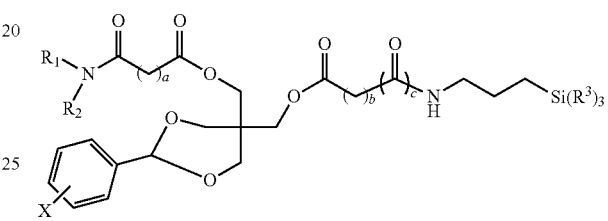

Wherein:
$R^1$ is $C_6$-$C_{18}$ alkyl, $R^2$ is $C_6$-$C_{18}$ alkyl, $R^1$ and $R^2$ can be the same or different, $R^3$ is OEt or $OCH_3$, a is 2 or 3; b is 2 or 3, c is 1, and c is 0 when b is 0, X is one among the group consisting of H, $CH_3$, $CH_3O$, halogen and $NO_2$.

The synthesis of the hybrid lipid in the present invention is described according to the following scheme:

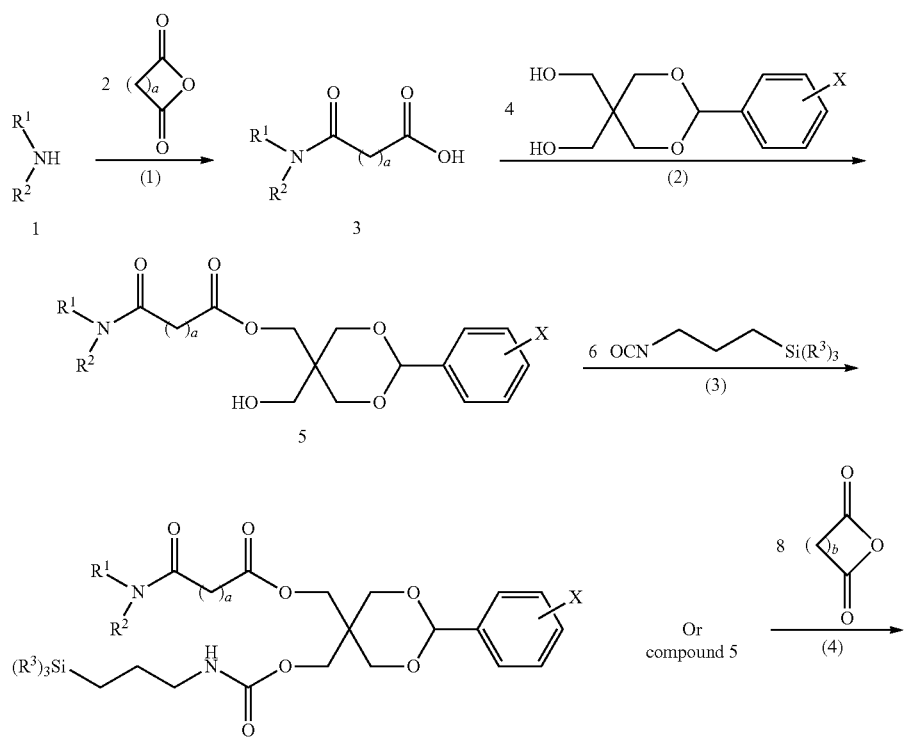

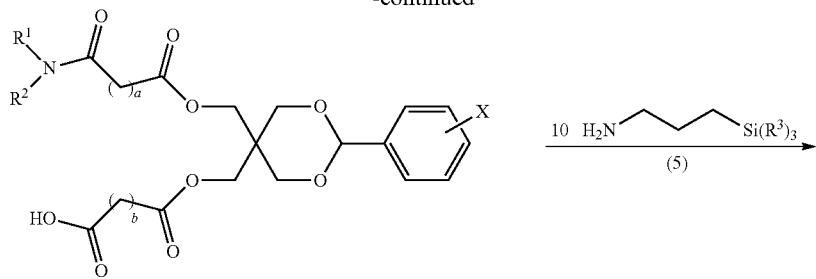

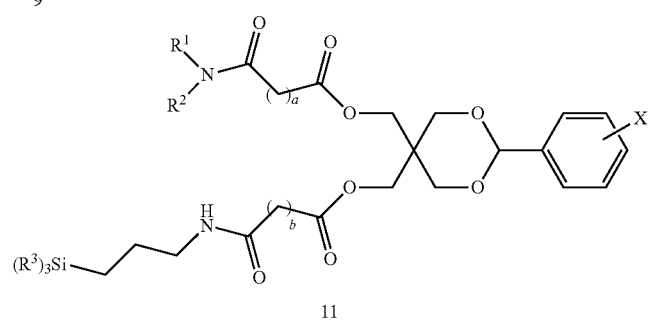

A hybrid lipid containing carboxyl unit based on pentaerythritol of the present invention with a constructional formula

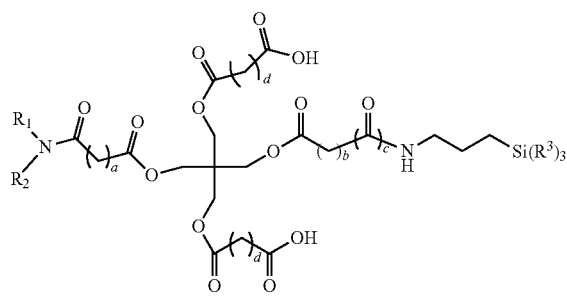

Wherein:

$R^1$ is $C_6$-$C_{18}$ alkyl, $R^2$ is $C_6$-$C_{18}$ alkyl, $R^1$ and $R^2$ can be the same or different, $R^3$ is OEt or $OCH_3$, a is 2 or 3; b is 2 or 3, c is 1, and c is 0 when b is 0, d is 2 or 3.

The synthesis of the hybrid lipid compound in the present invention is described according to the following scheme:

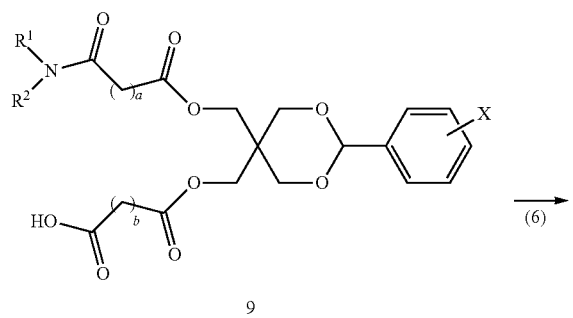

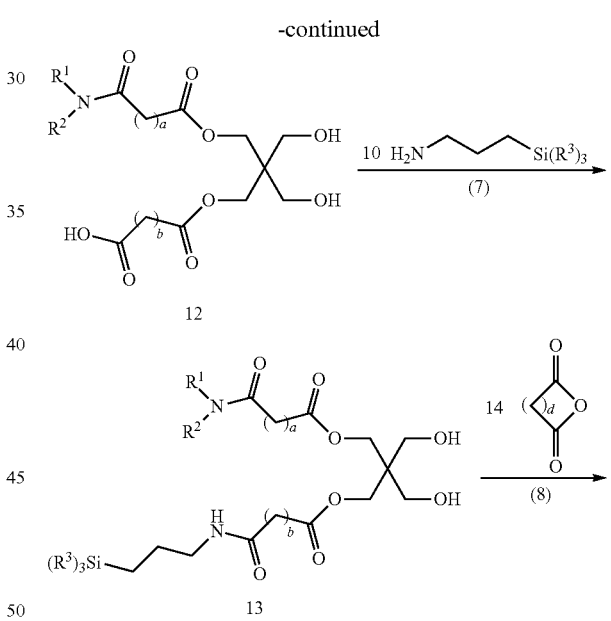

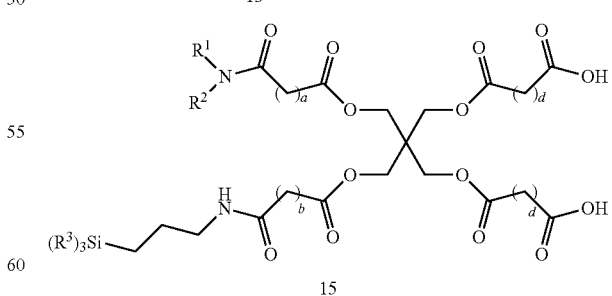

The synthesis of the compound 1 is described in the publication (*J. Am. Chem. Soc.* 118, 8524-8530, 1996), and the synthesis of the compound 4 is described in the publication (*Chinese organic chemistry*, 2005, 9, 1049-1052).

The process of the present invention comprises:

(1) In polar organic solvent, by reacting a compound 1 and a compound 2 at 25-70° C. for 24-48 hours, following washing in turn with acidic water and water, and then recrystallizing to obtain a compound 3. The molar ratio of the compound 1 and the compound 2 is 1:1.5-4, and the preferred molar ratio is 1:2-2.5. The polar organic solvent can be tetrahydrofuran, acetone, acetonitrile and dimethyl formamide, etc.

(2) In polar organic solvent, by reacting the compound 3, DCC, DMAP and a compound 4 at 50-80° C. for 12-36 hours to afford a compound 5. The molar ratio of the compound 3, DCC, DMAP and the compound 4 is 1:1-3:0.8-1.2:3-6, and the preferred molar ratio is 1:1.5-2:0.9-1.1:4-5. The polar organic solvents can be tetrahydrofuran, acetone, acetonitrile, dimethyl formamide, etc.

(3) In aprotic organic solvent, by reacting the compound 5, a compound 6 and dibutyltin dilaurate at 40-70° C. for 48-72 hours to obtain a compound 7. The molar ratio of the compound 5, the compound 6 and dibutyltin dilaurate is 1:1-2:0.2-0.8, and the preferred molar ratio is 1:1-1.25:0.3-0.5. The aprotic organic solvents can be benzene, toluene, methylene chloride, chloroform and so on.

(4) In aprotic organic solvent, by reacting the compound 5, DMAP, deacid agent and a compound 8 at 25-70° C. for 24-48 hours, following washing in turn with acidic water and water, and later purifying by column chromatography to afford a compound 9. The molar ratio of the compound 5, DMAP, deacid agent and the compound 8 is 1:0.4-1:1-6:2-5, and the preferred molar ratio is 1:0.4-0.6:3-5:3-4. The aprotic organic solvents can be one among benzene, toluene, methylene chloride, chloroform, and the deacid agent can be triethylamine or pyridine, etc.

(5) In aprotic organic solvent, by reacting the compound 9, DCC and a compound 10 at 25-40° C. for 24-36 hours to afford a compound 11. The molar ratio of the compound 9, DCC and the compound 10 is 1:1-2:1.1-1.5. The aprotic organic solvent can be benzene, toluene, methylene chloride, chloroform and so on.

(6) In mixed solvent of tetrahydrofuran and methanol or ethanol, by reacting the compound 9, hydrogen in the presence of a catalyst at 25-80° C. for 12-48 hours to yield a compound 12. The mass ratio of the compound 9 and the catalyst is 1:0.4-0.6, hydrogen pressure is 1.0-1.2 MPa, the volume ratio of mixed solvent of tetrahydrofuran and methanol or ethanol is 3-4:1, and the catalyst is Pd C or hydroxide palladium/carbon.

(7) In aprotic organic solvent, by reacting the compound 12, DCC and a compound 10 at 25-40° C. for 24-36 hours to afford a compound 13. The molar ratio of the compound 12, DCC and the compound 10 is 1:1-2:1.1-1.5. The aprotic organic solvent can be benzene, toluene, methylene chloride, chloroform and so on.

(8) In the aprotic organic solvent, by reacting the compound 13, DMAP, deacid agent and a compound 14 at 25-70° C. for 24-48 hours, following washing in turn with acidic water and water, and later purifying by column chromatography to afford a compound 15. The molar ratio of the compound 13, DMAP, deacid agent and the compound 14 is 1:0.4-1:1-6:4-8, and the preferred molar ratio is 1:0.4-0.6:3-5:5-7. The aprotic organic solvents can be benzene, toluene, methylene chloride, chloroform, and the deacid agent can be triethylamine or pyridine, etc.

Hybrid Lipid compounds of the present invention show the following advantages:

1. Hybrid Lipid compounds of the present invention can form liposomes (also known as cerasome) by hydrolysis and condensation, which have uniform size, a silicate network surface, and high stability. When surfactant Triton X-100 (TX-100) was added to the cerasome solution, size changes of cerasome were tested. Conventional liposomes made from phospholipids (DSPC) were used as controls under the same conditions to compare the stability of the cerasome. When 30 times amount of TX-100 solution were added, sizes of cerasome derived from the hybrid lipid of the present invention remained unchanged, while traditional liposomes from the DSPC decreased in sizes obviously in the presence of 5 times amount of TX-100. This indicates the vesicle structure has been destroyed, and provides strong evidence that cerasome derived from hybrid lipid compounds of the present invention shows higher stability than the conventional liposomes.

2. Hybrid lipid compounds of the present invention can form liposomes (also known as cerasomes) by hydrolysis and condensation reaction. The cerasomes derived from the hybrid lipid compounds can interact with the encapsulated hydrophobic or hydrophilic drugs via electronic conjugated attraction or electrostatic attraction, thereby enhancing drug encapsulation efficiency. The encapsulation rate can reach 95.4%-99.0%.

3. Cerasomes derived from the hybrid lipid compounds of the present invention have the surface of silicate network structure. Leakage of drugs is not easy.

4. The process and preparation method of the present invention is simple, raw materials are cheap, and reaction conditions are mild. The present invention has strong operational and clinical applications and promotes industrial production.

5. Cerasomes with silicate framework derived from the hybrid lipid compounds of the present invention are more stable than the existing liposomes, and can be used as carriers of the various types of drugs, dyes, quantum dots, magnetic nanoparticles and DNA, which show good prospects.

BRIEF DESCRIPTION OF THE DRAWINGS

FIG. 7 is the Fourier Transform infrared spectrum (FT-IR spectrum) of cerasome, wherein:

Figure 9:
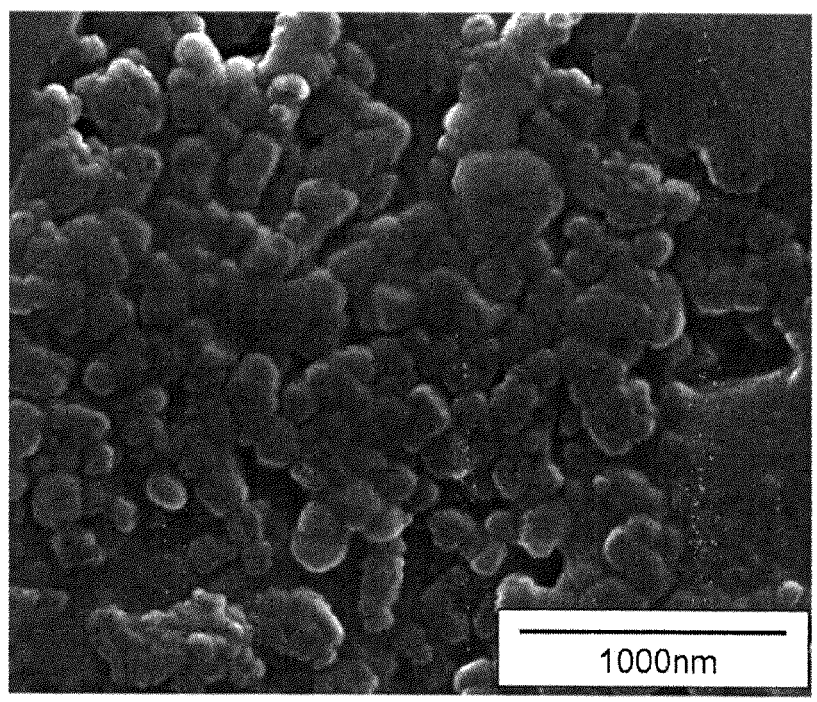
Figure 7:
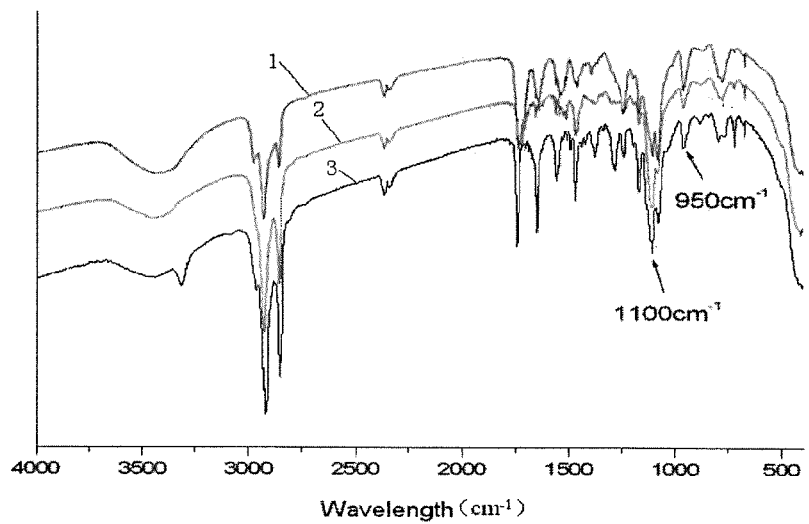
Figure 8:
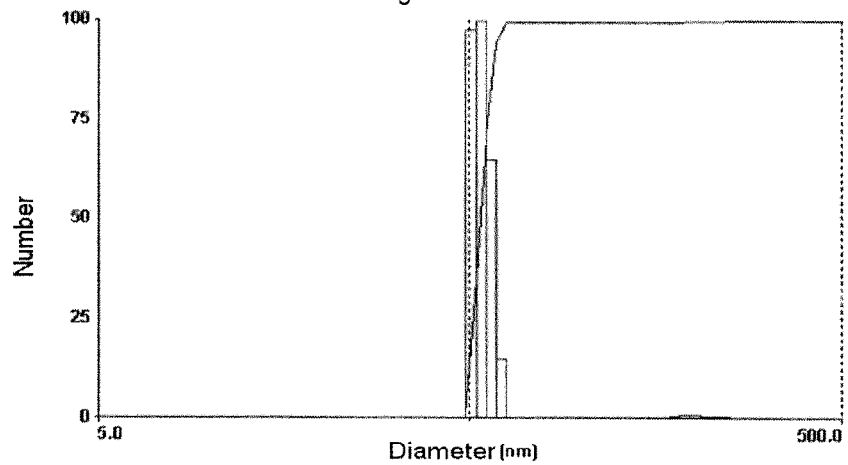
Figure 10:
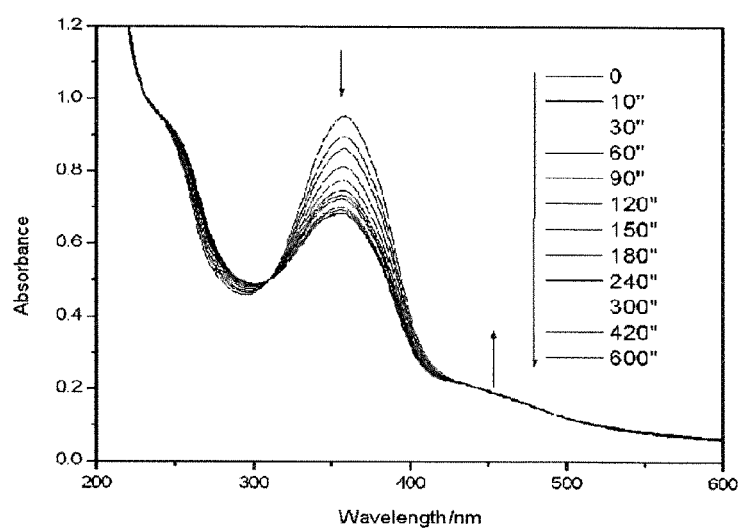
Figure 11:
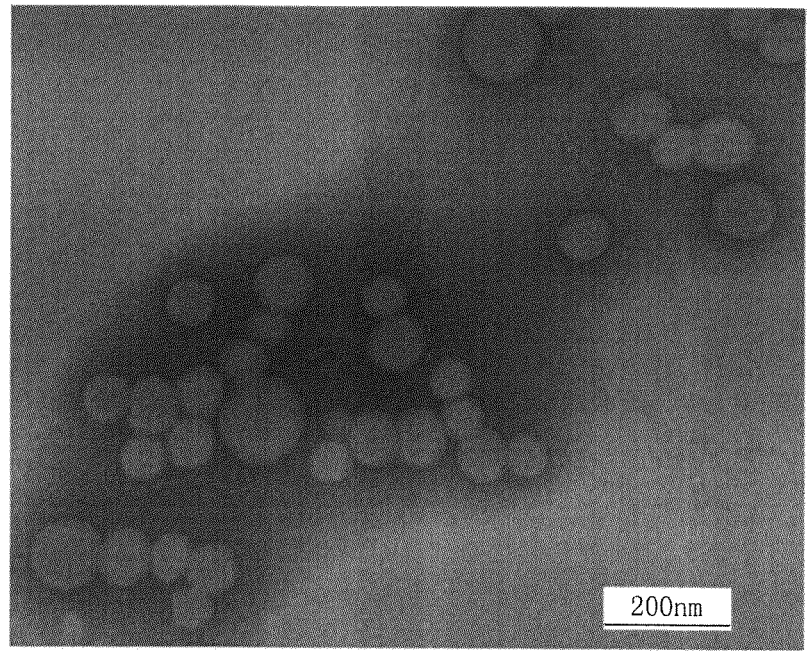
Figure 14:
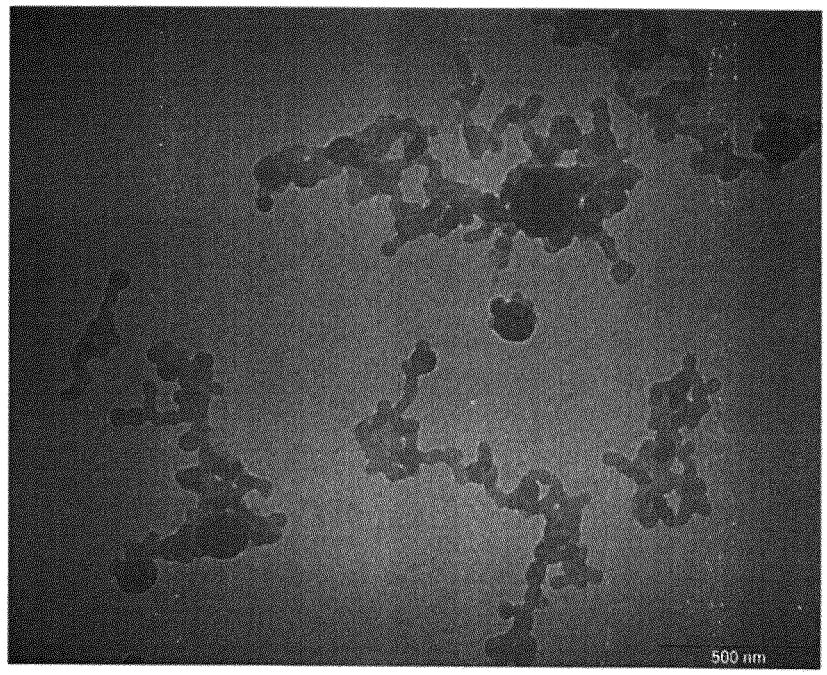
Figure 12:
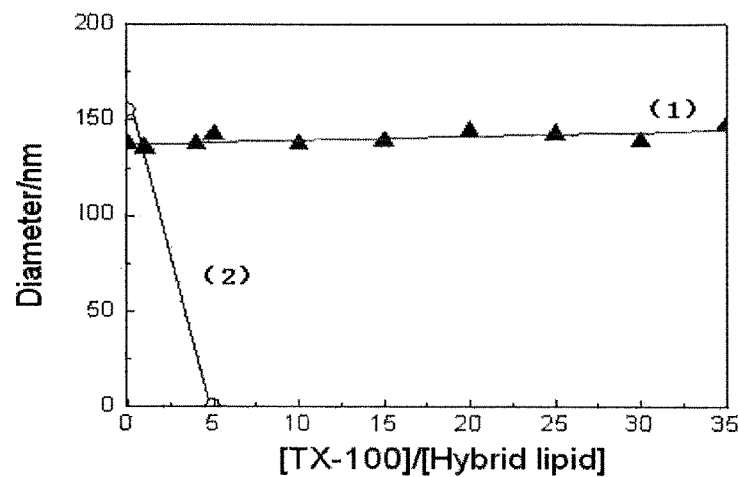
Figure 13:
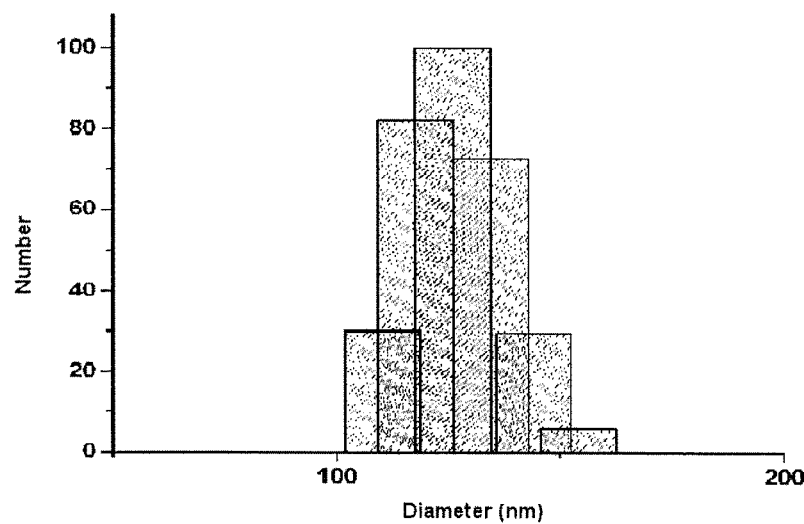
Figure 15:
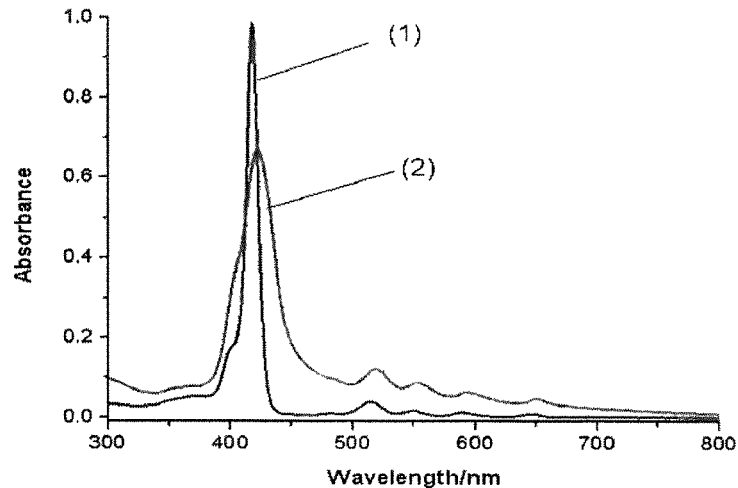
Figure 16:
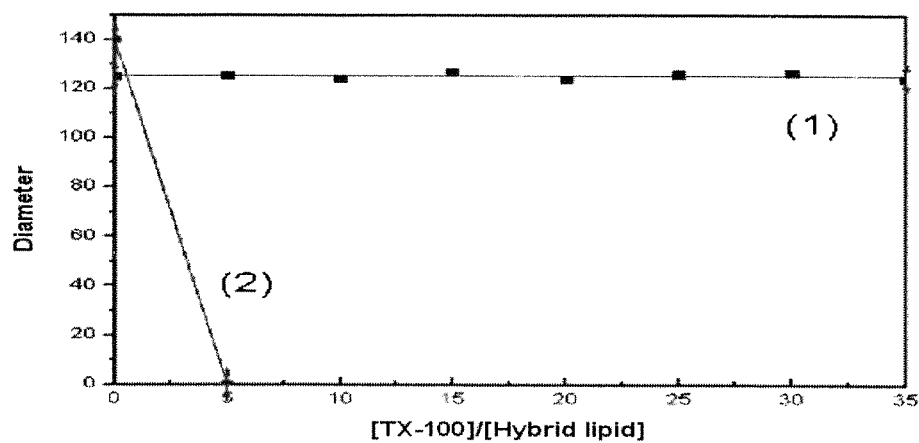
Figure 17:
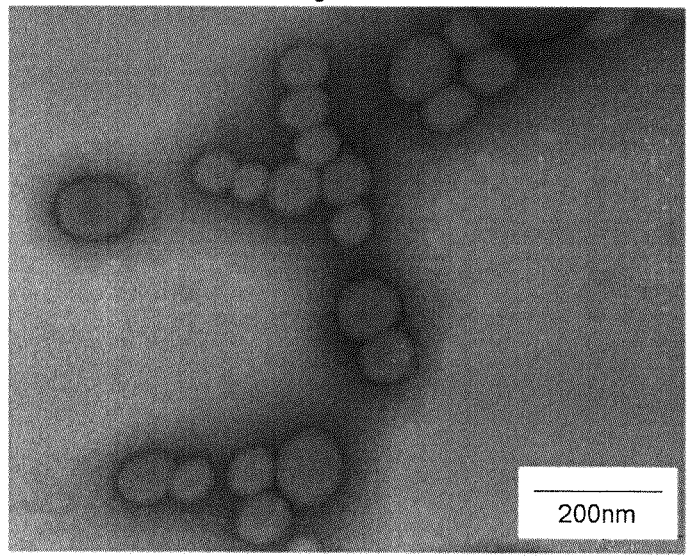
Figure 18:
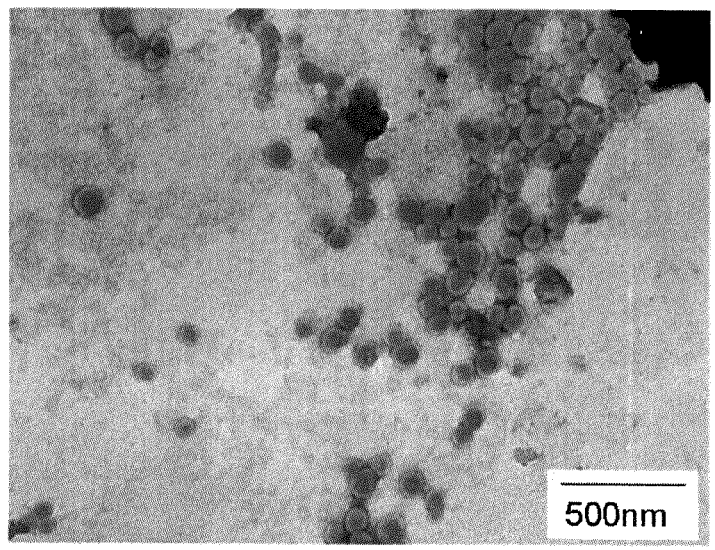

"1" presents FT-IR spectrum of cerasome 1 prepared in Embodiment 10;

"2" presents FT-IR spectrum of cerasome 2 prepared in Embodiment 18;

"3" presents FT-IR spectrum of cerasome 3 prepared in Embodiment 19;

FIG. 8 is the particle size distribution of cerasome prepared in Embodiment 31;

FIG. 9 is the scanning electron images (SEMs) of cerasome prepared in Embodiment 31;

FIG. 10 is the UV-visible absorption spectra of the liposome solution in embodiment 32 under 365 nm light irradiation;

FIG. 11 is the transmittance electron images (TEMs) of cerasome prepared in Embodiment 38;

FIG. 12 is the stability experiment of cerasome prepared in Embodiment 39, wherein:

(1) presents the Changes in particle size of cerasome in the presence of different times of Surfactant TX-100;
(2) presents the Changes in particle size of liposome prepared from DSPC in the presence of different times of Surfactant TX-100;

FIG. 13 is the Particle size distribution of cerasome prepared in Embodiment 46;

FIG. 14 is the transmittance electron images (TEMs) of cerasome prepared in Embodiment 46;

FIG. 15 is the UV-visible absorption spectra of cerasomes, wherein:
(1) presents the UV-visible absorption spectra of the Chloroform solution of compound 45 in embodiment 43,
(2) presents the UV-visible absorption spectra of the cerasome in embodiment 46;

FIG. 16 is the Particle size distribution of cerasome in the presence of different times of TX-100, wherein:
(1) presents the Changes in particle size of cerasome in embodiment 46 in the presence of different times of Surfactant TX-100;
(2) presents the Changes in particle size of liposome prepared from DSPC in embodiment 46 in the presence of different times of Surfactant TX-100;

FIG. 17 is the transmittance electron images (TEMs) of cerasome prepared in Embodiment 52;

FIG. 18 is the transmittance electron images (TEMs) of cerasome prepared in Embodiment 55.

DETAILED DESCRIPTION OF THE EMBODIMENTS

The following specific examples will help to understand the present invention, but do not limit the content of the present invention.

Example 1

The hybrid lipid compound based on pentaerythritol in this embodiment with a constructional formula

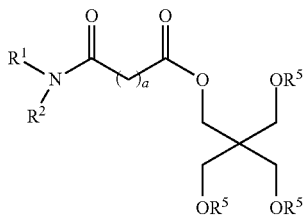

Wherein:
$R^1$ is $C_6$-$C_{18}$ alkyl, $R^2$ is $C_6$-$C_{18}$ alkyl, $R^5$ is one among the group consisting of —$CO(CH_2)_5N(CH_3)_2(CH_2)_3Si(X)_3Y$, —$CO(CH_2)_2CONH(CH_2)_3Si(X)_3$, —$CO(CH_2)_3CONH(CH_2)_3Si(X)_3$ and —$CONH(CH_2)_3Si(X)_3$, in which X is ethoxy or methoxy, Y is the halogenated group; a is 2 or 3.

The liposomes prepared from the hybrid lipid compound in this embodiment have uniform size, a silicate network surface and higher stability. When surfactant Triton X-100 (TX-100) was added to the liposomes solution, size changes of the liposomes were tested. Conventional liposomes made from phospholipids (DSPC) were used as controls under the same conditions to compare the stability of the cerasome. When 30 times amount of TX-100 solution were added, sizes of liposomes (cerasome) derived from the hybrid lipid of the present invention remained unchanged, while traditional liposomes from the DSPC decreased in size obviously in the presence of 5 times amount of TX-100. This indicates that the vesicle structure has been destroyed, which provides strong evidence that cerasomes derived from the hybrid lipid of the present invention show higher stability than the conventional liposomes. The encapsulation rate of the cerasome prepared from the lipid of this embodiment is 95.4%-98.7%.

Example 2

The difference between the present embodiment and embodiment 1 is that the said halogenated group in the present embodiment is Cl, Br or I. Otherwise, the description of embodiment 2 is the same as embodiment 1.

Example 3

The difference between the present embodiment and embodiment 1 or embodiment 2 is that the said $R^1$ in the present embodiment is hexyl, octyl, undecyl, dodecyl, tridecyl, tetradecyl, fifteen alkyl, hexadecyl, seventeen alkyl or octadecyl. Otherwise, the description of embodiment 3 is the same as embodiment 1 and embodiment 2.

Example 4

The difference between the present embodiment and embodiment 1, embodiment 2, or embodiment 3 is that the said $R^2$ in the present embodiment is hexyl, octyl, undecyl, dodecyl, tridecyl, tetradecyl, fifteen alkyl, hexadecyl, seventeen alkyl or octadecyl. Otherwise, the description of embodiment 4 is the same as embodiment 1, embodiment 2, and embodiment 3.

Example 5

A method for making the hybrid lipid compound in embodiment 1 comprises the following steps:
1) forming a compound 1 with a constructional formula

by reacting alkyl amines and alkyl bromide under heating reflux through substitution reaction for 5 days, wherein the alkyl amines is $R^1$—$NH_2$ and the alkyl bromide is $R^2$—Br, in which $R^1$ is $C_6$-$C_{18}$ alkyl and $R^2$ is $C_6$-$C_{18}$ alkyl;
2) forming a compound 2 with a constructional formula

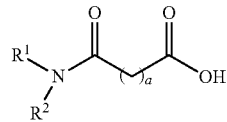

by reacting the compound 1 with succinic anhydride or glutaric anhydride through nucleophilic reaction, wherein a is 2 or 3;

then forming a compound 3 with a constructional formula

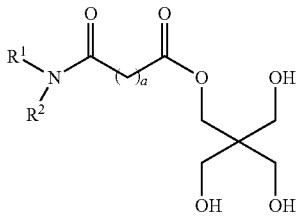

by reacting the compound 2 with excess 4 to 6 times of pentaerythritol through esterification reaction, wherein a is 2 or 3;

3) forming a hybrid lipid compound with a constructional formula

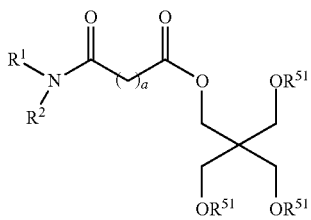

by reacting the compound 3 with 3-isocyanatopropyltriethoxysilane or 3-isocyanatopropyltrimethoxysilane through nucleophilic reaction, wherein $R^{51}$ is —CONH(CH$_2$)$_3$Si(X)$_3$, in which X is ethoxy or methoxy;

or forming a hybrid lipid with a constructional formula

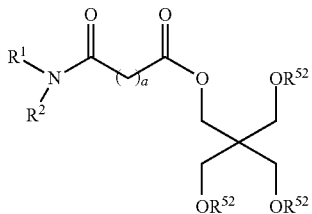

by reacting the compound 3 with 6-Bromohexanoyl chloride through esterification reaction, following reacting with dimethylamine gas saturated tetrahydrofuran solution through nucleophilic reaction, and then reacting with 3-Bromopropyltriethoxysilane or 3-Bromopropyltrimethoxysilane through nucleophilic reaction, wherein $R^{52}$ is —CO(CH$_2$)$_5$N(CH$_3$)$_2$(CH$_2$)$_3$Si(X)$_3$Y, in which X is ethoxy or methoxy and Y is halogenated group;

or forming a hybrid lipid compound with a constructional formula

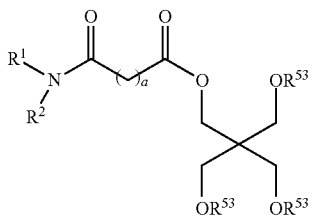

by reacting the compound 3 with succinic anhydride or glutaric anhydride through nucleophilic reaction, following reacting with 3-aminopropyltriethoxysilane or 3-aminopropyltrimethoxysilane through condensation reaction, and then dehydrating, wherein $R^{53}$ is —CO(CH$_2$)$_2$CONH(CH$_2$)$_3$Si(X)$_3$ or —CO(CH$_2$)$_3$CONH(CH$_2$)$_3$Si(X)$_3$, in which X is ethoxy or methoxy.

Example 6

A method for making the hybrid lipid compound with a following constructional formula comprises the following steps:

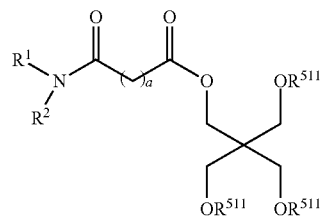

wherein $R^1$ is $C_6$-$C_{18}$ alkyl, $R^2$ is $C_6$-$C_{18}$ alkyl, W and $R^2$ is the same, a is 2 or 3, $R^{511}$ is —CONH(CH$_2$)$_3$Si(X)$_3$, in which X is ethoxy or methoxy.

1) forming a compound 1 with a constructional formula

by reacting alkyl amines and alkyl bromide with the molar ratio of 1:2 under the catalysis of potassium carbonate in a heating reflux ethanol solvent, for 5 days at 95° C.;

2) forming a compound 2 with a constructional formula

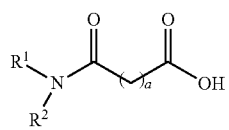

In the tetrahydrofuran solvent, by reacting the compound 1 with succinic anhydride or glutaric anhydride with the molar ratio of 1:1.2 for 2 days at room temperature;

then forming a compound 3 with a constructional formula

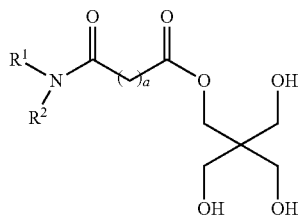

by reacting the compound 2 with excess 4 to 6 times of pentaerythritol with dicyclohexyl carbodiimide (DCC) as condensing agent and 4-dimethylamino pyridine (DMAP) as catalyst at 40° C. for 1 day in dimethyl sulfoxide (DMSO) or dimethylformamide (DMF);

3) forming a hybrid lipid with a constructional formula

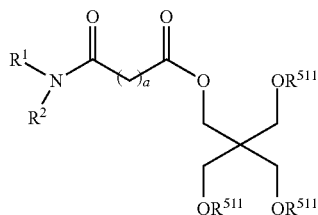

by reacting

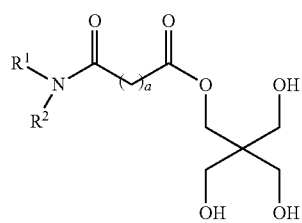

with 3-Isocyanatopropyltriethoxysilane or 3-Isocyanatopropyltrimethoxysilane with the molar ratio of 1:3 in chloroform or methylene chloride solvent for 2-3 days at 50° C., wherein $R^{511}$ is —CONH$(CH_2)_3$Si(X)$_3$, a is 2 or 3, the synthetic route is illustrated in Scheme I

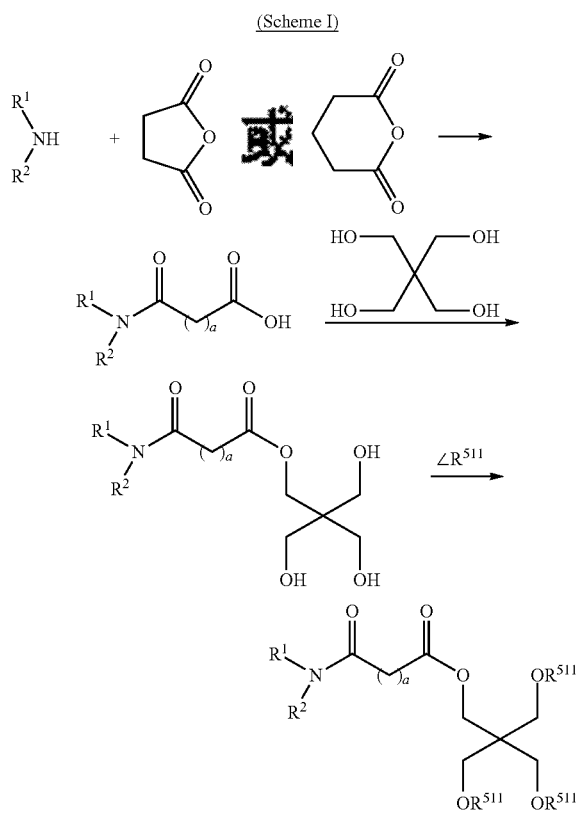

wherein, L in scheme 1 is a leaving group.

Example 7

The difference between the present embodiment and embodiment 6 is that $R^1$ and $R^2$ are different in the present embodiment, and

is formed by reacting alkyl amines $R^1$—$NH_2$ and alkyl bromide Z—$R^2$ with the molar ratio of 1:2 under the catalysis of potassium carbonate for 5 days at 95° C. in a refluxing ethanol solvent, wherein Z is bromide group. Otherwise, the description of embodiment 7 is the same as embodiment 6.

Example 8

A method for preparing a hybrid lipid compound with the following constructional formula is:

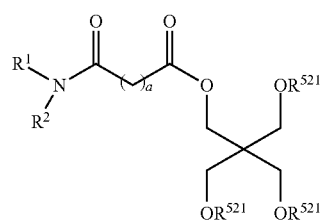

wherein $R^1$ is $C_6$-$C_{18}$ alkyl, $R^2$ is $C_6$-$C_{18}$ alkyl, $R^{521}$ is —CO$(CH_2)_5$N$(CH_3)_2(CH_2)_3$Si(X)$_3$Y, in which X is ethoxy or methoxy, Y is Cl, Br or I;

by reacting the compound 3 with a constructional formula

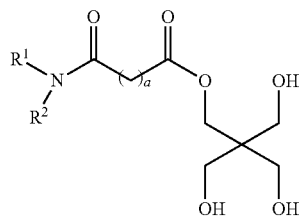

with 6-Bromohexanoyl chloride by esterification reaction with the molar ratio of 1:3.5, following reacting with dimethylamine gas saturated tetrahydrofuran solution through nucleophilic reaction, and then reacting with 3-Bromine propyltriethoxysilane or 3-Bromopropyltrimethoxysilane by nucleophilic reaction with the molar ratio of 1:4 in chloroform or methylene chloride solvent under the catalysis of, organic base (such as triethylamine, pyridine or DMAP) wherein $R^{521}$ is —CO$(CH_2)_5$N$(CH_3)_2(CH_2)_3$Si(X)$_3$Y. The compound in the present embodiment with a constructional formula

| 67 | 68 |
|---|---|
| 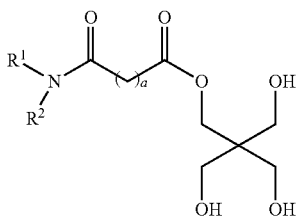 | 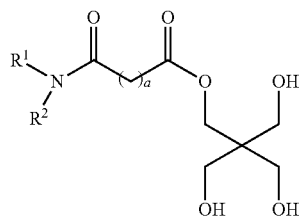 | was prepared according to the embodiment 6 or the embodiment 7.

Example 9

A method for preparing a hybrid lipid compound with a following constructional formula is:

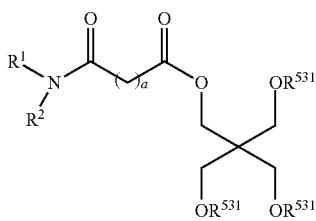

wherein $R^1$ is $C_6$-$C_{18}$ alkyl, $R^2$ is $C_6$-$C_{18}$ alkyl, $R^{531}$ is $CO(CH_2)_aCONH(CH_2)_3Si(X)_3$, in which a is 2 or 3:

by reacting a compound with a constructional formula

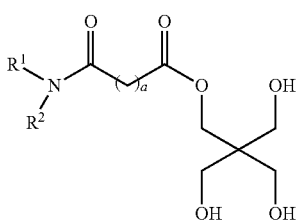

with succinic anhydride or glutaric anhydride through nucleophilic reaction with the molar ratio of 1:6, following reacting with 3-aminopropyltriethoxysilane or 3-aminopropyltrimethoxysilane through nucleophilic reaction under the catalysis of DCC or EDC at room temperature for 24 h, wherein $R^{531}$ is one among the group consisting of CO (CH$_2$)$_a$CONH(CH$_2$)$_3$Si(X)$_3$. The compound in the present embodiment with a constructional formula was prepared according to the embodiment 6 or the embodiment 7.

Example 10

A method for preparing a hybrid lipid compound based on pentaerythritol with the formula of $C_{71}H_{144}N_4O_{18}Si_3$ is as follows:

Put the solution of a compound with a constructional formula

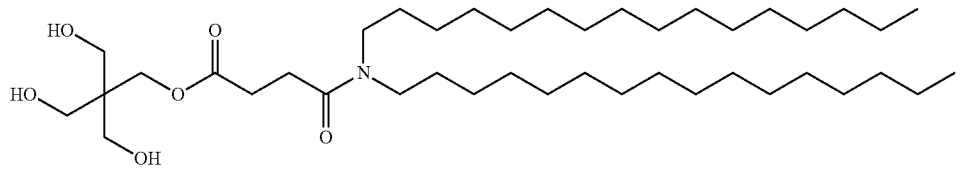 [SMILES: CCCCCCCCCCCCCCCCN(CCCCCCCCCCCCCCCC)C(=O)CCC(=O)OCC(CO)(CO)CO]

(0.24 g, 0.35 mmol) in dry dichloromethane into a 100 mL two necked, round bottomed flask, then add 3-isocyanatopropyltriethoxysilane (0.26 g, 1.05 mmol) and Dibutyltin dilaurate (0.069 g, 0.105 mmol); the reaction mixture was stirred at 40° C. for 48 h under nitrogen atmosphere. After completion, the solution was concentrated under vacuum and the residue was purified with a silica gel column to give a hybrid lipid based on pentaerythritol (colorless oil). The yield is 32%.

The hybrid lipid prepared in this embodiment ($C_{71}H_{144}N_4O_{18}Si_3$): $^1$H NMR (300 MHz, CDCl$_3$) δ: 062 (t, J=8.1 Hz, 6H, SiCH$_2$CH$_2$CH$_2$NH), 0.88 (t, J=6.6 Hz, 6H, NCH$_2$CH$_2$(CH$_2$)$_{13}$CH$_3$), 1.18-1.62 (m, 89H, NCH$_2$CH$_2$ (CH$_2$)$_{13}$CH$_3$ and CH$_3$CH$_2$OSi and SiCH$_2$CH$_2$CH$_2$NH and NCH$_2$CH$_2$(CH$_2$)$_{13}$CH$_3$), 2.60-2.75 (m, 4H, COCH$_2$CH$_2$CO), 3.13-3.16 (m, 10H, SiCH$_2$CH$_2$CH$_2$NH and NCH$_2$CH$_2$(CH$_2$)$_{13}$CH$_3$), 3.85-3.78 (m, 18H, CH$_3$CH$_2$OSi), 4.13-4.08 (m, 8H, COOCH$_2$), 5.30 (s, 3H, NH). Theoretical value MS is 1426.18. found [M]$^+$ is 1427.0; [M Na]$^+$ is 1448.8.

The synthetic route is illustrated as follows:

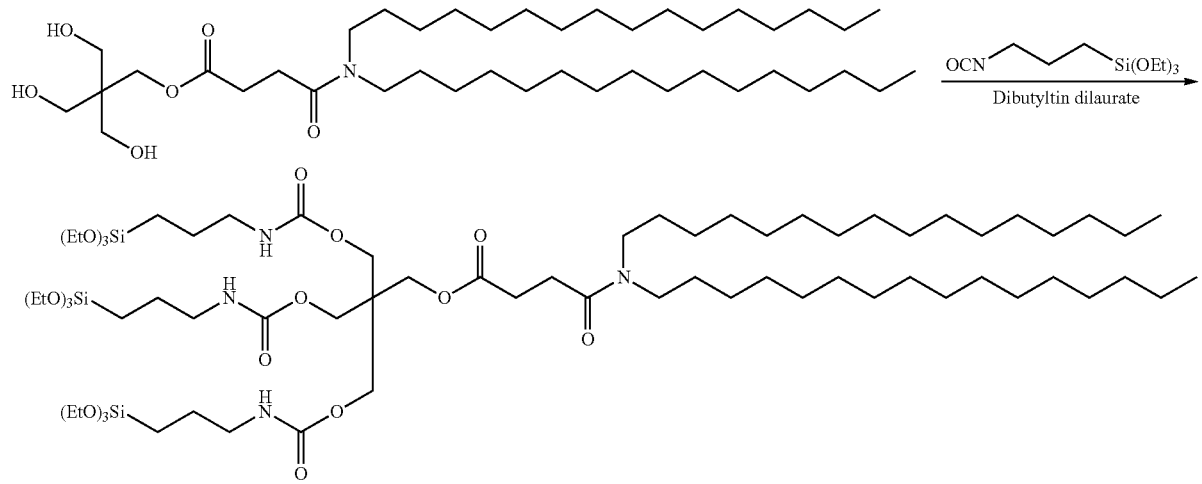

wherein, EtO represents ethoxy.

A method for preparing cerasome (ie, liposomes) is as follows:

Put 2 mg hybrid lipid based on pentaerythritol in this embodiment compound with a constructional formula $C_{71}H_{144}N_4O_{18}Si_3$ into a 20 mL round bottom flask, add 5 mL chloroform to dissolve the compound and then slowly distill to form thin films in the flask wall in a vacuum, dry at 35° C. in a vacuum oven to completely remove the chloroform, water of a different pH was then added to the flask with thin films to reach the solution concentration of 0.5 mmol/L. Such mixture was ultrasonified for 5 minutes to get a certain turbidity of the solution. The resultant solution was placed at room temperature for 12 hours to obtain aqueous solution of cerasome 1. The size and morphology was later detected by DLS and TEM instruments. Specific transmission electron microscopy is shown in FIG. 1, and the particle size is shown in FIG. 2 and Table 1.

Figure 1:
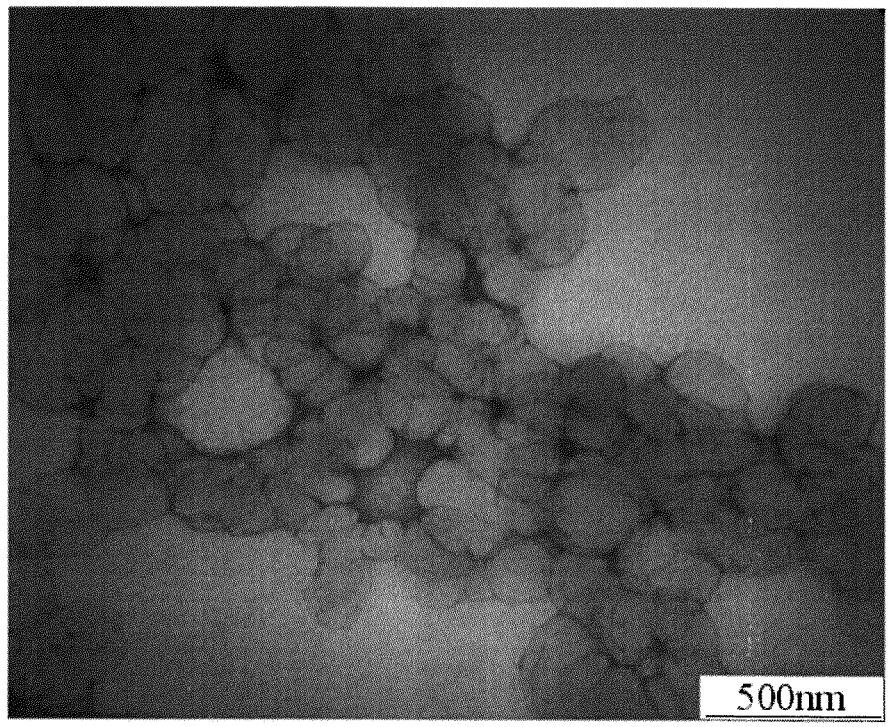
FIG. 1 is the transmittance electron images (TEMs) of cerasome 1 prepared in Embodiment 10.
Figure 2:
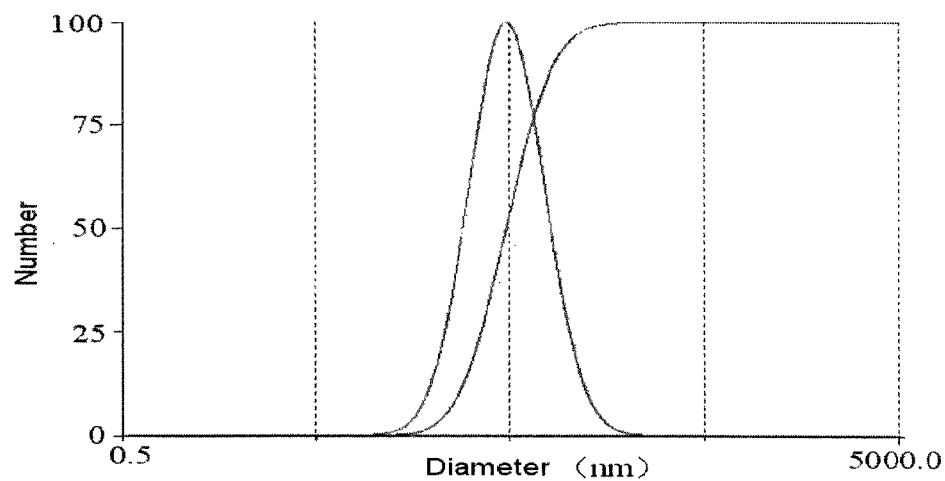
FIG. 2 is the particle size distribution of cerasome 1 prepared in Embodiment 10.

FIG. 1 indicates that particle size of the cerasome prepared by the hybrid lipid compound in this embodiment is about 150 nm. FIG. 2 and Table 1 show the average particle size of the cerasome is 143 nm, with narrow particle size distribution, and a polydispersity index of 0.237.

TABLE 1

Tested results for the properties of cerasome 1

| number of times | Effective diameter (nm) | half-width (nm) | Polydispersity | Baseline index |
|---|---|---|---|---|
| 1 | 145.9 | 77.7 | 0.283 | 8.3 |
| 2 | 141.1 | 72.9 | 0.267 | 4.5 |
| 3 | 143.3 | 71.4 | 0.248 | 0.1 |
| 4 | 146.0 | 73.0 | 0.250 | 1.4 |
| 5 | 141.5 | 59.8 | 0.179 | 8.6 |
| 6 | 140.5 | 67.30 | 0.229 | 5.5 |
| Average | 143.0 | 70.3 | 0.243 | 4.7 |
| Standard error | 1.0 | 2.5 | 0.015 | 1.4 |
| Combined results | 143.0 | 69.7 | 0.237 | 5.6 |

Example 11

The hybrid lipid compound based on pentaerythritol in this embodiment, with a constructional formula

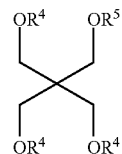

Wherein:
$R^4$ is $C_6$-$C_{18}$ alkyl, $R^5$ is one among the group consisting of $CONH(CH_2)_3Si(X)_3$, $CO(CH_2)_nCONH(CH_2)_3Si(X)_3$ or $CO(CH_2)_5N(CH_3)_2(CH_2)_3Si(X)_3Y$, in which a is 2 or 3, X is a hydrolyzable group which can be ethoxy or methoxy, and Y is the halogenated group.

The liposomes prepared from hybrid lipid compound in this embodiment have uniform size, the silicate network surface and higher stability. When the surfactant Triton X-100 (TX-100) was added to the liposome solution, size changes of liposomes were tested. Conventional liposomes made from phospholipids (DSPC) were used as controls under the same conditions to compare the stability of the cerasomes. When 30 times amount of TX-100 solution was added, the size of liposomes (cerasome) derived from the hybrid lipid of the present invention remained unchanged, while traditional liposomes from the DSPC decreased in size obviously in the presence of 5 times amount of TX-100. This indicates that the vesicle structure has been destroyed, and provides strong evidence that cerasomes derived from the hybrid lipid compound of the present invention shows higher stability than the conventional liposomes. The encapsulation rate of the cerasome prepared from the hybird lipid compound of this embodiment is 95.4%-98.7%.

Example 12

The difference between the present embodiment and embodiment 11 is that the described halogen in the present embodiment can be one among the group of Cl, Br or I. Otherwise, the description of embodiment 12 is the same as the embodiment 11.

Example 13

The difference between the present embodiment and embodiment 11 or embodiment 12 is that the described $R^4$ in the present embodiment can be one among the group of hexyl, octyl, undecyl, dodecyl, tridecyl, tetradecyl, fifteen alkyl, hexadecyl, seventeen alkyl and octadecyl. Otherwise, the description of embodiment 13 is the same as the embodiment 11 and the embodiment 12.

Example 14

The hybrid lipid compound based on pentaerythritol in this embodiment with a constructional formula

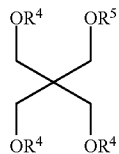

wherein:
$R^4$ is $C_6$-$C_{18}$ alkyl, $R^5$ is one among the group consisting of $CONH(CH_2)_3Si(X)_3$, $CO(CH_2)_aCONH(CH_2)_3Si(X)_3$ or $CO(CH_2)_5N(CH_3)_2(CH_2)_3Si(X)_3Y$, in which a is 2 or 3, X is a hydrolyzable group which can be ethoxy or methoxy, and Y is the halogenated group.

A method for preparing the above hybrid lipid compound comprises the following steps:

1) forming a compound with a constructional formula

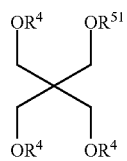

by reacting pentaerythritol and 3 times excess amount of alkyl bromide with a constructional formula $R_4$—Br in alkaline conditions through the nucleophilic substitution reaction for 6 hours, wherein $R^4$ is $C_6$-$C_{18}$ alkyl;

2) forming a hybrid lipid with a constructional formula

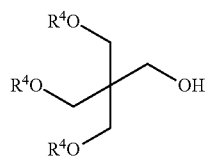

by reacting a compound with a constructional formula

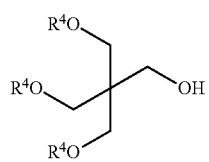

with 3-Isocyanatopropyltriethoxysilane or 3-Isocyanatopropyltrimethoxysilane through nucleophilic reaction for 2-3 days, wherein $R^{51}$ is —$CONH(CH_2)_3Si(X)_3$;

or by reacting a compound with a constructional formula

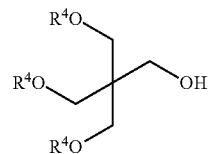

with 6-Bromohexanoyl chloride by esterification reaction, following reacting with dimethylamine gas saturated tetrahydrofuran solution through nucleophilic reaction, and then reacting with 3-Bromopropyltriethoxysilane or 3-Bromopropyltrimethoxysilane through nucleophilic reaction to yield a hybrid lipid compound with a constructional formula

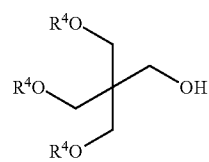

wherein $R^{52}$ is —$CO(CH_2)_5N(CH_3)_2(CH_2)_3Si(X)_3Y$;

or by reacting a compound with a constructional formula

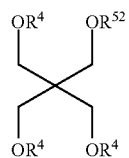

with succinic anhydride or glutaric anhydride through nucleophilic reaction, following reacting with 3-aminopropyltriethoxysilane or 3-aminopropyltrimethoxysilane through nucleophilic reaction to yield a hybrid lipid compound with a constructional formula

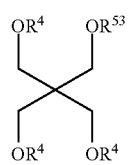

wherein $R^{53}$ is —$CO(CH_2)_aCONH(CH_2)_3Si(X)_3$, $R^4$ is $C_6$-$C_{18}$ alkyl; in which X is a hydrolyzable group which can be ethoxy or methoxy, Y is the halogenated group, and a is 2 or 3.

Example 15

The hybrid lipid compound based on pentaerythritol in this embodiment with a constructional formula

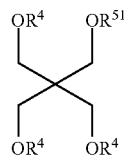

wherein:

$R^4$ is $C_8$-$C_{18}$ alkyl, $R^{51}$ is $CONH(CH_2)_3Si(X)_3$, in which X is ethoxy or methoxy.

A method for preparing the above hybrid lipid compound comprises following steps:

1) forming a compound with a constructional formula

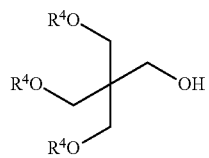

by reacting pentaerythritol and 3 times excess amount of alkyl bromide with a constructional formula $R^4$—Br through the nucleophilic substitution reaction for 6 hours;

2) forming a hybrid lipid with a constructional formula

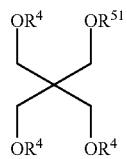

in chloroform or Dichloromethane solvent, by reacting a compound with a constructional formula

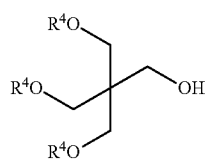

with 3-Isocyanatopropyltriethoxysilane or 3-Isocyanatopropyltrimethoxysilane with the molar ratio of 1:1 under the catalysis of Dibutyltin laurate at 50° C. for 2-3 days, wherein $R^{51}$ is —CONH(CH$_2$)$_3$Si(X)$_3$.

The synthetic route of the hybrid lipid compound based on pentaerythritol is illustrated in Scheme II (Scheme II)

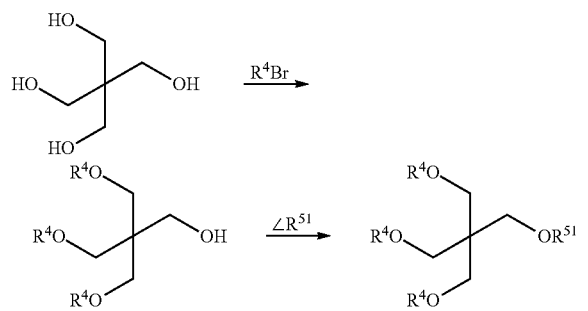

wherein, L in scheme II is a leaving group.

Example 16

The hybrid lipid compound based on pentaerythritol in this embodiment with a constructional formula

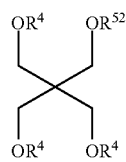

wherein:

$R^4$ is $C_6$-$C_{18}$ alkyl, $R^{52}$ is $CO(CH_2)_5N(CH_3)_2(CH_2)_3Si(X)_3Y$, in which X is ethoxy or methoxy, Y is Cl, Br or I.

A method for preparing the above hybrid lipid compound is as follows:

In chloroform or dichloromethane solvent, by reacting a compound with a constructional formula

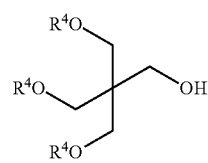

with 6-Bromohexanoyl chloride by esterification reaction with the molar ratio of 1:1.5 under the catalysis of organic base (such as triethylamine, pyridine or DMAP), following reacting with dimethylamine gas saturated tetrahydrofuran solution through nucleophilic reaction, and then reacting with 3-Bromopropyltriethoxysilane or 3-Bromopropyltrimethoxysilane with the molar ratio of 1:4 through nucleophilic reaction to yield a compound with a constructional formula

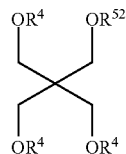

wherein $R^{52}$ is —$CO(CH_2)_5N(CH_3)_2(CH_2)_3Si(X)_3Y$. The compound in the present embodiment with a constructional formula of

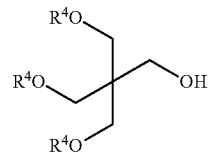

was prepared according to the embodiment 15.

Example 17

The hybrid lipid based on pentaerythritol in this embodiment with a constructional formula

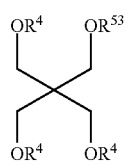

wherein:

$R^4$ is $C_6$-$C_{18}$ alkyl, $R^{53}$ is $CO(CH_2)_a CONH(CH_2)_3 Si(X)_3$, in which a is 2 or 3, X is ethoxy or methoxy.

A method for preparing the above hybrid lipid compound is as follows: by reacting a compound with a constructional formula

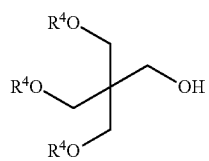

with succinic anhydride or glutaric anhydride through nucleophilic reaction with the molar ratio of 1:2, following reacting with 3-aminopropyltriethoxysilane or 3-aminopropyltrimethoxysilane with the molar ratio of 1:1.5 through nucleophilic reaction under the catalysis of DCC or EDC at room temperature for 24 hours to yield a hybrid lipid compound with a constructional formula

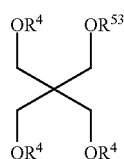

wherein $R^{53}$ is $CO(CH_2)_a CONH(CH_2)_3 Si(X)_3$. The compound in the present embodiment with a constructional formula of

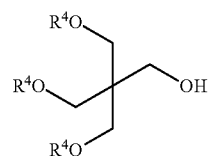

was prepared according to the embodiment 15.

Example 18

A method for preparing a hybrid lipid based on pentaerythritol with a constructional formula $C_{63}H_{129}NO_8Si$ is as follows:

Put the solution of a compound with a constructional formula

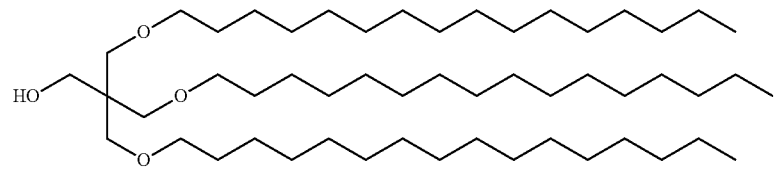

(0.25 g, 0.31 mmol) in dry dichloromethane (20 mL), then add 3-Isocyanatopropyltriethoxysilane (0.073 g, 0.31 mmol) and dibutyltin laurate (0.039 g, 0.062 mmol) under nitrogen atmosphere. Later, the above mixture was heated in 50° C. oil bath for 48 hours. The solution was then concentrated under vacuum and the residue was purified with a silica gel column to give the hybrid lipid compound based on pentaerythritol. The yield is 81%.

The synthetic route is illustrated as follows:

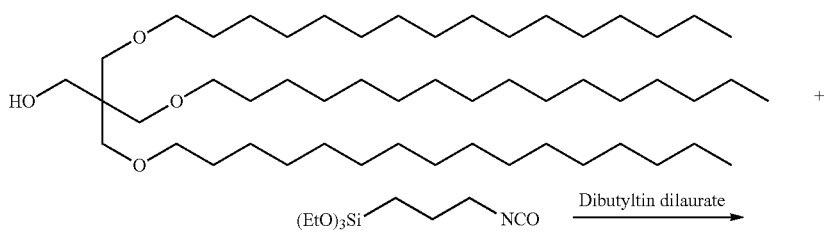

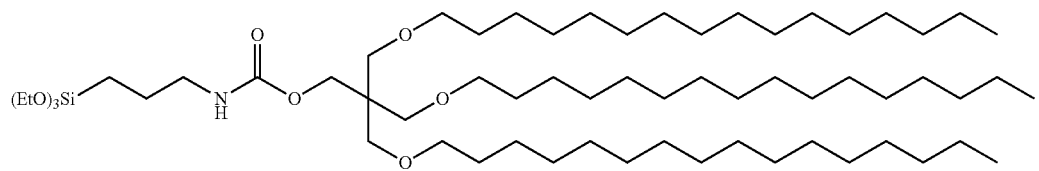

The hybrid lipid prepared in this embodiment ($C_{63}H_{129}NO_8Si$): $^1$H NMR ($CDCl_3$, 300 MHz) δ: 0.63 (t, J=8.2 Hz, 2H, $SiCH_2CH_2CH_2NH$), 0.88 (t, J=6.6 Hz, 9H, $CH_3$), 1.20-1.26 (m, 87H, $SiOCH_2CH_3$), 1.47-1.65 (m, 8H, $SiCH_2CH_2CH_2NH$ and $OCH_2CH_2(CH_2)_{13}CH_3$), 3.16 (t, J=5.1 Hz, 2H, $SiCH_2CH_2CH_2NH$), 3.15-3.19 (m, 12H, $CH_2OCH_2$), 3.83 (q, J=7.0 Hz, 6H, $SiOCH_2CH_3$), 4.10 (s, 2H, $COOCH_2CCH_2O$), 4.83 (s, 1H, NH). The theoretical value of MS is 1056.7, and found $[M]^+$ is 1057.4.

The preparation method of the cerasome from the hybrid lipid based on pentaerythritol in this present embodiment was the same as the embodiment 2. The transmittance electron images of cerasome 2 are illustrated in FIG. 3, and the size distribution is shown in FIG. 4 and table 2.

Figure 3:
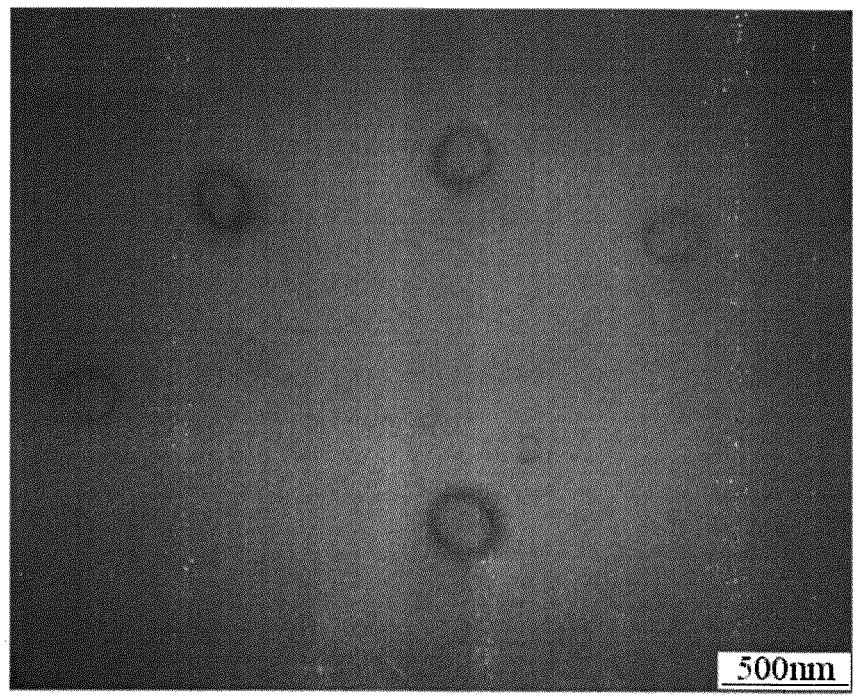
FIG. 3 is the transmittance electron images (TEMs) of cerasome 2 prepared in Embodiment 18.
Figure 4:
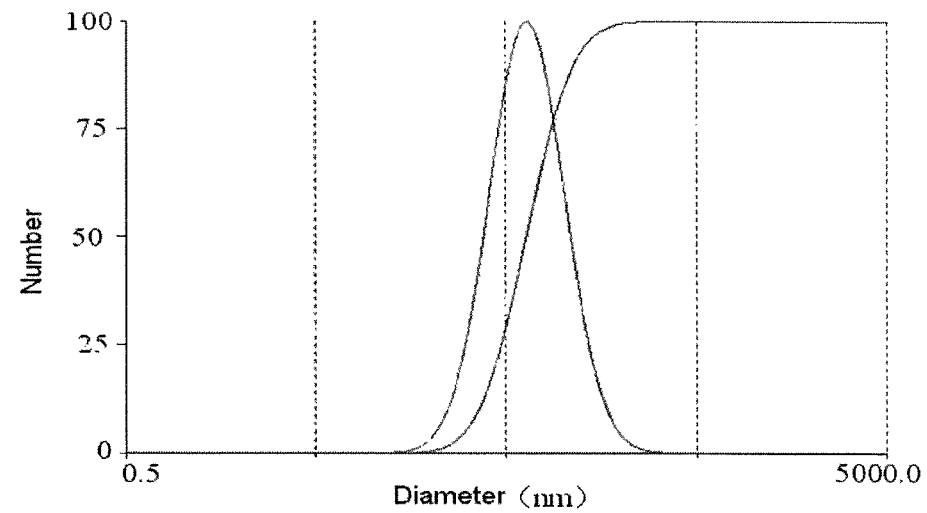
FIG. 4 is the particle size distribution of cerasome 2 prepared in Embodiment 18.

FIG. 3 indicates that the particle size of the cerasome 2 prepared from the hybrid lipid in this embodiment is about 200 nm. FIG. 4 and Table 2 show the average particle size of the cerasome is 196 nm, with narrow particle size distribution, and a polydispersity index of 0.243.

TABLE 2

Tested results for the properties of cerasome 2

| number of times | Effective diameter (nm) | half-width (nm) | Polydispersity | Baseline index |
|---|---|---|---|---|
| 1 | 190.0 | 79.8 | 0.176 | 0.0 |
| 2 | 195.9 | 95.8 | 0.239 | 2.5 |
| 3 | 195.9 | 103.1 | 0.277 | 0.0 |
| 4 | 194.1 | 80.1 | 0.170 | 9.9 |
| 5 | 186.2 | 76.0 | 0.167 | 2.3 |
| 6 | 202.2 | 106.5 | 0.277 | 3.6 |
| Average | 194.0 | 90.2 | 0.218 | 3.1 |
| Standard error | 2.3 | 5.4 | 0.022 | 1.5 |
| Combined results | 195.9 | 96.6 | 0.243 | 3.4 |

Example 19

A method for preparing a hybrid lipid compound based on pentaerythritol with a constructional formula $C_{66}H_{133}NO_9Si$ is as follows:

Step 1: To the solution of a compound with a constructional formula of

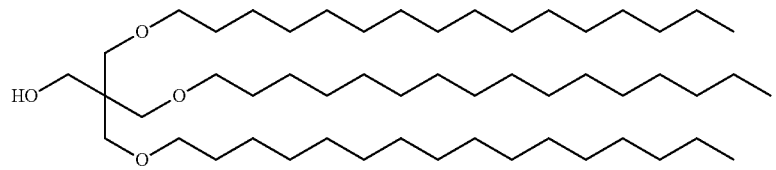

(0.17 g, 0.21 mmol) and succinic anhydride (0.042 g, 0.42 mmol) in dichloromethane (20 mL), DMAP (0.028 g, 0.21 mmol) and triethyl amine (0.084 g, 0.84 mmol) were added. The reaction mixture was warmed to 30° C. and stirred at this temperature for 5 d. The reaction solution was then concentrated under vacuum and the residue was purified by column chromatography to give a white solid compound based on pentaerythritol with a constructional formula $C_{57}H_{112}O_7$. The yield is 70%.

The synthetic route is illustrated as follows:

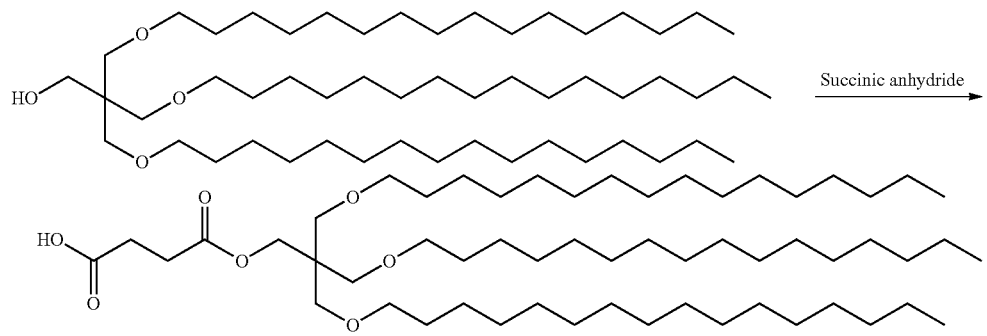

The target compound prepared in this embodiment $(C_{57}H_{112}O_7)$: $^1$H NMR (CDCl$_3$, 300 MHz) δ: 0.90 (t, J is 6.6 Hz, 9H, CH$_3$), 1.25-1.52 (m, 86H, OCH$_2$CH$_2$(CH$_2$)$_{13}$CH$_3$ and NCH$_2$CH$_2$(CH$_2$)$_{13}$CH$_3$ and COOCH$_2$CCH$_2$O), 2.85-2.89 (m, 4H, COCH$_2$CH$_2$CO), 3.33-3.37 (m, 12H, HOCH$_2$CCH$_2$O and OCH$_2$CH$_2$(CH$_2$)$_{13}$CH$_3$), 4.15 (s, 1H, OH). The theoretical value of MS is 909.49, and the found [M]$^+$ is 910.1.

Step 2: To the solution of compound with a constructional formula

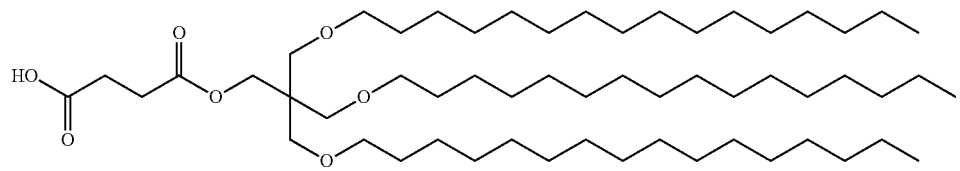 [SMILES: CCCCCCCCCCCCCCCCOCC(COCCCCCCCCCCCCCCCC)(COCCCCCCCCCCCCCCCC)COC(=O)CCC(=O)O]

(0.255 g, 0.28 mmol) in dry dichloromethane (20 mL), DDC was added (0.069 g, 0.336 mmol). After 15 min of stirring at room temperature, 3-aminopropyltriethoxysilane (0.093 g, 0.42 mmol) was then added to the solution and the mixture was stirred for 1d at room temperature. Then the solution was concentrated under vacuum and the residue was purified with a silica gel column to give the hybrid lipid compound based on pentaerythritol (white solid). The yield is 50%.

The synthetic route is illustrated as follows:

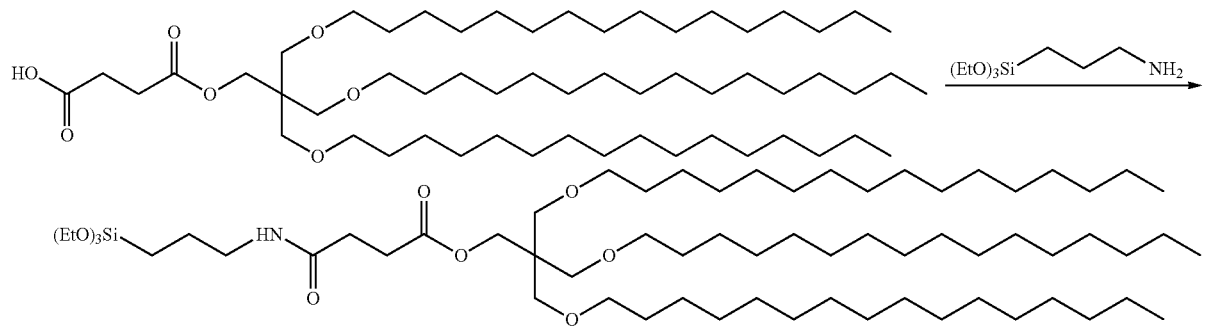

The hybrid lipid prepared in this embodiment ($C_{66}H_{133}NO_9Si$): $^1H$ NMR (CDCl$_3$, 300 MHz) δ: 0.64 (t, J=8.2 Hz, 2H, SiCH$_2$CH$_2$CH$_2$NH), 0.88 (t, J=6.7 Hz, 9H, CH$_3$), 1.16-1.32 (m, 87H, OCH$_2$CH$_2$(CH$_2$)$_{13}$CH$_3$ and SiOCH$_2$CH$_3$), 1.43-1.68 (m, 8H, OCH$_2$CH$_2$(CH$_2$)$_{13}$CH$_3$ and SiCH$_2$CH$_2$CH$_2$NH), 2.45 (t, J=7.1 Hz, 2H, COCH$_2$CH$_2$CO), 2.67 (t, J=7.1 Hz, 2H, COCH$_2$CH$_2$CO), 3.20-3.37 (m, 14H, SiCH$_2$CH$_2$CH$_2$NH and COOCH$_2$CCH$_2$O and OCH$_2$CH$_2$(CH$_2$)$_{13}$CH$_3$), 3.83 (q, J=7.0 Hz, 6H, SiOCH$_2$CH$_3$), 4.12 (s, 2H, COOCH$_2$CCH$_2$O). The theoretical value of MS is 1112.8, and the found [M]$^+$ is 1113.5.

Figure 6:
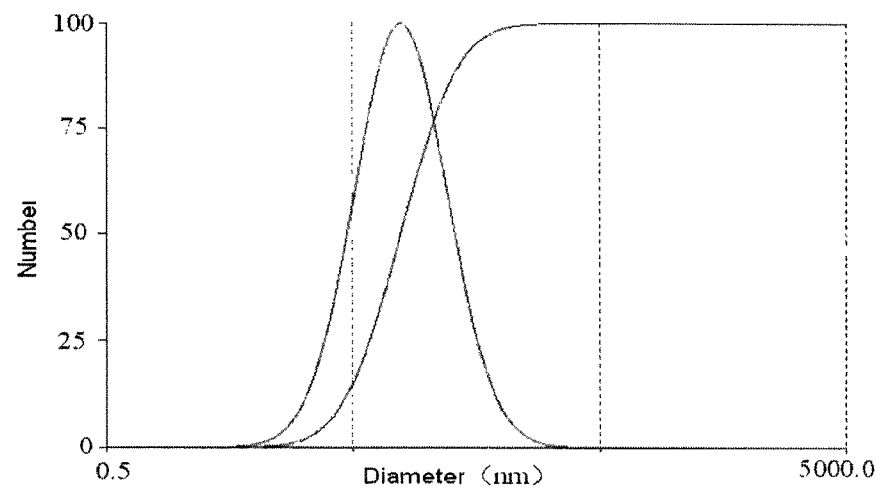
FIG. 6 is the particle size distribution of cerasome 3 prepared in Embodiment 19.

The preparation method of the cerasome 3 from the hybrid lipid compound based on pentaerythritol with a constructional formula $C_{66}H_{133}NO_9Si$ in this present embodiment was the same as the embodiment 10. The transmittance electron image of cerasome 3 is illustrated in FIG. 5, and the size distribution is shown in FIG. 6 and table 3.

Figure 5:
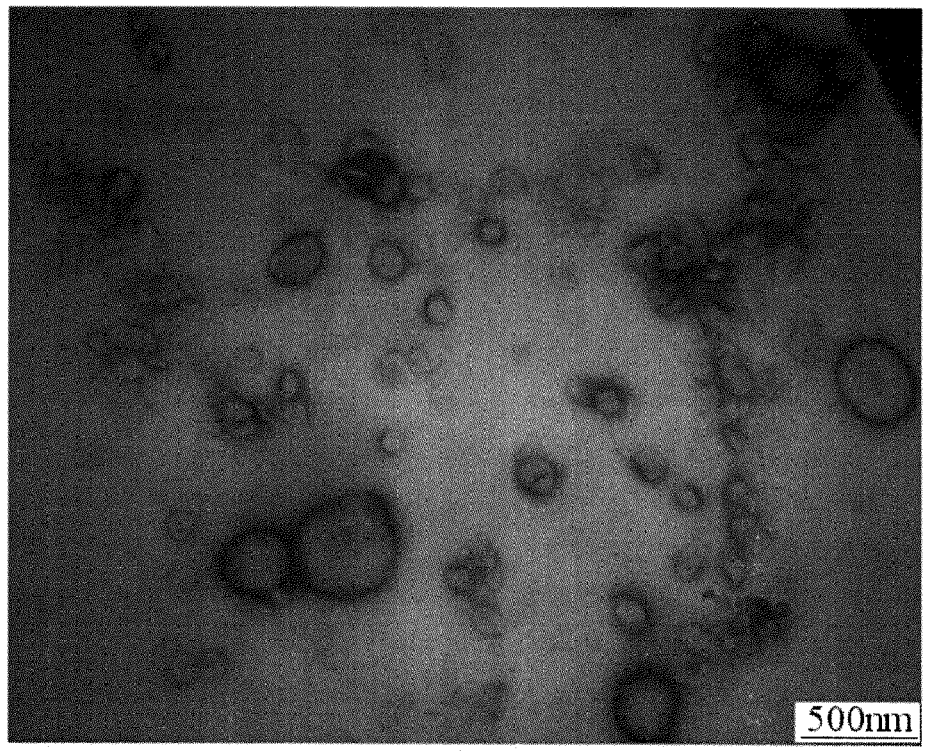
FIG. 5 is the transmittance electron images (TEMs) of cerasome 3 prepared in Embodiment 19.

FIG. 5 indicates that the particle size of the cerasome prepared from the hybrid lipid compound in this embodiment is about 200 nm. FIG. 6 and Table 3 show the average particle size of the cerasome is 216 nm, with narrow particle size distribution and a polydispersity index of 0.222.

TABLE 3

Tested results for the properties of cerasome 3

| number of times | Effective diameter (nm) | half-width (nm) | Polydispersity | Baseline index |
|---|---|---|---|---|
| 1 | s | 91.8 | 0181 | 5.3 |
| 2 | 217.4 | 102.4 | 0.222 | 4.3 |
| 3 | 214.3 | 112.1 | 0.274 | 0.1 |
| 4 | 217.7 | 103.1 | 0.224 | 4.0 |
| 5 | 206.2 | 99.1 | 0.231 | 2.8 |
| 6 | 219.1 | 105.3 | 0.231 | 0.0 |
| Average | 215.1 | 101.8 | 0.227 | 2.8 |
| Standard error | 1.9 | 2.7 | 0.012 | 0.9 |
| Combined results | 215.9 | 101.8 | 0.222 | 2.2 |

Example 20 stability study of cerasomes 1, 2 and 3

Cerasomes 1, 2 and 3 were prepared from the corresponding hybrid lipid compound with a constructional formula $C_{71}H_{144}N_4O_{18}Si_3$, $C_{63}H_{129}NO_8Si$ and $C_{66}H_{133}NO_9Si$. When surfactant Triton X-100 (TX-100) was added to the above cerasome solution, size changes of cerasomes were tested. Conventional liposomes made from phospholipids (DSPC) were used as controls under the same conditions to compare the stability of the cerasome. The result is shown in table 4. When 30 times amount of TX-100 solution was added, sizes of cerasome derived from the hybrid lipid remained unchanged, while traditional liposomes from the DSPC decreased in size obviously in the presence of 5 times amount of TX-100. This indicates that the vesicle structure has been destroyed, providing strong evidence that cerasomes derived from hybrid lipid of the present invention show higher stability than the conventional liposomes. The stability evaluated results of cerasome are illustrated in table 4.

TABLE 4

Stability of cerasome

| | The average particle size $D_{hy}$ (nm) | | | |
|---|---|---|---|---|
| TX-100/lipid Molar ratio | Cerasome 1 | Cerasome 2 | Cerasome 3 | DSPC liposome |
| 0 time | 156.1 | 169 | 183 | 161.7 |
| 5 times | 155.9 | 166 | 179.5 | 20.1 |
| 10 times | 167.6 | 166.7 | 182 | — |
| 15 times | 173.4 | 165.5 | 184.6 | — |
| 20 times | 179.9 | 166.3 | 189.1 | — |
| 25 times | 177.6 | 167.4 | 197.1 | — |
| 30 times | 212.6 | 173.9 | 199.4 | — |

Example 21

A method for preparing a hybrid lipid compound based on pentaerythritol with a constructional formula $C_{70}H_{144}NO_8Si^+Br$ is as follows:

Step 1: To the solution of a compound with a constructional formula

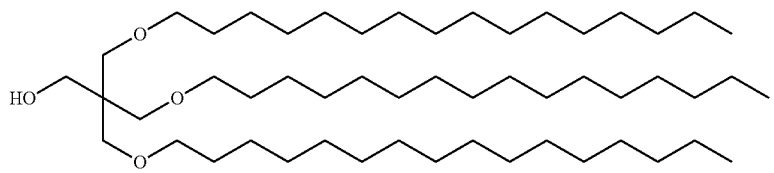

(0.65 g, 0.80 mmol) in dichloromethane (20 mL), DMAP (0.10 g, 0.8 mmol) and triethyl amine (0.162 g, 1.6 mmol) were added. The reaction mixture was cooled to 0° C. and then dichloromethane solvent (8 mL) with 6-Bromohexanoyl chloride (0.27 g, 1.2 mmol) was added dropwise to the solution and stirred at this temperature for 1 hour. Later, the solution was stirred at room temperature for another 16 hours. The reaction solution was then concentrated under vacuum and the residue was purified by column chromatography to give a colorless oil compound based on pentaerythritol with a constructional formula $C_{55}H_{117}BrO_5$. The yield is 56%.

The synthetic route is illustrated as follows:

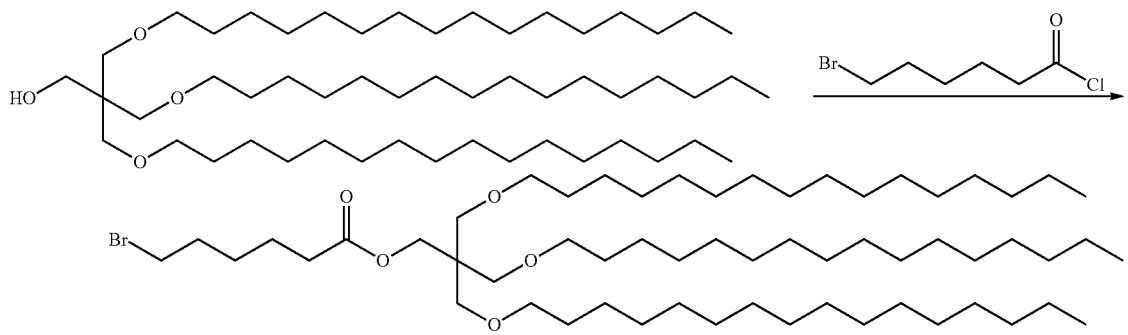

The target compound prepared in this embodiment ($C_{55}H_{117}BrO_5$): $^1$H NMR (CDCl$_3$, 400 MHz) δ: 0.88 (t, J=7.2 Hz, 9H, CH$_3$), 1.26-1.45 (m, 78H, OCH$_2$CH$_2$(CH$_2$)$_{13}$CH$_3$) 1.45-1.52 (m, 8H, OCH$_2$CH$_2$(CH$_2$)$_{13}$CH$_3$ and BrCH$_2$CH$_2$CH$_2$), 1.84-1.91 (m, 4H, BrCH$_2$CH$_2$CH$_2$CH$_2$CH$_2$CO), 2.31 (t, J=7.4 Hz, 2H, BrCH$_2$CH$_2$CH$_2$CH$_2$CH$_2$CO), 3.33-3.37 (m, 12H, COOCH$_2$CCH$_2$O and OCH$_2$CH$_2$(CH$_2$)$_{13}$CH$_3$), 3.40 (t, J=7.6 Hz, 2H, BrCH$_2$), 4.11 (s, 2H, COOCH$_2$). The theoretical value of MS is 986.46, and the found [M]$^+$ is 986.0, 988.0.

Step 2: To the solution of a compound with a constructional formula

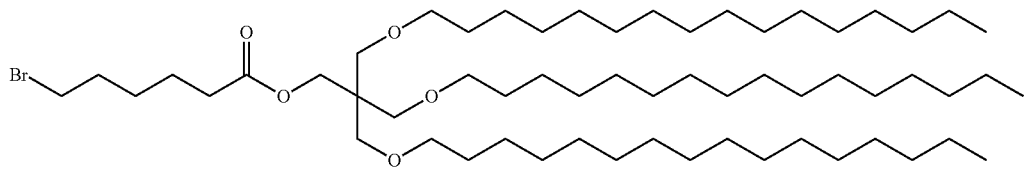 [SMILES: CCCCCCCCCCCCCCCCOCC(COCCCCCCCCCCCCCCCC)(COCCCCCCCCCCCCCCCC)COC(=O)CCCCCBr]

(0.45 g, 0.46 mmol) in the dimethylamine saturated THF solution (40 mL). The mixture was subsequently stirred at room temperature for 3 days. Air then was bubbled into the mixture in order to remove excess dimethylamine. The solvent was evaporated in vacuum and the residual solid was dissolved in chloroform (20 mL). The solution was then washed in turn with saturated aqueous sodium chloride, and 4% aqueous sodium hydrogen carbonate. After drying using anhydrous Magnesium sulfate, the solvent was evaporated in vacuum. The residue was purified with a silica gel column to give a white solid compound based on pentaerythritol with a constructional formula $C_{61}H_{123}NO_5$. The yield is 70%.

The synthetic route is illustrated as follows:

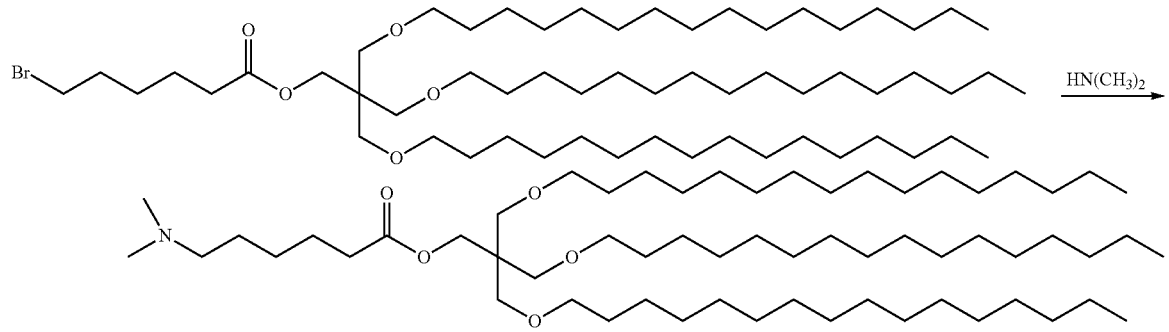

The hybrid lipid intermediates prepared in this embodiment ($C_{61}H_{123}NO_5$): $^1$H NMR (CDCl$_3$, 400 MHz) δ: 0.88 (t, J=7.1 Hz, 9H, CH$_3$), 1.26-1.47 (m, 78H, OCH$_2$CH$_2$(CH$_2$)$_{13}$CH$_3$) 1.48-1.64 (m, 12H, OCH$_2$CH$_2$(CH$_2$)$_{13}$CH$_3$ and NCH$_2$CH$_2$CH$_2$ CH$_2$), 2.26 (s, 6H, N(CH$_3$)$_2$), 2.32 (t, J=7.2 Hz, 2H, NCH$_2$CH$_2$CH$_2$CH$_2$CH$_2$CO), 2.46 (t, J=7.1 Hz, 2H, NCH$_2$CH$_2$CH$_2$CH$_2$CH$_2$CO), 3.33-3.40 (m, 12H, COOCH$_2$CCH$_2$O and OCH$_2$CH$_2$(CH$_2$)$_{13}$CH$_3$), 4.10 (s, 2H, COOCH$_2$). The theoretical value of MS is 950.63, and the found [M]$^+$ is 951.7.

Step 3: The solution of the compound with the structure of

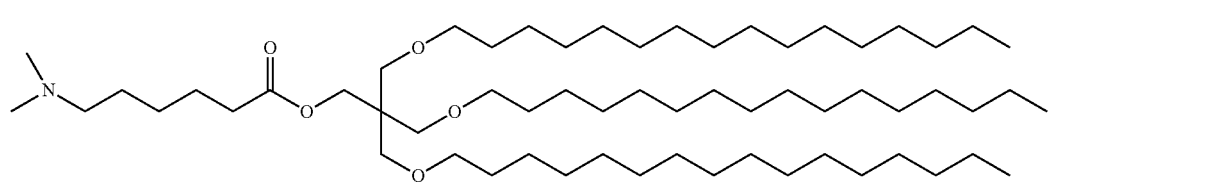 [SMILES: CCCCCCCCCCCCCCCCOCC(COCCCCCCCCCCCCCCCC)(COCCCCCCCCCCCCCCCC)COC(=O)CCCCCN(C)C]

(0.282 g, 0.316 mmol) was added under a nitrogen atmosphere to a solution of 3-bromopropyltriethoxysilane (0.516 g, 1.264 mmol) in dry DMF (25 mL), and the mixture was stirred for 5 days. The solvent was evaporated in vacuum and the residue was purified by a silica gel column to afford a colorless viscous oil based on pentaerythritol with a constructional formula $C_{70}H_{144}NO_8Si^+$. The yield is 41%.

The synthetic route is illustrated as follows:

The hybrid lipid prepared in this embodiment ($C_{70}H_{144}NO_8Si^+$): $^1$H NMR (CDCl$_3$, 400 MHz): d=0.59 (t, J=7.8 Hz, 2H, SiCH$_2$), 0.88 (t, J=6.6 Hz, 9H, OCH$_2$CH$_2$(CH$_2$)$_{13}$CH$_3$), 1.25-1.43 (m, 89H, NCH$_2$CH$_2$(CH$_2$)$_{13}$CH$_3$, N$^+$CH$_2$CH$_2$CH$_2$CH$_2$CH$_2$CO, CH$_3$CH$_2$OSi), 1.73-1.81 (m, 12H, OCH$_2$CH$_2$(CH$_2$)$_{13}$CH$_3$, CH$_2$CH$_2$CH$_2$N$^+$CH$_2$CH$_2$CH$_2$CH$_2$CH$_2$CO), 2.33 (t, J=7.0 Hz, 2H, N$^+$CH$_2$CH$_2$CH$_2$CH$_2$CH$_2$CO), 3.24-3.26 (m, 4H, CH$_2$CH$_2$N$^+$CH$_2$CH$_2$), 3.31 (s, 6H, CH$_2$N$^+$(CH$_3$)$_2$CH$_2$), 3.37-3.39 (m, 6H, OCH$_2$CH$_2$(CH$_2$)$_{13}$CH$_3$), 3.79-3.83 (m, 12H, CH$_3$CH$_2$OSi, CCH$_2$O), 4.01 (s, 1H, COOCH$_2$).

Example 22

A method for preparing a hybrid lipid compound based on pentaerythritol with a constructional formula $C_{80}H_{156}N_4O_{21}Si_3$ is as follows:

Step 1: To the solution of compound with a constructional formula

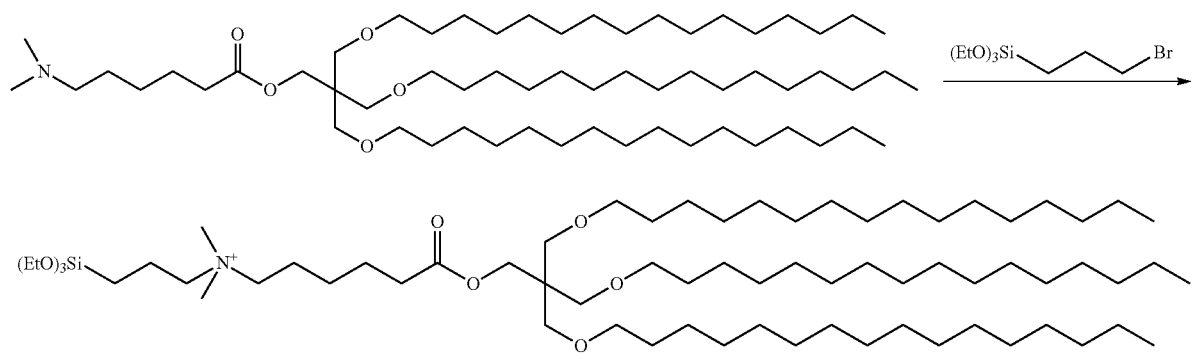

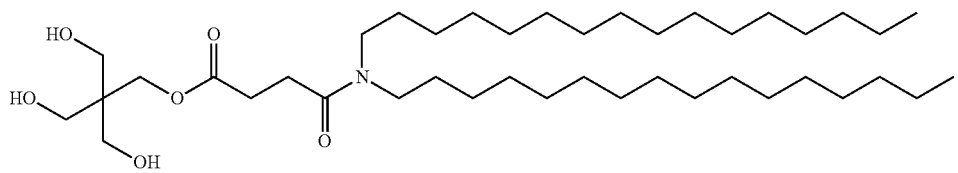 [SMILES: CCCCCCCCCCCCCCCCN(CCCCCCCCCCCCCCCC)C(=O)CCC(=O)OCC(CO)(CO)CO]

(0.50 g, 0.73 mmol) and succinic anhydride (0.438 g, 4.38 mmol) in dichloromethane (25 mL), DMAP (0.089 g, 0.73 mmol) and triethyl amine (0.293 g, 2.92 mmol) were added. The reaction mixture was heated to 30° C. and the resultant mixture stirred at this temperature for 4 days. The reaction solution was then concentrated under vacuum and the residue was purified by column chromatography to give a white solid compound based on pentaerythritol with a constructional formula $C_{53}H_{93}NO_{15}$. The yield is 75%.

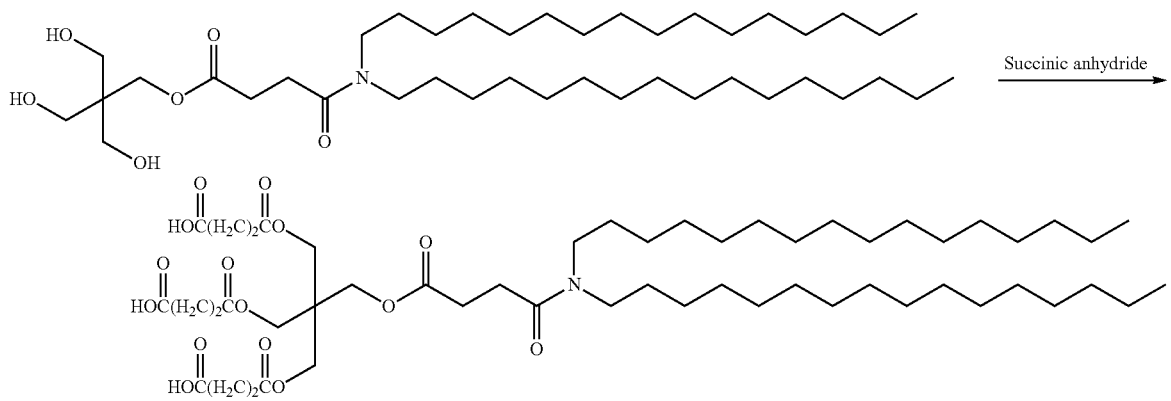

The synthetic route is illustrated as follows:

The target compound prepared in this embodiment ($C_{53}H_{93}NO_{15}$): $^1$H NMR (CDCl$_3$, 400 MHz) a: 0.88 (t, J=6.7 Hz, 6H, NCH$_2$CH$_2$(CH$_2$)$_{13}$CH$_3$), 1.26-1.52 (m, 56H, NCH$_2$CH$_2$(CH$_2$)$_{13}$CH$_3$NCH$_2$CH$_2$(CH$_2$)$_{13}$CH$_3$), 2.61-2.72 (m, 4H, NCOCH$_2$CH$_2$CO), 2.73-2.82 (m, 12H, COCH$_2$CH$_2$COOH), 3.20-3.21 (m, 4H, NCH$_2$), 4.00 (s, CCH$_2$COO). The theoretical value of MS is 984.30, and the found $[M]^+$ is 985.4.

Step 2: To the solution of compound with a constructional formula

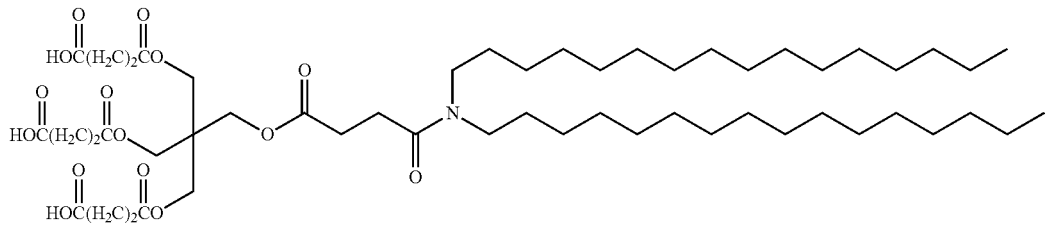

(0.30 g, 0.305 mmol) in the dichloromethane solution (20 mL), DDC (0.075 g, 0.366 mmol) was added. After 15 min of stirring, 3-aminopropyltriethoxysilane (0.308 g, 1.38 mmol) was added to the solution and the mixture was stirred for 1d at room temperature. The solution was then concentrated under vacuum and the residue was purified with a silica gel column to give the hybrid lipid based on pentaerythritol (colorless oil). The yield is 53%.

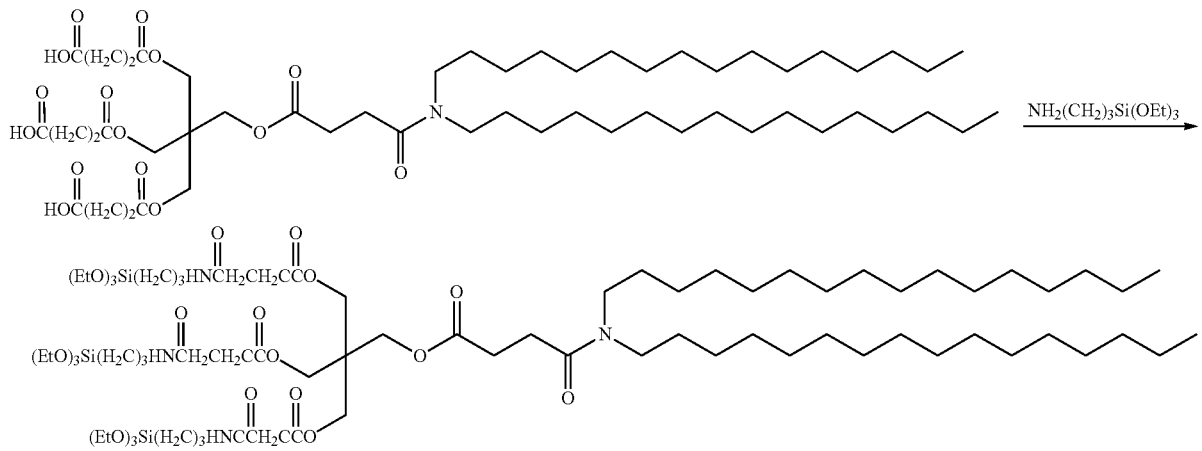

The synthetic route is illustrated as follows:

The hybrid lipid intermediates prepared in this embodiment ($C_{80}H_{156}N_4O_{21}Si_3$): $^1H$ NMR (CDCl$_3$, 400 MHz) δ: 062 (t, J=8.0 Hz, 6H, SiCH$_2$CH$_2$CH$_2$NH), 0.88 (t, J=6.6 Hz, 6H, NCH$_2$CH$_2$(CH$_2$)$_{13}$CH$_3$), 1.20-1.61 (m, 89H, NCH$_2$CH$_2$ (CH$_2$)$_{13}$CH$_3$ and CH$_3$CH$_2$OSi, SiCH$_2$CH$_2$CH$_2$NH, NCH$_2$CH$_2$(CH$_2$)$_{13}$CH$_3$), 2.45-2.75 (m, 12H, COCH$_2$CH$_2$CO), 3.13-3.30 (m, 10H, SiCH$_2$CH$_2$CH$_2$NH and NCH$_2$CH$_2$(CH$_2$)$_{13}$CH$_3$), 3.78-3.83 (m, 18H, CH$_3$CH$_2$OSi), 4.02 (s, 8H, CCH$_2$OCO). The theoretical value of MS is 1594.37, and the found [M]$^+$ is 1595.4.

Example 23

Dihexadecyl amine 31 (6 mmol) and succinic anhydride 32 (12 mmol) were added to dry THF (60 mL) and dissolved upon heating. The solution was stirred for 26 h at room temperature. The solvent was evaporated in vacuu, and the crude product was dissolved in dichloromethane (50 mL). The solution was then washed in turn with 10% aqueous hydrochloric acid and saturated aqueous sodium chloride. After drying, using anhydrous Magnesium sulfate, the solvent was evaporated in vacuum. The crude product was purified with a silica gel column to give a compound 33 with a constructional formula

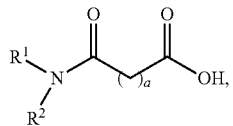

wherein R$^1$ and R$^2$ is C$_{16}$ alkyl, a is 2, and the yield is 78%.

The compound prepared in this embodiment: $^1H$ NMR (400 MHz, CDCl$_3$, TMS): δ=0.88 (t, J=6.6 Hz, 6H, NCH$_2$CH$_2$(CH$_2$)$_{13}$CH$_3$), 1.26 (m, 52H, NCH$_2$CH$_2$(CH$_2$)$_{13}$ CH$_3$), 1.54 (m, 4H, NCH$_2$CH$_2$(CH$_2$)$_{13}$CH$_3$), 2.69 (m, 4H, HOCO(CH$_2$)$_2$CON), 3.15 (t, 2H, J=7.8 Hz, NCH$_2$CH$_2$ (CH$_2$)$_{13}$CH$_3$), 3.32 ppm (t, 2H, J=7.8 Hz, NCH$_2$CH$_2$ (CH$_2$)$_{13}$CH$_3$). The theoretical value of MS is 565.95, and the found [M]$^+$ is 566.9.

Example 24

To the solution of the compound 33 (2 mmol) and a compound 34 (4 mmol) with a constructional formula

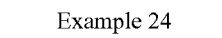

in DMF (40 mL), DCC (4 mmol) and DMAP (1 mmol) were added at room temperature. The reaction mixture was warmed to 55° C. and stirred at this temperature for 16 hours. The solution was concentrated under vacuum and the residue was purified with a silica gel column to give compound 35 ($C_{48}H_{88}NO_8$) with a constructional formula

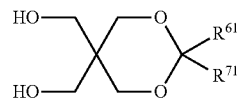

wherein R$^1$ is C$_{16}$ alkyl, R$^2$ is C$_{16}$ alkyl, a is 2, R$^{61}$ is -Ph, R$^{71}$ is —H, and the yield is 43%.

The compound prepared in this embodiment: $^1H$ NMR (CDCl$_3$, 400 MHz) δ: 0.90 (t, J=6.8 Hz, 6H, CH$_3$), 1.25 (s, 52H, NCH$_2$CH$_2$(CH$_2$)$_{13}$CH$_3$) (m, 4H, NCH$_2$CH$_2$(CH$_2$)$_{13}$ CH$_3$), 2.64 (s, 4H, COCH$_2$CH$_2$CO), 3.18-3.30 (m, 4H, NCH$_2$CH$_2$(CH$_2$)$_{13}$CH$_3$), 3.77 (d, J=11.2 Hz, 2H, CH$_2$OH), 3.96 (s, 4H, PhCHOCH$_2$), 4.15 (d, J=11.2 Hz, 2H), 4.60 (s, 1H, OH), 5.42 (s, 1H, PhCHOCH$_2$), 7.35 (d, J=6.4 Hz, 3H, Ph-H), 7.47 (d, J=7.2 Hz, 2H, Ph-H). The theoretical value of MS is 772.19, and the found [M]$^+$ is 772.9, [M+Na]$^+$: 794.9.

Example 25

To the solution of a compound 35 (4 mmol) with a constructional formula

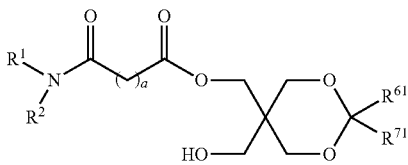

and a compound 411 (16 mmol) with a constructional formula

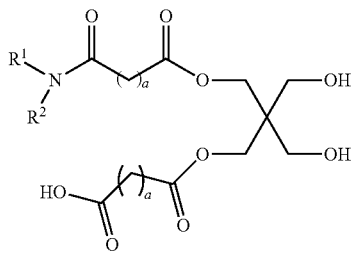

wherein a is 2, and the yield is 52%.

The compound prepared in this embodiment: $^1$H NMR (CDCl$_3$, 400 MHz) δ: 0.88 (t, J=6.8 Hz, 6H, CH$_3$), 1.25-1.30 (m, 52H, NCH$_2$CH$_2$(CH$_2$)$_{13}$CH$_3$), 1.47-1.58 (m, 4H, NCH$_2$CH$_2$(CH$_2$)$_{13}$CH$_3$), 2.64 (d, J=3.6 Hz, 8H, COCH$_2$CH$_2$CO), 3.20-3.29 (m, 4H, NCH$_2$CH$_2$(CH$_2$)$_{13}$CH$_3$), 3.62 (s, 4H, HOCH$_2$), 4.11-4.16 (m, 4H, COCH$_2$CH$_2$COOCH$_2$). The theoretical value of MS is 784.16, the found [M]$^+$ is 785.2, and [M+Na]$^+$ is 807.2.

in dichloromethane (40 mL), DMAP (2 mmol) and triethyl amine (20 mmol) were added. The reaction mixture was stirred at 35° C. for 26 hours. The solution was concentrated under vacuum and the residue was purified with a silica gel column to give a compound 36 (C$_{52}$H$_{89}$NO$_9$) with a constructional formula

Example 27

To the solution of a compound 37 (1 mmol) with a constructional formula

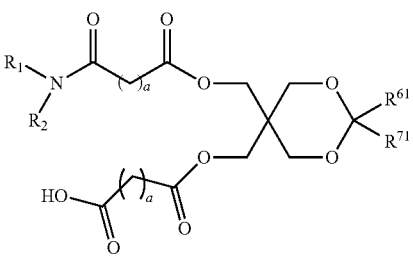

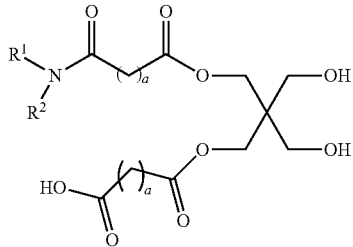

in dichloromethane (40 mL), DCC (1.2 mmol) and compound 38 (1.5 mmol) with a constructional formula

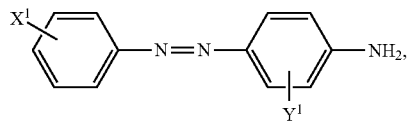

Wherein R$^1$ is C$_{16}$ alkyl, R$^2$ is C$_{16}$ alkyl, a is 2, R$^{61}$ is -Ph, R$^{71}$ is —H, the yield is 86%, $^1$H NMR (CDCl$_3$, 400 MHz) δ: 0.88 (t, J=7.2 Hz, 6H, CH$_3$), 1.26-1.30 (m, 52H, NCH$_2$CH$_2$(CH$_2$)$_{13}$CH$_3$), 1.49-1.60 (m, 4H, NCH$_2$CH$_2$(CH$_2$)$_{13}$CH$_3$), 2.59-2.70 (m, 8H, COCH$_2$CH$_2$CO), 3.23-3.32 (m, 4H, NCH$_2$CH$_2$(CH$_2$)$_{13}$CH$_3$), 3.75-3.93 (m, 4H, PhCHOCH$_2$), 4.18 (d, J=12 Hz, 2H, NCOCH$_2$CH$_2$COOCH$_2$), 4.54 (d, J=24.4 Hz, 2H, HOOCCH$_2$CH$_2$COOCH$_2$), 5.44 (s, 1H, PhCHOCH$_2$), 7.35-7.46 (m, 5H, Ph-H). The theoretical value of MS is 872.26, and the found [M]$^+$ is 873.2, [M+Na]$^+$ is 895.2.

were added, and the mixture was stirred at 30° C. for 48 hours. Then, the solution was concentrated under vacuum and the residue was purified with a silica gel column to give a compound 39 (C$_{57}$H$_{94}$N$_4$O$_8$) with a constructional formula

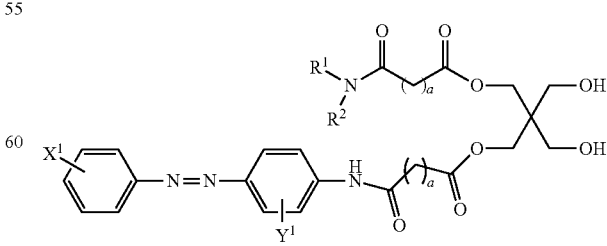

Example 26

In a 250 mL reactor, the compound 36 (1.75 g, 2 mmol) was dissolved in a mixed reaction solvent of methanol and tetrahydrofuran with the volume ratio of 1:3, palladium hydroxide/carbon (0.87 g) was added, hydrogen was access to reach the pressure of 1.0-1.2 MPa, and the above mixture was vigorously stirred at 50° C. for 48 h. The solution was concentrated under vacuum and the residue was purified with a silica gel column to give a compound 37 (C$_{45}$H$_{85}$NO$_9$) with a constructional formula wherein R$^1$ is C$_{16}$ alkyl, R$^2$ is C$_{16}$ alkyl, a is 2, X$^1$ is -Ph, Y$^1$ is —H, the yield is 43.2%.

The compound prepared in this embodiment: $^1$H NMR (CDCl$_3$, 400 MHz) δ: 0.87 (t, J=6.8 Hz, 6H, CH$_3$), 1.21-1.30 (m, 52H, NCH$_2$CH$_2$(CH$_2$)$_{13}$CH$_3$), 1.46-1.57 (m, 4H, NCH$_2$CH$_2$(CH$_2$)$_{13}$CH$_3$), 2.62-2.65 (m, 4H, COCH$_2$CH$_2$CO), 2.73-2.80 (m, 4H, COCH$_2$CH$_2$CO), 3.19-3.28 (m, 4H, NCH$_2$CH$_2$(CH$_2$)$_{13}$CH$_3$), 3.60 (s, 4H, HOCH$_2$), 4.15-4.20 (m, 4H, COCH$_2$CH$_2$COOCH$_2$), 7.42-7.52 (m, 3H, PhH), 7.69 (d, J=8.4 Hz, 2H, PhH), 7.89 (t, J=8.4 Hz, 4H, PhH). The theoretical value of MS is 963.38, and the found [M]$^+$ is 964.4.

Example 28

Under nitrogen atmosphere, to the solution of the compound 39 (1 mmol) in dichloromethane (40 mL), a compound III (2.5 mmol) with a constructional formula

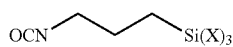

and dibutyltin laurate (0.4 mmol) were added, the mixture was stirred at 55° C. for 48 hours. The solution was then concentrated under vacuum and the residue was purified with a silica gel column to obtain the hybrid lipid compound based on pentaerythritol (C$_{77}$H$_{136}$N$_6$C$_{16}$Si$_2$) with a constructional formula

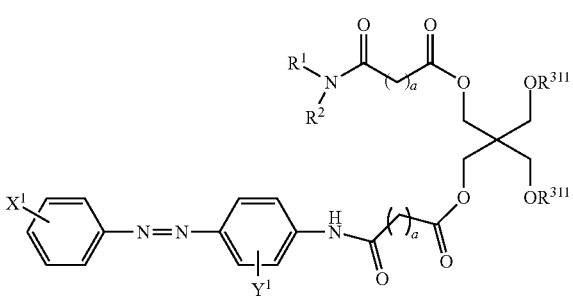

wherein R$^1$ and R$^2$ are C$_{16}$ alkyl chains, a is 2, X$^1$ and Y$^1$ are —H, R$^{311}$ is the group consisting of —CONH(CH$_2$)$_3$Si(X)$_3$. X is ethoxy, the yield is 50.2%.

The compound prepared in this embodiment: $^1$H NMR (CDCl$_3$, 300 MHz) δ: 0.61 (t, J=8.0 Hz, 4H, SiCH$_2$CH$_2$CH$_2$NH), 0.86 (t, J=7.2 Hz, 6H, CH$_3$(CH$_2$)$_{13}$CH$_2$CH$_2$N), 1.09-1.35 (m, 70H, NCH$_2$CH$_2$(CH$_2$)$_{13}$CH$_3$ and SiOCH$_2$CH$_3$), 1.37-1.72 (m, 8H, CH$_3$(CH$_2$)$_{13}$CH$_2$CH$_2$N and SiCH$_2$CH$_2$CH$_2$NH), 2.45-2.71 (m, 8H, COCH$_2$CH$_2$CO), 3.11-3.19 (m, 8H, SiCH$_2$CH$_2$CH$_2$NH and CH$_3$(CH$_2$)$_{13}$CH$_2$CH$_2$N), 3.70-3.83 (m, 12H, SiOCH$_2$CH$_3$), 4.02-4.13 (m, 8H, COOCH$_2$C), 7.46-7.50 (m, 3H, ArH), 7.77-7.80 (m, 2H, ArH), 7.85-7.91 (m, 4H, ArH). The theoretical value of MS is 1458.11, and the found [M]$^+$ is 1459.0.

Example 29

To the solution of the compound 39 (1 mmol) and a compound 411 (6 mmol) with a constructional formula

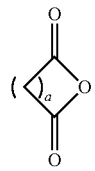

in dichloromethane (40 mL), DMAP (1 mmol) and triethylamine were added. The reaction mixture was stirred at 35° C. for 48 hours. The solution was concentrated under vacuum and the residue was purified with a silica gel column to give a compound 40 (C$_{65}$H$_{102}$N$_4$O$_{14}$) with a constructional formula

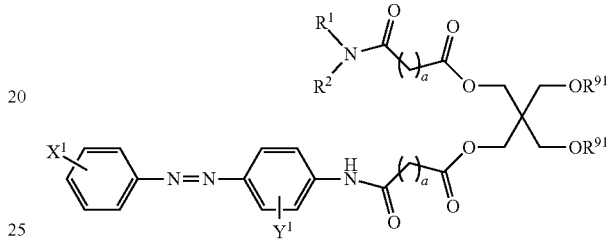

wherein R$^1$ and R$^2$ are C$_{16}$ alkyl chains, a is 2, X$^1$ and Y$^1$ are H, R$^{91}$ is the group consisting of —CO(CH$_2$)$_2$COOH, the yield is 80%.

The compound prepared in this embodiment: $^1$H NMR (CDCl$_3$, 400 MHz) δ: 0.88 (t, J=7.2 Hz, 6H, CH$_3$), 1.22-1.28 (m, 52H, CH$_3$(CH$_2$)$_{13}$CH$_2$CH$_2$N, 1.47-1.57 (m, 4H, CH$_3$(CH$_2$)$_{13}$CH$_2$CH$_2$N), 2.60-2.78 (m, 16H, COCH$_2$CH$_2$CO), 3.20-3.30 (m, 4H, CH$_3$(CH$_2$)$_{13}$CH$_2$CH$_2$N), 4.09-4.14 (m, 8H, COOCH$_2$C), 1.44-7.52 (m, 3H, ArH), 7.68 (d, J=8.4 Hz, 2H, ArH), 7.86-7.90 (m, 4H, ArH). The theoretical value of MS is 1163.52. found [M]$^+$ is 1164.5, and [M+Na]$^+$ is 1186.6

Example 30

To the solution of the compound 40 (0.5 mmol) in dichloromethane (20 mL), DCC (1.2 mmol) and a compound 131 (1.5 mmol) with a constructional formula

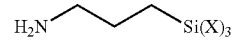

were added and the mixture was stirred at 30° C. for 30 hours. Then the solution was concentrated under vacuum and the residue was purified with a silica gel column to give a hybrid lipid compound based on pentaerythritol (C$_{83}$H$_{144}$N$_6$O$_{18}$Si$_2$) with a constructional formula

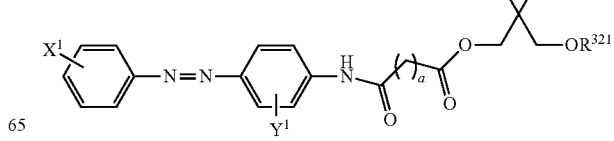

wherein $R^1$ and $R^2$ are $C_{16}$ alkyl chains, a is 2, $X^1$ and $Y^1$ are H, $R^{321}$ is —CO(CH$_2$)$_2$CONH(CH$_2$)$_3$Si(X)$_3$, in which X is ethoxy, the yield is 20%.

The compound prepared in this embodiment: $^1$H NMR (CDCl$_3$, 300 MHz) δ: 0.62 (t, J=8.4 Hz, 4H, SiCH$_2$CH$_2$CH$_2$NH), 0.85-0.88 (m, 6H, CH$_3$(CH$_2$)$_{13}$CH$_2$CH$_2$N), 1.10-1.34 (m, 70H, NCH$_2$CH$_2$(CH$_2$)$_{13}$CH$_3$ and SiOCH$_2$CH$_3$), 1.35-1.70 (m, 8H, CH$_3$(CH$_2$)$_{13}$CH$_2$CH$_2$N and SiCH$_2$CH$_2$CH$_2$NH), 2.42-2.72 (m, 16H, COCH$_2$CH$_2$CO), 3.20-3.25 (m, 8H, SiCH$_2$CH$_2$CH$_2$NH and CH$_3$(CH$_2$)$_{13}$CH$_2$CH$_2$N), 3.69-3.84 (m, 12H, SiOCH$_2$CH$_3$), 4.08-4.17 (m, 8H, COOCH$_2$C), 7.46-7.51 (m, 3H, ArH), 7.73-7.76 (m, 2H, ArH), 7.87-7.90 (m, 4H, ArH). The theoretical value of MS is 1570.23, the found [M]$^+$ is 1571.7, and [M+Na]$^+$ is 1592.6.

Example 31

In a round 20 mL round bottom flask, 4 mg of hybrid lipid prepared in embodiment 30 was dissolved in 5 mL of CHCl$_3$, which was then removed by a nitrogen stream to form a thin film layer on the wall of vial. The film was then dried under vacuum at 35° C. Then, a certain volume of ultrapure water was added to the vial to reach the final concentration of 1 mmol/L. The mixture was ultrasonicated with a probe-type sonicator for 5 min to obtain a solution with a certain turbidity. The resultant solution was incubated at room temperature for 12 h before measurements. Particle size of cerasomes prepared in this embodiment detected by a DLS instrument is about 156 nm, showing narrow particle size distribution, and a polydispersity index of 0.197, consistent with the result observed by scanning electron microscopy. Particle size distribution is shown in FIG. 8, and scanning electron microscopy is shown in FIG. 9.

Example 32

Cerasome solution prepared in the embodiment 31 was diluted to a concentration of 250 µM. Upon irradiation with UV light of 365 nm for different time, the UV/Vis absorption spectra was detected. The result showed an obvious decrease in the absorption intensity of azobenzene unit at about 360 nm and a concurrent increase in the peak at 450 nm. It was evident that trans-to-cis isomerization of azobenzene unit had occurred. UV-visible absorption spectrum is shown in FIG. 10.

Example 33

To the solution of a compound 35 (1 mmol) with a constructional formula

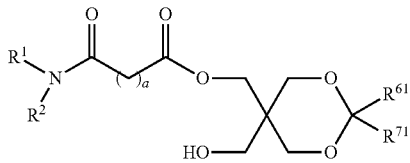

in DMF (40 mL), a compound 141 (2 mmol) with a constructional formula

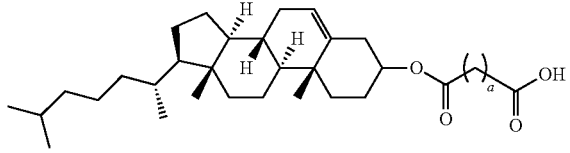

was added, and the mixture was completely dissolved by heating. Then DCC (2 mmol) and DMAP (1 mmol) were in turn added, and the resultant mixture was heated at 55° C. for 20 hours. Later, the solution was concentrated under vacuum and the residue was purified by a silica gel column to give a compound 151 (C$_{79}$H$_{133}$NO$_9$) with a constructional formula

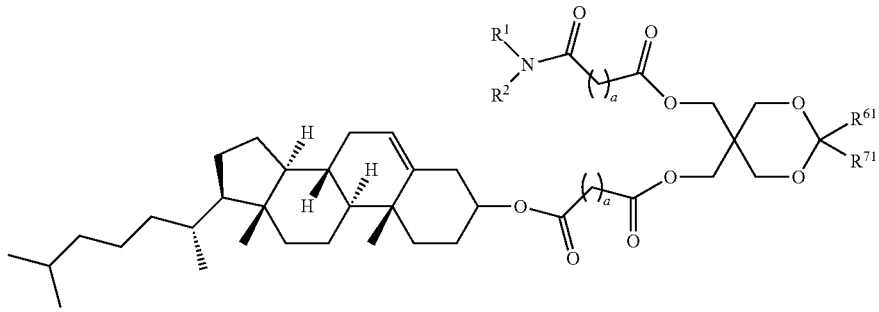

wherein $R^1$ and $R^2$ are $C_{16}$ alkyl chains, a is 2, $R^{61}$ is -Ph, $R^{71}$ is —H, the yield is 80%.

The compound prepared in this embodiment: $^1$H NMR (CDCl$_3$, 400 MHz) δ: 0.85-2.92 (m, 15H, CH$_3$), 0.99 (s, 3H, CH$_3$), 1.09-1.60 (m, 70H), 1.81-1.85 (m, 2H), 2.31 (d, J=7.6 Hz, 2H, CH$_2$), 2.60-2.68 (m, 8H, NCOCH$_2$CH$_2$CO), 3.22-3.28 (m, 4H, NCH$_2$), 3.87-4.51 (m, 8H, OCH$_2$), 4.44-4.45 (m, 1H, COOCHCH$_2$), 5.35 (m, 1H, C=CCH) 5.44 (s, 1H, PhCHOCH$_2$), 7.34-7.48 (m, 5H, Ph-H). The theoretical value of MS: 1240.9. found [M]$^+$: 1241.5, and [M+Na]$^+$: 1263.6.

Example 34

In a 250 mL reactor, the compound 151 (2.48 g, 2 mmol) was dissolved in a mixed reaction solvent of methanol and tetrahydrofuran with the volume ratio of 1:3, palladium hydroxide/carbon (1.24 g) was added, hydrogen was access to reach the pressure of 1.0-1.2 MPa, and the above mixture was vigorously stirred at 50° C. for 48 h. The solution was concentrated under vacuum and the residue was purified by a silica gel column to give a compound 161 (C$_{72}$H$_{129}$NO$_9$) with a constructional formula

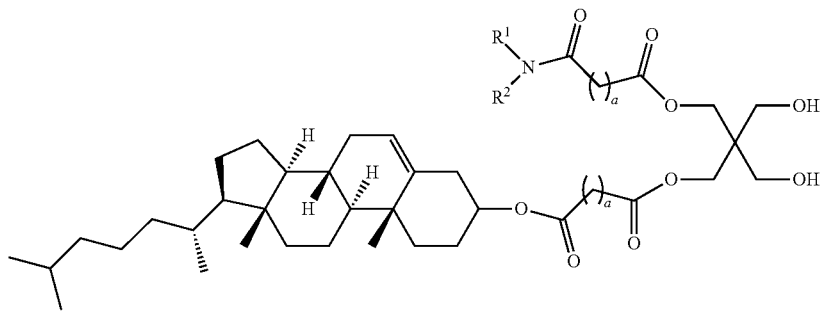

Wherein $R^1$ and $R^2$ are $C_{16}$ alkyl chains, a is 2, and the yield is 52%.

$^1$H NMR (CDCl$_3$, 400 MHz) δ: 0.85-0.92 (m, 15H, CH$_3$), 1.01 (s, 3H, CH$_3$), 1.08-1.60 (m, 70H), 1.81-1.85 (m, 2H), 2.31 (d, J=7.6 Hz, 2H, CH$_2$), 2.62-2.68 (m, 8H, COCH$_2$CH$_2$CO), 3.19-3.28 (m, 4H, NCH$_2$), 3.58 (s, 4H, HOOCH$_2$), 4.16-4.19 (m, 4H, COOCH$_2$), 4.44-4.45 (m, 1H, COOCHCH$_2$), 5.36 (d, J=4 Hz, 1H, C=CH). The theoretical value of MS: 1152.80. found [M]$^+$: 1153.5, and [M+Na]$^+$: 1175.5.

Example 35

Under nitrogen atmosphere, to the solution of the compound 161 (1 mmol) in dichloromethane (40 mL), a compound III (2.5 mmol) with a constructional formula

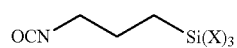

and dibutyltin laurate (0.4 mmol) were added, the mixture was stirred at 55° C. for 48 hours. The solution was then concentrated under vacuum and the residue was purified with a silica gel column to obtain the hybrid lipid compound based on pentaerythritol (C$_{92}$H$_{171}$N$_3$O$_{17}$Si$_2$) with a constructional formula

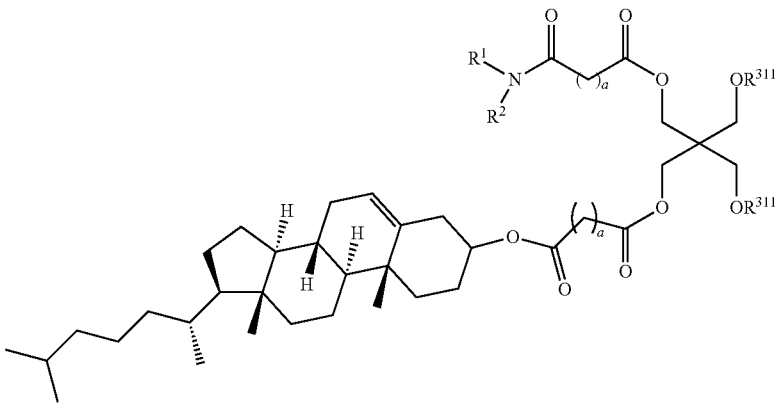

wherein $R^{311}$ is the group consisting of —CONH(CH$_2$)$_3$Si(X)$_3$, in which X is ethoxy, $R^1$ and $R^2$ are $C_{16}$ alkyl chains, a is 2, the yield is 53.2%.

$^1$H NMR (CDCl$_3$, 400 MHz) δ: 0.61 (t, J=8.4 Hz, 4H, SiCH$_2$CH$_2$CH$_2$NH), 0.67 (s, 3H, CH$_3$), 0.86-1.10 (m, 18H, CH$_3$), 1.10-1.35 (m, 89H), 1.45-1.62 (m, 12H), 1.81-2.30 (m, 5H), 2.60-2.65 (m, 8H, COCH$_2$CH$_2$CO), 3.20-3.36 (m, 8H, SiCH$_2$CH$_2$CH$_2$NH and CH$_3$(CH$_2$)$_{13}$CH$_2$CH$_2$N), 3.68-3.83 (m, 12H, SiOCH$_2$CH$_3$), 4.00-4.13 (m, 8H, COOCH$_2$C), 4.61-4.64 (m, 1H, COOCHCH$_2$), 5.38 (d, J=4 Hz, 1H, C=CH). The theoretical value of MS is 1647.52, and found [M]$^+$ is 1648.4.

Example 36

To the solution of the compound 161 (1 mmol) and a compound 411 (6 mmol) with a constructional formula

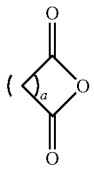

in dichloromethane (40 mL), DMAP (1 mmol) and triethylamine (6 mmol) were added. The reaction mixture was stirred at 35° C. for 48 hours. Later the solution was concentrated under vacuum and the residue was purified with a silica gel column to give a compound 171 ($C_{80}H_{137}NO_{15}$) with a constructional formula

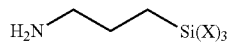

was added and the mixture was stirred at 30° C. for 30 hours. Then the solution was concentrated under vacuum and the residue was purified with a silica gel column to give a hybrid lipid compound based on pentaerythritol ($C_{98}H_{179}N_3O_{19}Si_2$) with a constructional formula

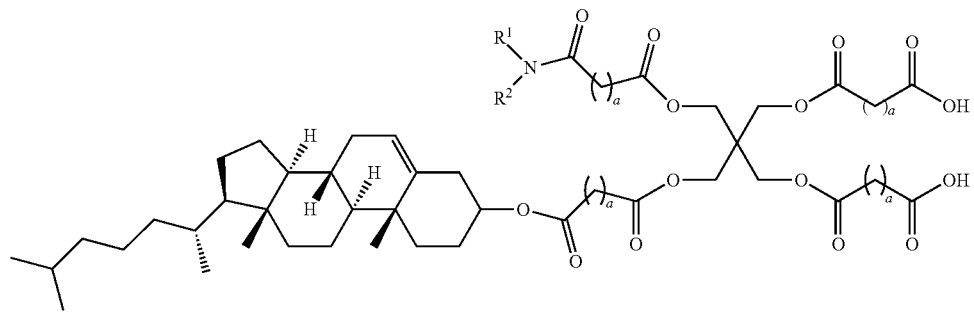

wherein $R^1$ and $R^2$ are $C_{16}$ alkyl chains, a is 2, and the yield is 82%.

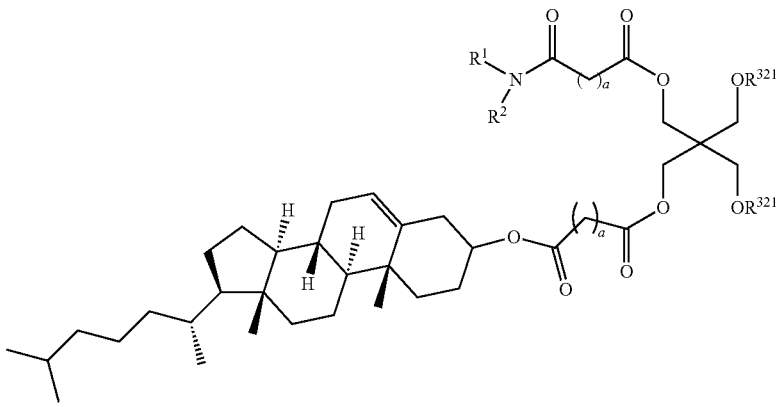

wherein $R^{321}$ is the group consisting of —$CO(CH_2)_2CONH$ $(CH_2)_3Si(X)_3$, X is ethoxy, and the yield is 20%.

$^1$H NMR (CDCl$_3$, 400 MHz) δ: 0.60 (t, J=8.4 Hz, 4H, SiCH$_2$CH$_2$CH$_2$NH), 0.68 (s, 3H, CH$_3$), 0.87-1.08 (m, 18H, CH$_3$), 1.08-1.31 (m, 89H), 1.43-1.59 (m, 12H), 1.84-2.32 (m, 5H), 2.59-2.64 (m, 16H, COCH$_2$CH$_2$CO), 3.20-3.35 (m, 8H, SiCH$_2$CH$_2$CH$_2$NH and CH$_3$(CH$_2$)$_{13}$CH$_2$CH$_2$N), 3.69-3.84 (m, 12H, SiOCH$_2$CH$_3$), 4.08-4.14 (m, 8H, COOCH$_2$C), 4.61-4.64 (m, 1H, COOCHCH$_2$), 5.38 (d, J=4 Hz, 1H, C=CH). The theoretical value of MS is 1759.65, and found [M]$^+$ is 1760.5.

$^1$H NMR (CDCl$_3$, 400 MHz) δ: 0.68 (s, 3H, CH$_3$), 0.87-0.99 (m, 18H, CH$_3$), 1.07 (s, 6H, CH$_3$), 1.10-1.30 (m, 70H), 1.43-1.59 (m, 12H), 1.84-2.03 (m, 5H), 2.32 (d, J=8 Hz, 2H, COOCHCH$_2$), 2.59-2.64 (m, 16H, COCH$_2$CH$_2$CO), 3.22-3.31 (m, 4H, NCH$_2$), 4.08-4.14 (m, 8H, COOCH$_2$C), 4.61-4.64 (m, 1H, COOCHCH$_2$), 5.37 (d, J=4 Hz, 1H, C=CH). The theoretical value of MS is 1352.94. found [M]$^+$ is 1353.7, [M+Na]$^+$ is 1375.8, and [M+K]$^+$ is 1391.7.

Example 37

To the solution of the compound 171 (1 mmol) in dichloromethane (30 mL), DCC (2 mmol) and a compound 131 (2.2 mmol) with a constructional formula Example 38

In a 20 mL round bottom flask, 4 mg of the hybrid lipid compound prepared in embodiment 37 was dissolved in 5 mL of CHCl$_3$, which was then removed by a nitrogen stream to form a thin film layer on the wall of vial. The film was then dried under vacuum at 35° C. Then, certain volume of ultrapure water was added to the vial to reach the final concentration of 1 mmol/L, The mixture was ultrasonicated with a probe-type sonicator for 10 min to obtain a solution with certain turbidity. The resultant solution was incubated at room temperature for 12 h before measurements. Transmittance electron microscopy is shown in FIG. 11.

Example 39

Surfactant Triton X-100 (TX-100) was added into cerasomes prepared from the hybrid lipid in embodiment 38. Size changes of cerasomes were tested, comparing size changes of conventional liposomes made from phospholipids (DSPC) which were used as controls under the same conditions to examine the stability of the cerasome. When 30 times amount of TX-100 solution were added, sizes of cerasomes derived from the hybrid lipid of the present invention remained unchanged, while particle sizes of traditional liposomes from the DSPC decreased to zero in the presence of 5 times amount of TX-100. T his indicates that the vesicles structure have been destroyed, providing strong evidence that liposomes derived from hybrid lipid of the present invention show higher stability than the conventional liposomes. The stability evaluated results of cerasomes are shown in FIG. 12.

Example 40

A compound 37 (1 mmol) with a constructional formula

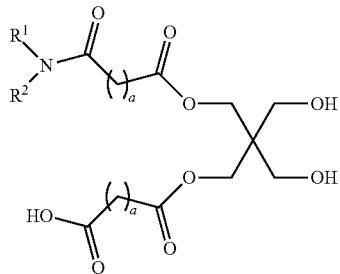

was dissolved in dichloromethane (40 mL), DCC (1.2 mmol) and a compound 41 (1.5 mmol) with a constructional formula

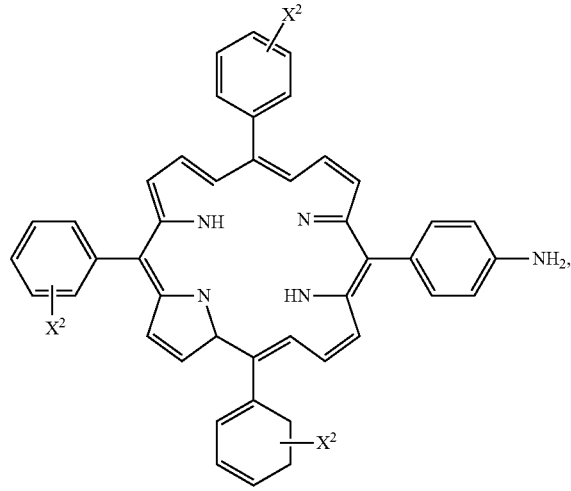

were added, and the mixture was stirred at 30° C. for 48 hours. Then, the solution was concentrated under vacuum and the residue was purified with a silica gel column to get a compound 42 ($C_{89}H_{114}H_6O_8$) with a constructional formula

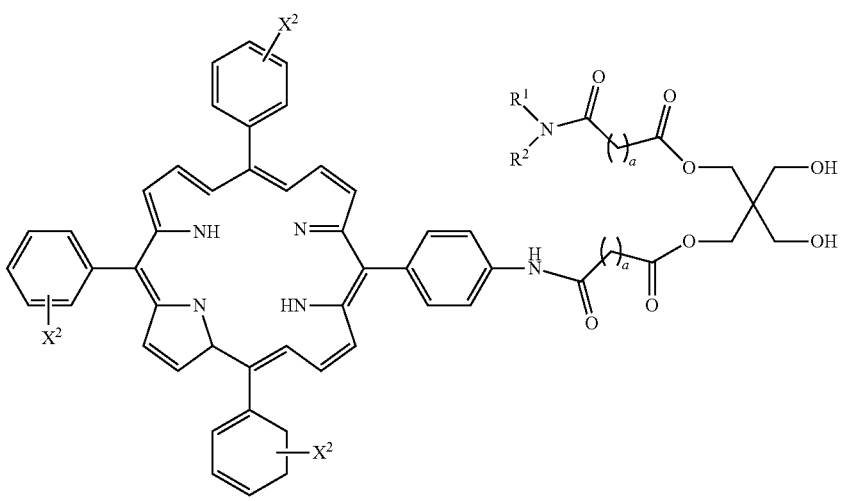

wherein $R^1$ and $R^2$ are the same and are both $C_{16}$ alkyl chains, a is 2, $X^2$ is —H, the yield is 63.0%.

$^1$H NMR (CDCl$_3$, 400 MHz) δ: −2.78 (s, 2H, NH-porphyrin), 0.83-0.88 (m, 6H, NCH$_2$CH$_2$(CH$_2$)$_{13}$CH$_3$), 1.18-1.26 (m, 52H, NCH$_2$CH$_2$(CH$_2$)$_{13}$CH$_3$), 1.48-1.56 (m, 4H, NCH$_2$CH$_2$(CH$_2$)$_{13}$CH$_3$), 2.66-2.90 (m, 8H, COCH$_2$CH$_2$CO), 3.08 (s, 2H, OH), 3.17-3.30 (m, 4H, NCH$_2$CH$_2$(CH$_2$)$_{13}$CH$_3$), 3.67 (s, 4H, HOCH$_2$), 4.24-4.28 (m, 4H, COCH$_2$CH$_2$COOCH$_2$), 7.71-7.79 (m, 9H, ArH), 7.88 (d, J=8.4 Hz, 2H, ArH), 8.14 (d, J=8.0 Hz, 2H, ArH), 8.20 (d, J=5.6 Hz, 6H, ArH), 8.28 (s, 1H, CONH), 8.84 (d, J=6.8 Hz, 4H, ArH). The theoretical value of MS is 1395.89, and found [M]$^+$ is 1396.4.

Example 41

Under nitrogen atmosphere, the compound 42 (1 mmol) was dissolved in dichloromethane (40 mL), then a compound III (2.5 mmol) with a constructional formula

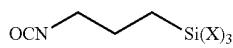

and dibutyltin laurate (0.4 mmol) were added, and the mixture was stirred at 55° C. for 48 hours. Then the solution was concentrated under vacuum and the residue was purified with a silica gel column to obtain the hybrid lipid based on pentaerythritol (C$_{109}$H$_{156}$N$_8$C$_{16}$Si$_2$) with a constructional formula wherein $R^1$ and $R^2$ are the same and are both $C_{16}$ alkyl chains, a is 2, $X^2$ is H, $R^{311}$ is —CONH(CH$_2$)$_3$Si(X)$_3$. X is ethoxy, and the yield is 54.5%.

$^1$H NMR (CDCl$_3$, 400 MHz) δ: −2.77 (s, 2H, NH-porphyrin), 0.60 (t, J=7.4 Hz, 4H, SiCH$_2$CH$_2$CH$_2$NH), 0.83-0.88 (m, 6H, NCH$_2$CH$_2$(CH$_2$)$_{13}$CH$_3$), 1.21-1.30 (m, 52H, NCH$_2$CH$_2$(CH$_2$)$_{13}$CH$_3$), 1.50-1.68 (m, 8H, CH$_3$(CH$_2$)$_{13}$CH$_2$CH$_2$N and SiCH$_2$CH$_2$CH$_2$NH), 2.49-2.69 (m, 8H, COCH$_2$CH$_2$CO), 3.18-3.21 (m, 8H, SiCH$_2$CH$_2$CH$_2$NH and CH$_3$(CH$_2$)$_{13}$CH$_2$CH$_2$N), 3.80-3.84 (m, 12H, SiOCH$_2$CH$_3$), 4.10-4.31 (m, 8H, COOCH$_2$C), 6.19-6.21 (m, 2H, SiCH$_2$CH$_2$CH$_2$NH), 7.77-7.83 (m, 9H, ArH), 7.97-8.00 (m, 2H, ArH), 8.18-8.21 (m, 2H, ArH), 8.25 (d, J=6.0 Hz, 6H, ArH), 8.52-8.65 (m, 1H, ArCONH), 8.85-8.90 (m, 7H, ArH), 9.21 (s, 1H, ArH). The theoretical value of MS is 1890.62, and found [M]$^+$ is 1891.7.

Example 42

The mixture of the compound 42 (1 mmol) and a compound 411 (6 mmol) with a constructional formula

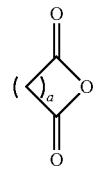

was dissolved in dichloromethane (40 mL), and then DMAP (1 mmol) and triethylamine (6 mmol) were added. The reaction mixture was stirred at 35° C. for 60 hours, was then concentrated under vacuum, amd the residue was purified with a silica gel column to get a compound 44 (C$_{97}$H$_{122}$N$_6$O$_{14}$) with a constructional formula

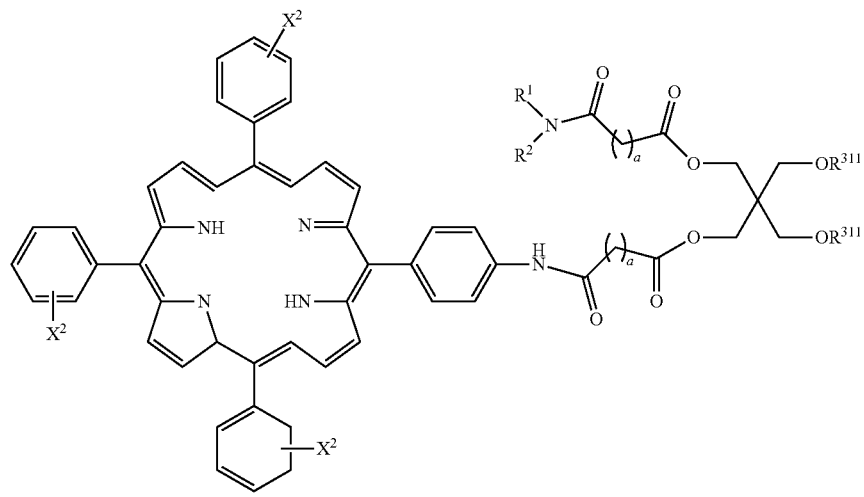

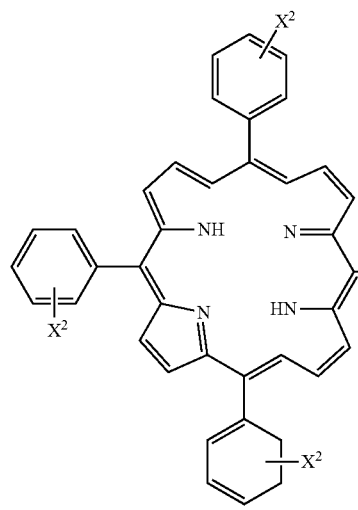

wherein $R^1$ and $R^2$ are the same and are both $C_{16}$ alkyl chains, a is 2, $X^2$ is H, $R^{91}$ is —$CO(CH_2)_2COOH$, and the yield is 85%.

$^1$H NMR (CDCl$_3$, 400 MHz) δ: −2.757 (s, 2H, NH-porphyrin), 0.89 (t, J=7.2 Hz, 6H, CH$_3$), 1.24-1.33 (m, 52H, CH$_3$(CH$_2$)$_{13}$CH$_2$CH$_2$N), 1.50-1.58 (m, 4H, CH$_3$(CH$_2$)$_{13}$CH$_2$CH$_2$N), 2.61-2.78 (m, 16H, COCH$_2$CH$_2$CO), 3.19-3.32 (m, 4H, CH$_a$(CH$_2$)$_{13}$CH$_2$CH$_2$N), 4.18-4.24 (m, 8H, COOCH$_2$C), 7.73-7.81 (m, 9H, ArH), 7.85 (d, J=8.4 Hz, 2H, ArH), 8.15 (d, J=8.4 Hz, 2H, ArH), 8.20-8.25 (m, 7H, ArH and CONH), 8.86 (s, 8H, ArH). The theoretical value of MS is 1595.3, and found [M]$^+$ is 1596.04.

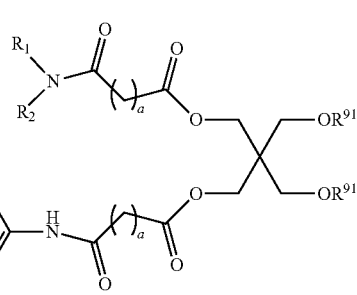

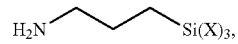

were added, and the mixture was stirred at 30° C. for 48 hours. The mixture was then concentrated under vacuum, and the residue was purified with a silica gel column to get a hybrid lipid compound based on pentaerythritol ($C_{115}H_{164}N_8O_{18}S_{12}$) with a constructional formula

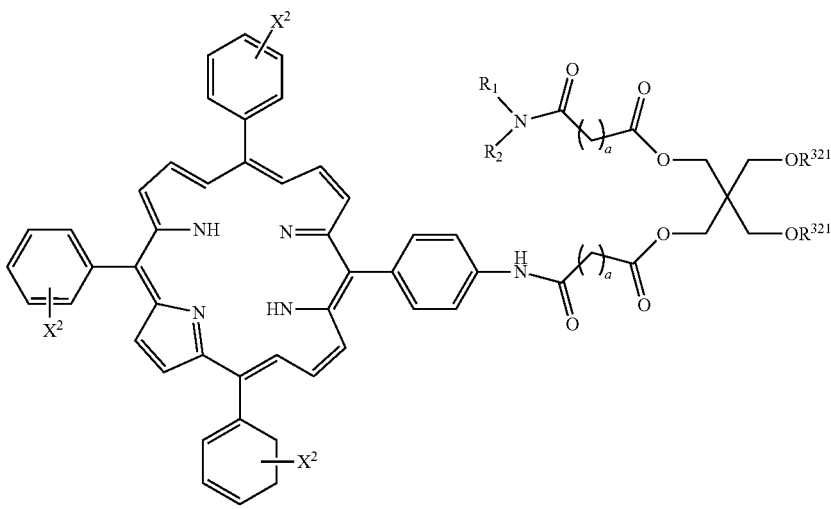

Example 43

The compound 44 (0.5 mmol) was dissolved in dichloromethane (30 mL), and then DCC (1.2 mmol) and a compound 131 (1.5 mmol) with a constructional formula wherein $R^{321}$ is —$CO(CH_2)_2CONH(CH_2)_3Si(X)_3$, X is ethoxy, a is 2, $R^1$ and $R^2$ are the same and are both $C_{16}$ alkyl chains, $X^2$ is H, the yield is 30.3%.

$^{11}$H NMR (CDCl$_3$, 400 MHz) δ: −2.75 (s, 2H, NH-porphyrin), 0.65 (t, J=8.4 Hz, 4H, SiCH$_2$CH$_2$CH$_2$NH), 0.86-0.89 (m, 6H, CH$_3$(CH$_2$)$_{13}$CH$_2$CH$_2$N), 1.19-1.30 (m, 70H, NCH$_2$CH$_2$ (CH$_2$)$_{13}$CH$_3$ and SiOCH$_2$CH$_3$), 1.40-1.67 (m, 8H, CH$_3$(CH$_2$)$_{13}$CH$_2$CH$_2$N and SiCH$_2$CH$_2$CH$_2$NH), 2.49-2.77 (m, 16H, COCH$_2$CH$_2$CO), 3.25-3.31 (m, 8H, SiCH$_2$CH$_2$CH$_2$NH and CH$_3$(CH$_2$)$_{13}$CH$_2$CH$_2$N), 3.78-3.85 (m, 12H, SiOCH$_2$CH$_3$), 4.19-4.29 (m, 8H, COOCH$_2$C), 6.18-6.19 (m, 2H, SiCH$_2$CH$_2$CH$_2$NH), 7.75-7.81 (m, 9H, ArH), 7.98-8.01 (m, 2H, ArH), 8.16-8.19 (m, 2H, ArH), 8.24 (d, J=6.0 Hz, 6H, ArH), 8.50-8.67 (m, 1H, ArCONH), 8.86-8.91 (m, 7H, ArH), 9.20 (s, 1H, ArH). The theoretical value of MS is 1570.23. found [M]$^+$ is 2002.75, and [M+Na]$^+$ is 2003.8.

Example 44

The compound 43 (1 mmol) was dissolved in DMF (30 mL), then a compound 46 (10 mmol) having the formula of MY$^3$ was added, the mixture was refluxed at 160° C. for 24 hours and was then concentrated under vacuum. The residue was purified with a silica gel column to get a hybrid lipid compound based on pentaerythritol (C$_{109}$H$_{154}$N$_8$C$_{16}$Si$_2$Mn) with a constructional formula $^1$H NMR (CDCl$_3$, 400 MHz) δ: 0.63 (t, J=7.3 Hz, 4H, SiCH$_2$CH$_2$CH$_2$NH), 0.80-0.86 (m, 6H, NCH$_2$CH$_2$(CH$_2$)$_{13}$CH$_3$), 1.20-1.34 (m, 52H, NCH$_2$CH$_2$(CH$_2$)$_{13}$CH$_3$), 1.49-1.66 (m, 8H, CH$_3$(CH$_2$)$_{13}$CH$_2$CH$_2$N and SiCH$_2$CH$_2$CH$_2$NH), 2.52-2.71 (m, 8H, COCH$_2$CH$_2$CO), 3.12-3.19 (m, 8H, SiCH$_2$CH$_2$CH$_2$NH and CH$_3$(CH$_2$)$_{13}$CH$_2$CH$_2$N), 3.79-3.81 (m, 12H, SiOCH$_2$CH$_3$), 4.05-4.19 (m, 8H, COOCH$_2$C), 6.13-6.18 (m, 2H, SiCH$_2$CH$_2$CH$_2$NH), 7.65-7.76 (m, 9H, ArH), 7.95-8.02 (m, 2H, ArH), 8.13-8.18 (m, 2H, ArH), 8.30 (d, J=6.0 Hz, 6H, ArH), 8.51-8.62 (m, 1H, ArCONH), 8.87-8.92 (m, 7H, ArH), 9.18 (s, 1H, ArH). The theoretical value of MS is 1943.54, and found [M]$^+$ is 1944.6.

Example 45

The compound 45 (1 mmol) was dissolved in chloroform (30 mL), then a compound 46 (12 mmol) having the formula of MY$^3$ was added, the mixture was refluxed at 70° C. for 48

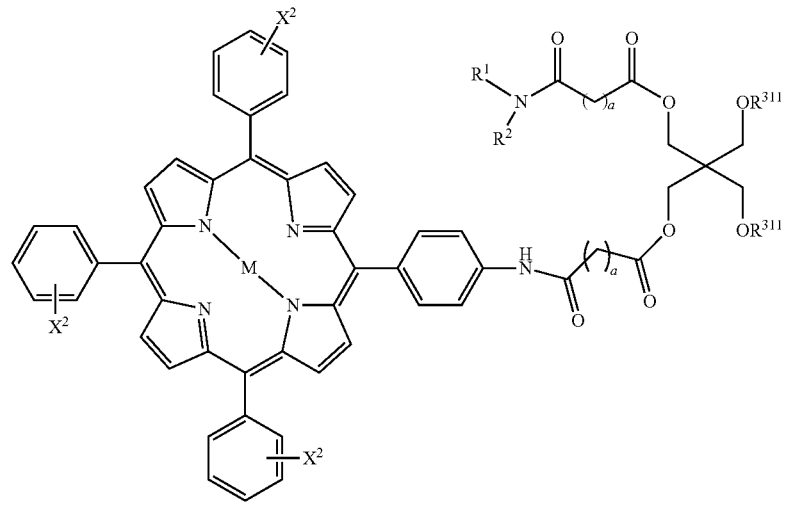

wherein M is the metal ion Manganese (Mn), a is 2, R$^1$ and R$^2$ are the same and are both C$_{16}$ alkyl chains, X$^2$ is H, R$^{311}$ is —CONH(CH$_2$)$_3$Si(X)$_3$, X is ethoxy, the yield is 85.0%, and Y$^3$ is —Cl.

hours and was then concentrated under vacuum. The residue was purified with a silica gel column to get a hybrid lipid compound based on pentaerythritol (C$_{115}$H$_{162}$N$_8$O$_{18}$Si$_2$Zn) with a constructional formula

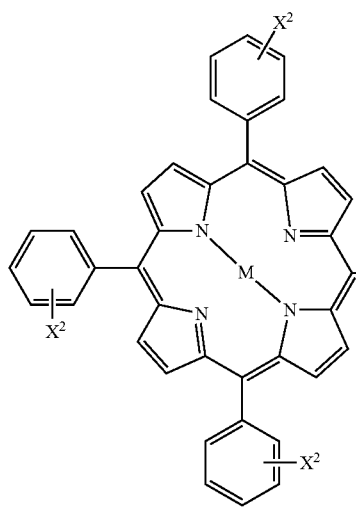
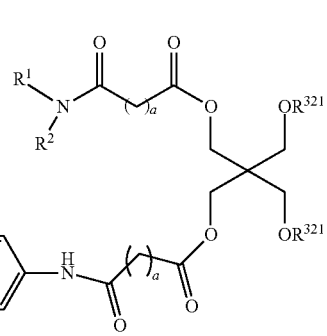

wherein M is the Zinc metal ion (Zn), a is 2, $R^1$ and $R^2$ are the same and are both $C_{16}$ alkyl chains, $X^2$ is H, $R^{321}$ is —CO$(CH_2)_2CONH(CH_2)_3Si(X)_3$, X is ethoxy, the yield is 90.0%, $Y^3$ is —Cl.

$^1$H NMR (CDCl$_3$, 400 MHz) a: 0.66 (t, J=8.4 Hz, 4H, SiCH$_2$CH$_2$CH$_2$NH), 0.83-0.87 (m, 6H, CH$_3$(CH$_2$)$_{13}$CH$_2$CH$_2$N), 1.15-1.28 (m, 70H, NCH$_2$CH$_2$(CH$_2$)$_{13}$CH$_3$ and SiOCH$_2$CH$_3$), 1.41-1.68 (m, 8H, CH$_3$(CH$_2$)$_{13}$CH$_2$CH$_2$N and SiCH$_2$CH$_2$CH$_2$NH), 2.45-2.73 (m, 16H, COCH$_2$CH$_2$CO), 3.21-3.30 (m, 8H, SiCH$_2$CH$_2$CH$_2$NH and CH$_3$(CH$_2$)$_{13}$CH$_2$CH$_2$N), 3.76-3.83 (m, 12H, SiOCH$_2$CH$_3$), 4.15-4.27 (m, 8H, COOCH$_2$C), 6.15-6.18 (m, 2H, SiCH$_2$CH$_2$CH$_2$NH), 7.72-7.79 (m, 9H, ArH), 7.97-8.04 (m, 2H, ArH), 8.13-8.16 (m, 2H, ArH), 8.25 (d, J=6.0 Hz, 6H, ArH), 8.55-8.63 (m, 1H, ArCONH), 8.84-8.88 (m, 7H, ArH), 9.17 (s, 1H, ArH). Theoretical value of MS is 2066.14, and found [M]$^+$ is 2067.1.

Example 46

In a 20 mL round bottom flask, 4 mg of hybrid lipid prepared in embodiment 43 was dissolved in 5 mL CHCl$_3$, which was then evaporated under vacuum to form a thin film layer on the wall of vial. The film was later dried under vacuum at 35° C. to remove CHCl$_3$. Then, a certain volume of ultrapure water was added to the flask to make the film reach the final concentration of 1 mmol/L and was then ultrasonicated with a probe-type sonicator for 10 min to obtain a solution with certain turbidity. The solution was incubated at room temperature for 12 h to form the corresponding cerasomes. The particle size of cerasomes prepared in this embodiment detected by a DLS instrument, is about 125 nm and with narrow particle size distribution, polydispersity index is 0.210, which is consistent with the result observed by transmittance electron microscopy. Particle size distribution is shown in FIG. 13, and transmittance electron microscopy is shown in FIG. 14.

Example 47

Hybrid lipid compound 42 prepared in embodiment 43 was dissolved in chloroform to obtain a solution with the concentration of 30 uM. A UV-visible spectrophotometer was used to test its absorption spectra, and the result is shown in FIG. 15. Cerasomes prepared in embodiment 46 were diluted to obtain a solution with the concentration of 25 uM. A UV-visible spectrophotometer was used to test its absorption spectra, and the result is also shown in FIG. 15. The results show that cerasomes prepared from hybrid lipid compounds still have characteristic absorption peaks of the original functional groups of porphyrin.

Example 48

Surfactant Triton X-100 (TX-100) was added into cerasomes prepared in embodiment 46. Size changes of cerasomes were tested, comparing size changes of conventional liposomes made from phospholipids (DSPC) which were used as controls under the same conditions to examine the stability of the cerasomes. When 35 times amount of TX-100 solution was added, sizes of cerasomes derived from the hybrid lipid of the present invention remained unchanged, while particle sizes of traditional liposomes from the DSPC were almost decreased to zero in the presence of 5 times amount of TX-100. This indicates that the vesicles structure have been destroyed, providing strong evidence that cerasomes derived from hybrid lipid compounds of the present invention show higher stability than the conventional liposomes. The stability evaluated results of cerasomes is shown in FIG. 16.

Example 49

The mixture of the compound 33 (2 mmol) and a compound 47 (4 mmol) with a constructional formula

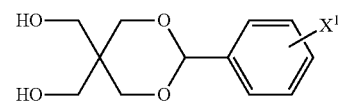

was dissolved in DMF (40 mL), and then DCC (4 mmol) and DMAP (1 mmol) were added. The reaction mixture was warmed to 55° C. and stirred at this temperature for 16 hours. The solution was then concentrated under vacuum to remove the solvent, and the residue was purified with a silica gel column to get a compound 48 ($C_{48}H_{85}NO_6$) with a constructional formula

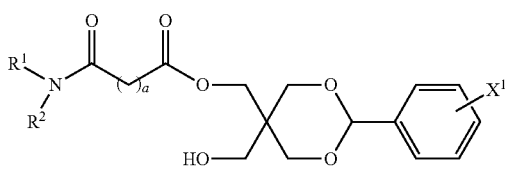

Wherein a is 2, $R^1$ and $R^2$ are the same and are both $C_{16}$ alkyl chains, $X^1$ is H, the yield is 43%.

$^1$H NMR (CDCl$_3$, 400 MHz) δ: 0.90 (t, J=6.8 Hz, 6H, CH$_3$), 1.25 (s, 52H, NCH$_2$CH$_2$(CH$_2$)$_{13}$CH$_3$) (m, 4H, NCH$_2$CH$_2$(CH$_2$)$_{13}$CH$_3$), 2.64 (s, 4H, COCH$_2$CH$_2$CO), 3.18-3.30 (m, 4H, NCH$_2$CH$_2$(CH$_2$)$_{13}$CH$_3$), 3.77 (d, J=11.2 Hz, 2H, CH$_2$OH), 3.96 (s, 4H, PhCHOCH$_2$), 4.15 (d, J=11.2 Hz, 2H), 4.60 (s, 1H, OH), 5.42 (s, 1H, PhCHOCH$_2$), 7.35 (d, J=6.4 Hz, 3H, Ph-H), 7.47 (d, J=7.2 Hz, 2H, Ph-H). Theoretical value of MS is 772.19. found [M]$^+$ is 772.9 and [M+Na]$^+$ is 794.9.

Example 50

Under nitrogen atmosphere, the compound of 48 (1 mmol) was dissolved in dichloromethane (40 mL), and then a compound III (1.25 mmol) with a constructional formula

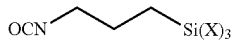

and dibutyltin laurate (0.4 mmol) were added. The mixture was stirred at 55° C. for 48 hours, then concentrated under vacuum to remove the solvent, and the residue was purified with a silica gel column to obtain the hybrid lipid compound based on pentaerythritol (C$_{58}$H$_{106}$N$_2$O$_{10}$Si) with a constructional formula

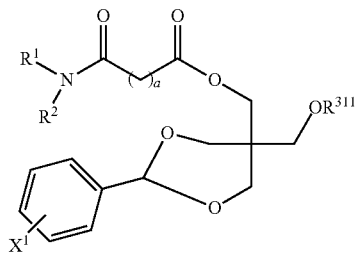

wherein $R^1$ and $R^2$ are $C_{16}$ alkyl chains, $X^1$ is H, $R^{311}$ is the group consisting of —CONH(CH$_2$)$_3$Si(X)$_3$. X is ethoxy, the yield is 52.3%.

$^1$H NMR (CDCl$_3$, 400 MHz) δ: 0.60 (t, J=8.0 Hz, 2H, SiCH$_2$CH$_2$CH$_2$NH), 0.87 (t, J=7.2 Hz, 6H, CH$_3$(CH$_2$)$_{13}$CH$_2$CH$_2$N), 1.19-1.27 (m, 61H, NCH$_2$CH$_2$(CH$_2$)$_{13}$CH$_3$ and SiOCH$_2$CH$_3$), 1.45-1.57 (m, 6H, CH$_3$(CH$_2$)$_{1-3}$CH$_2$CH$_2$N and SiCH$_2$CH$_2$CH$_2$NH), 2.50-2.57 (m, 4H, COCH$_2$CH$_2$CO), 2.97-3.19 (m, 6H, SiCH$_2$CH$_2$CH$_2$NH and CH$_3$(CH$_2$)$_{13}$CH$_2$CH$_2$N), 3.71-3.85 (m, 6H, SiOCH$_2$CH$_3$), 3.90-4.01 (m, 8H, COOCH$_2$C), 5.42 (s, 1H, Ph-CH), 7.33-7.46 (m, 5H, ArH). Theoretical value of MS: 1019.56, and found [M]: 1020.5.

Example 51

The mixture of the compound 48 (4 mmol) and a compound 411 (16 mmol) with a constructional formula

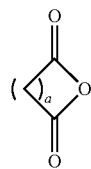

was dissolved in dichloromethane (40 mL), and then DMAP (2 mmol) and triethylamine (20 mmol) were added. The reaction mixture was stirred at 35° C. for 26 hours and was then concentrated under vacuum to remove the solvent, and the residue was purified with a silica gel column to get a compound 49 (C$_{52}$H$_{89}$NO$_9$) with a constructional formula

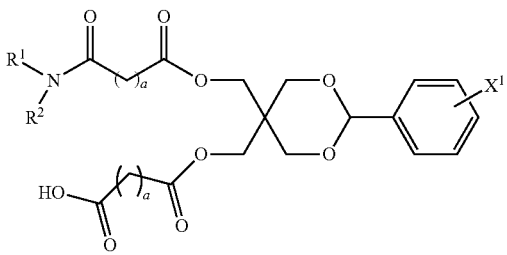

wherein a is 2, $R^1$ and $R^2$ are the same and are both $C_{16}$ alkyl chains, $X^1$ is H, the yield is 86%.

$^1$H NMR (CDCl$_3$, 400 MHz) δ: 0.88 (t, J=7.2 Hz, 6H, CH$_3$), 1.26-1.30 (m, 52H, NCH$_2$CH$_2$(CH$_2$)$_{13}$CH$_3$), 1.49-1.60 (m, 4H, NCH$_2$CH$_2$(CH$_2$)$_{13}$CH$_3$), 2.59-2.70 (m, 8H, COCH$_2$CH$_2$CO), 3.23-3.32 (m, 4H, NCH$_2$CH$_2$(CH$_2$)$_{13}$CH$_3$), 3.75-3.93 (m, 4H, PhCHOCH$_2$), 4.18 (d, J=12 Hz, 2H, NCOCH$_2$CH$_2$COOCH$_2$), 4.54 (d, J=24.4 Hz, 2H, HOOCCH$_2$CH$_2$COOCH$_2$), 5.44 (s, 1H, PhCHOCH$_2$), 7.35-7.46 (m, 5H, Ph-H). Theoretical value of MS is 872.26. found [M]$^+$ is 873.2 and [M+Na]$^+$ is 895.2.

Example 52

The compound 49 (0.5 mmol) was dissolved in dichloromethane (30 mL), then DCC (1.2 mmol) and a compound 131 (1.5 mmol) with a constructional formula

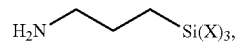

were added. The mixture was stirred at 30° C. for 30 hours and then was concentrated under vacuum to remove the solvent, and the residue was purified with a silica gel column to get a hybrid lipid compound based on pentaerythritol (C$_{81}$H$_{110}$N$_2$O$_{11}$Si) with a constructional formula

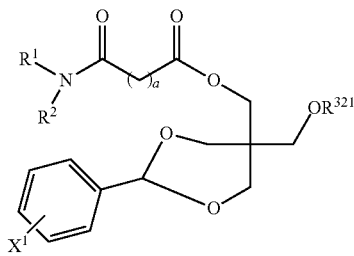

wherein a is 2, $R^1$ and $R^2$ are the same and are both $C_{16}$ alkyl chains, $X^1$ is H, $R^{321}$ is —CO(CH$_2$)$_2$CONH(CH$_2$)$_3$Si(X)$_3$, X is ethoxy, the yield is 20%.

$^1$H NMR (CDCl$_3$, 400 MHz) δ: 0.61 (t, J=8.0 Hz, 2H, SiCH$_2$CH$_2$CH$_2$NH), 0.88 (t, J=7.2 Hz, 6H, CH$_3$(CH$_2$)$_{13}$CH$_2$CH$_2$N), 1.20-1.26 (m, 61H, NCH$_2$CH$_2$(CH$_2$)$_{13}$CH$_3$ and SiOCH$_2$CH$_3$), 1.47-1.58 (m, 6H, CH$_3$(CH$_2$)$_{13}$CH$_2$CH$_2$N and SiCH$_2$CH$_2$CH$_2$NH), 2.44-2.67 (m, 8H, COCH$_2$CH$_2$CO), 3.11-3.19 (m, 6H, SiCH$_2$CH$_2$CH$_2$NH and CH$_3$(CH$_2$)$_{13}$CH$_2$CH$_2$N), 3.69-3.75 (m, 6H, SiOCH$_2$CH$_3$), 3.79-4.47 (m, 8H, COOCH$_2$C), 5.43 (s, 1H, Ph-CH), 7.34-7.45 (m, 5H, ArH). Theoretical value of MS is 1075.62 and found [M]$^+$ is 1076.5.

Example 53

In a 250 mL reactor, the compound 49 (1.75 g, 2 mmol) was dissolved in a mixed reaction solvent of methanol and tetrahydrofuran with the volume ratio of 1:3, palladium hydroxide/carbon (0.87 g) was then added, hydrogen was accessed to reach the pressure of 1.0-1.2 MPa. The above mixture was vigorously stirred at 50° C. for 48 h and then was concentrated under vacuum to remove the solvent, and the residue was purified with a silica gel column to get a compound 37 (C$_{45}$H$_{85}$NO$_9$) with a constructional formula

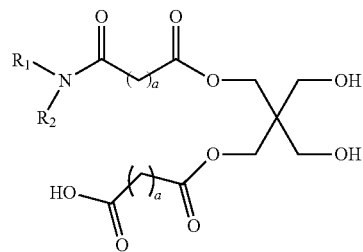

wherein a is 2, $R^1$ and $R^2$ are the same and are both $C_{16}$ alkyl chains, the yield is 52%.

$^1$H NMR (CDCl$_3$, 400 MHz) δ: 0.88 (t, J=6.8 Hz, 6H, CH$_3$), 1.25-1.30 (m, 52H, NCH$_2$CH$_2$(CH$_2$)$_{13}$CH$_3$), 1.47-1.58 (m, 4H, NCH$_2$CH$_2$(CH$_2$)$_{13}$CH$_3$), 2.64 (d, J=3.6 Hz, 8H, COCH$_2$CH$_2$CO), 3.20-3.29 (m, 4H, NCH$_2$CH$_2$(CH$_2$)$_{13}$CH$_3$), 3.62 (s, 4H, HOCH$_2$), 4.11-4.16 (m, 4H, COCH$_2$CH$_2$COOCH$_2$). Theoretical value of MS is 784.16. found [M]$^+$ is 785.2 and [M+Na]$^+$ is 807.2.

Example 54

The compound 37 (0.5 mmol) was dissolved in 30 mL dichloromethane, and then DCC (1.2 mmol) and a compound 131 (1.5 mmol) with a constructional formula

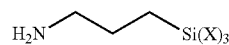

were added. The mixture was stirred at 30° C. for 30 hours and then was concentrated under vacuum to remove the solvent, and the residue was purified with a silica gel column to get a hybrid lipid compound 50 based on pentaerythritol (C$_{54}$H$_{106}$N$_2$O$_{11}$Si) with a constructional formula

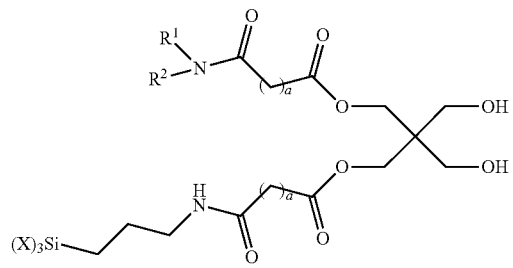

wherein a is 2, $R^1$ and $R^2$ are the same and are both $C_{16}$ alkyl chains, X is ethoxy, the yield is 35%.

$^1$H NMR (CDCl$_3$, 400 MHz) δ: 0.61 (t, J=8.0 Hz, 2H, SiCH$_2$CH$_2$CH$_2$NH), 0.88 (t, J=7.2 Hz, 6H, CH$_3$(CH$_2$)$_{13}$CH$_2$CH$_2$N), 1.20-1.26 (m, 61H, NCH$_2$CH$_2$(CH$_2$)$_{13}$CH$_3$ and SiOCH$_2$CH$_3$), 1.47-1.58 (m, 6H, CH$_3$(CH$_2$)$_{13}$CH$_2$CH$_2$N and SiCH$_2$CH$_2$CH$_2$NH), 2.49-2.63 (m, 8H, COCH$_2$CH$_2$CO), 3.21-3.25 (m, 6H, SiCH$_2$CH$_2$CH$_2$NH and CH$_3$(CH$_2$)$_{13}$CH$_2$CH$_2$N), 3.58-3.60 (m, 4H, HOCH2), 3.69-3.85 (m, 6H, SiOCH$_2$CH$_3$), 4.11-4.17 (m, 4H, COOCH$_2$C). Theoretical value of MS is 987.51 and found [M]$^+$ is 988.4.

Example 55

The mixture of the compound 50 (4 mmol) and a compound 411 (16 mmol) with a constructional formula

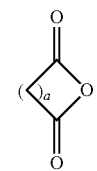

were dissolved in 40 mL dichloromethane, and then DMAP (2 mmol) and triethylamine (20 mmol) were added. The reaction mixture was stirred at 35° C. for 26 hours and then was concentrated under vacuum to remove the solvent, and the residue was purified with a silica gel column to get a hybrid lipid compound (C$_{62}$H$_{114}$N$_2$O$_{17}$Si) with a constructional formula

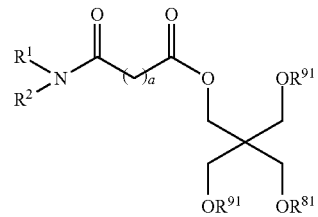

wherein a is 2, $R^1$ and $R^2$ are the same and are both $C_{16}$ alkyl chains, $R^{91}$ is —CO(CH$_2$)$_2$COOH; $R^{81}$ is —CO(CH$_2$)$_2$CONH(CH$_2$)$_3$Si(X)$_3$ and X is ethoxy. The yield is 56%.

$^1$H NMR (CDCl$_3$, 400 MHz) δ: 0.61 (t, J=8.0 Hz, 2H, SiCH$_2$CH$_2$CH$_2$NH), 0.88 (t, J=7.2 Hz, 6H, CH$_3$(CH$_2$)$_{13}$CH$_2$CH$_2$N), 1.18-1.27 (m, 61H, NCH$_2$CH$_2$(CH$_2$)$_{13}$CH$_3$ and SiOCH$_2$CH$_3$), 1.48-1.57 (m, 6H, CH$_3$(CH$_2$)$_{13}$CH$_2$CH$_2$N and SiCH$_2$CH$_2$CH$_2$NH), 2.48-2.63 (m, 16H, COCH$_2$CH$_2$CO), 3.20-3.26 (m, 6H, SiCH$_2$CH$_2$CH$_2$NH and CH$_3$(CH$_2$)$_{13}$CH$_2$CH$_2$N), 3.70-3.84 (m, 6H, SiOCH$_2$CH$_3$), 4.00-4.07 (m, 4H, COOCH$_2$C). Theoretical value of MS is 1187.66, and found $[M]^+$ is 1188.7.

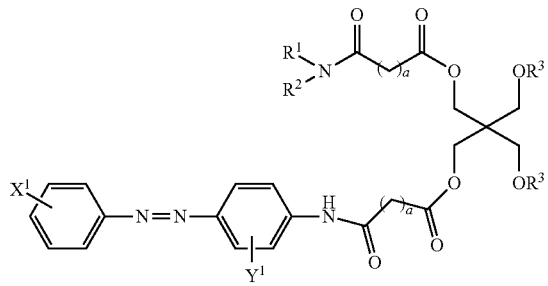

Example 56

4 mg of hybrid lipid compound prepared in embodiment 52 and 4 mg of hybrid lipid compound prepared in embodiment 55 were separately put in a 20 mL round bottom flask and dissolved in 5 mL CHCl$_3$, which was then evaporated under vacuum to form a thin film layer on the wall of vial. The film was later dried under vacuum at 35° C. to remove CHCl$_3$. Then, a certain volume of ultrapure water was added to the flask to make the film reach the final concentration of μmol/L and was then ultrasonicated with a probe-type sonicator for 5 min to obtain a solution with certain turbidity. The solution was incubated at room temperature for 12 h to form the corresponding cerasomes. Transmittance electron microscopy images of cerasome prepared in embodiment 52 are shown in FIG. 17, and transmittance electron microscopy images of cerasome prepared in embodiment 55 are shown in FIG. 18.

What is claimed is:

1. A hybrid lipid compound based on pentaerythritol with a constructional formula

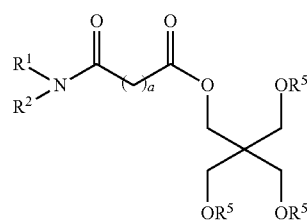

wherein:

$R^1$ is $C_6$-$C_{18}$ alkyl; $R^2$ is $C_6$-$C_{18}$ alkyl; $R^5$ is one among the group consisting of —CO(CH$_2$)$_5$N(CH$_3$)$_2$(CH$_2$)$_3$Si(X)$_3$Y, —CO(CH$_2$)$_2$CONH(CH$_2$)$_3$Si(X)$_3$, —CO(CH$_2$)$_3$CONH(CH$_2$)$_3$Si(X)$_3$ and —CONH(CH$_2$)$_3$Si(X)$_3$, in which X is ethoxy or methoxy, Y is halogen group; and a is 2 or 3.

2. A hybrid lipid compound based on pentaerythritol with a constructional formula wherein:

$R^1$ is $C_6$-$C_{18}$ alkyl; $R^2$ is $C_6$-$C_{18}$ alkyl; $R^3$ is one among the group consisting of —CO(CH$_2$)$_2$CONH(CH$_2$)$_3$Si(X)$_3$, —CO(CH$_2$)$_3$CONH(CH$_2$)$_3$Si(X)$_3$ and —CONH(CH$_2$)$_3$Si(X)$_3$, in which X is ethoxy or methoxy; a is 2 or 3; $X^1$ is one among the group consisting of —H, —CH$_3$, CH$_3$O—, halogenated group and —NO$_2$; $Y^1$ is one among the group —H, —CH$_3$, CH$_3$O— and halogenated group.

3. The hybrid lipid compound of claim 2, wherein when $Y^1$ is attached at the 2-position to the azobenzene unit, $Y^1$ is —H or halogenated group; when $Y^1$ is attached at the 3-position of the azobenzene unit, $Y^1$ is one among the group consisting of —H, —CH$_3$ and CH$_3$O—.

4. A hybrid lipid compound based on pentaerythritol with a constructional formula

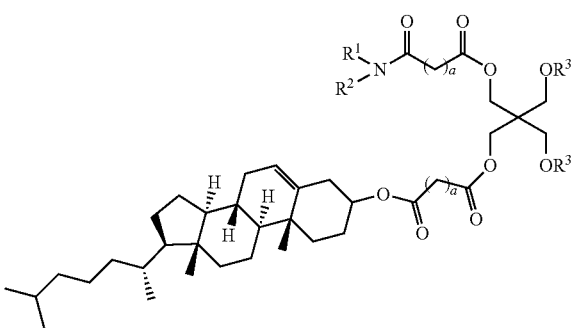

wherein:

$R^1$ is $C_6$-$C_{18}$ alkyl; $R^2$ is $C_6$-$C_{18}$ alkyl; $R^3$ is one among the group consisting of —CO(CH$_2$)$_2$CONH(CH$_2$)$_3$Si(X)$_3$, —CO(CH$_2$)$_3$CONH(CH$_2$)$_3$Si(X)$_3$ and —CONH(CH$_2$)$_3$Si(X)$_3$, in which X is ethoxy or methoxy; and a is 2 or 3.

5. A hybrid lipid compound based on pentaerythritol with a constructional formula

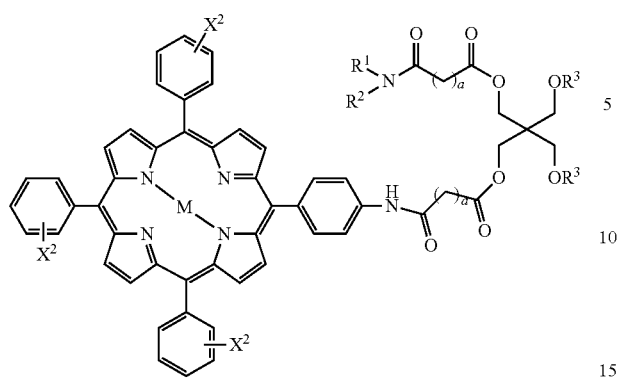

wherein:
$R^1$ is $C_6$-$C_{18}$ alkyl; $R^2$ is $C_6$-$C_{18}$ alkyl; $R^3$ is one among the group consisting of —CO(CH$_2$)$_2$CONH(CH$_2$)$_3$Si(X)$_3$, —CO(CH$_2$)$_3$CONH(CH$_2$)$_3$Si(X)$_3$ and —CONH(CH$_2$)$_3$Si(X)$_3$, in which X is ethoxy or methoxy; a is 2 or 3; $X^2$ is one among the group consisting of —H, —CH$_3$, CH$_3$O— and halogenated group; M is the metal ion coordinated with porphyrin ring which is one among the group consisting of Iron, Zinc, Magnesium, Manganese, Cobalt, Copper, Molybdenum, Chromium, Gadolinium, Nickel, Vanadium, Aluminum, Gallium and Iridium.

6. A hybrid lipid based on pentaerythritol with a constructional formula

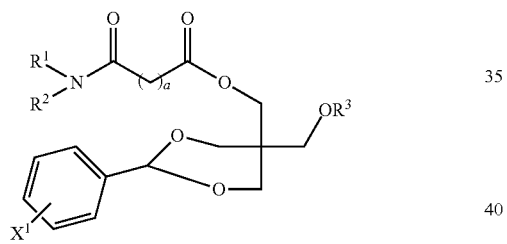

wherein:
$R^1$ is $C_6$-$C_{18}$ alkyl; $R^2$ is $C_6$-$C_{18}$ alkyl; $R^3$ is one among the group consisting of —CO(CH$_2$)$_2$CONH(CH$_2$)$_3$Si(X)$_3$, —CO(CH$_2$)$_3$CONH(CH$_2$)$_3$Si(X)$_3$ and —CONH(CH$_2$)$_3$Si(X)$_3$, in which X is ethoxy or methoxy; a is 2 or 3; $X^1$ is one among the group consisting of —H, —CH$_3$, CH$_3$O—, halogenated group and —NO$_2$.

7. A hybrid lipid compound based on pentaerythritol with a constructional formula

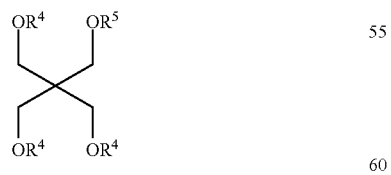

wherein:
$R^4$ is $C_6$-$C_{18}$ alkyl; $R^5$ is one among the group consisting of —CO(CH$_2$)$_5$N(CH$_3$)$_2$(CH$_2$)$_3$Si(X)$_3$Y, —CO(CH$_2$)$_2$CONH(CH$_2$)$_3$Si(X)$_3$, —CO(CH$_2$)$_3$CONH(CH$_2$)$_3$Si(X)$_3$ and —CONH(CH$_2$)$_3$Si(X)$_3$, in which X is ethoxy or methoxy and Y is halogenated group.

8. A hybrid lipid compound based on pentaerythritol with a constructional formula

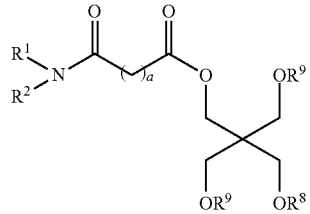

wherein:
$R^1$ is $C_6$-$C_{18}$ alkyl; $R^2$ is $C_6$-$C_{18}$ alkyl, $R^8$ is one among the group consisting of CO(CH$_2$)$_2$CONH(CH$_2$)$_3$Si(X)$_3$, —CO(CH$_2$)$_3$CONH(CH$_2$)$_3$Si(X)$_3$ and —CONH(CH$_2$)$_3$Si(X)$_3$, in which X is ethoxy or methoxy; $R^9$ is —CO(CH$_2$)$_2$COOH or —CO(CH$_2$)$_3$COOH; and a is 2 or 3.

9. A method for making the hybrid lipid compound of claim 1 comprises following steps:

1) forming a compound 1 with a constructional formula

by reacting alkyl amines and alkyl bromide under heating reflux through substitution reaction, wherein the alkyl amines is $R^1$—NH$_2$ and the alkyl bromide is $R^2$—Br, in which $R^1$ is $C_6$-$C_{18}$ alkyl and $R^2$ is $C_6$-$C_{18}$ alkyl;

2) forming a compound 2 with a constructional formula

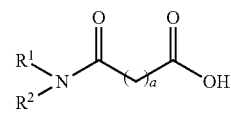

by reacting the compound 1 with succinic anhydride or glutaric anhydride through nucleophilic reaction, wherein a is 2 or 3;

then forming a compound 3 with a constructional formula

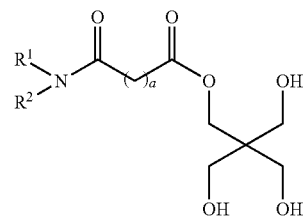

by reacting the compound 2 with excess 4 to 6 times of pentaerythritol through esterification reaction, wherein a is 2 or 3;

3) forming a hybrid lipid compound with a constructional formula

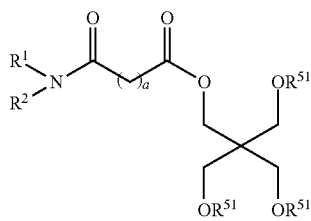

by reacting the compound 3 with 3-isocyanatopropyltriethoxysilane or 3-isocyanatopropyltrimethoxysilane through nucleophilic reaction, wherein $R^{51}$ is —CONH$(CH_2)_3Si(X)_3$, in which X is ethoxy or methoxy;

or forming a hybrid lipid with a constructional formula

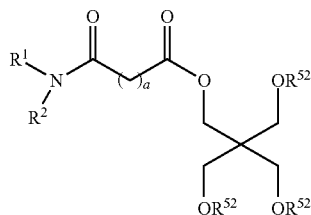

by reacting the compound 3 with 6-Bromohexanoyl chloride through esterification reaction, following reacting with dimethylamine gas saturated tetrahydrofuran solution through nucleophilic reaction, and then reacting with 3-Bromopropyltriethoxysilane or 3-Bromopropyltrimethoxysilane through nucleophilic reaction, wherein $R^{52}$ is —CO$(CH_2)_5$N$(CH_3)_2(CH_2)_3$Si$(X)_3$Y, in which X is ethoxy or methoxy and Y is halogenated group;

or forming a hybrid lipid compound with a constructional formula

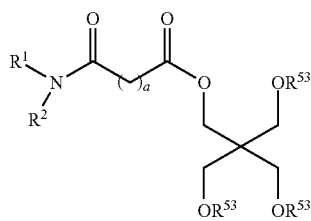

by reacting the compound 3 with succinic anhydride or glutaric anhydride through nucleophilic reaction, following reacting with 3-aminopropyltriethoxysilane or 3-aminopropyltrimethoxysilane through condensation reaction, and then dehydrating, wherein $R^{53}$ is —CO$(CH_2)_2$CONH$(CH_2)_3$Si$(X)_3$ or —CO$(CH_2)_3$CONH$(CH_2)_3$Si$(X)_3$, in which X is ethoxy or methoxy.

10. A method for making the hybrid lipid compound of claim 2 comprises following steps:

1) forming a compound 2 with a constructional formula

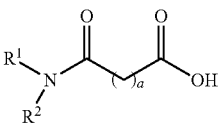

by reacting a compound 1 with a constructional formula

with a compound 4 with a constructional formula

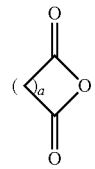

in polar organic solvent under 25-70° C. for 24-48 h, following washing in turn with acidic water and water, then recrystallizing, wherein the molar ratio of the compound 1 to the compound 4 is 1:1.5-4, a is 2 or 3, $R^1$ is $C_6$-$C_{18}$ alkyl and $R^2$ is $C_6$-$C_{18}$ alkyl;

2) forming a compound 6 with a constructional formula

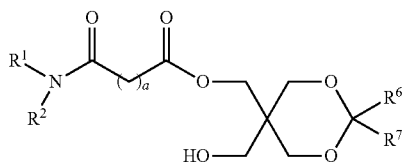

by reacting the compound 2 with N,N'-dicyclohexylcarbodiimide, 4-dimethylaminopyridine and a compound 5 with a constructional formula

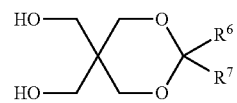

in polar organic solvent under 50-80° C. for 12-36 h, wherein the molar ratio between the compound 2, N,N'-dicyclohexylcarbodiimide, 4-dimethylaminopyridine and the compound 5 is 1:1-3:0.8-1.2:3-6, $R^6$ is —H, phenyl or —$CH_3$ and $R^7$ is —H, phenyl or —$CH_3$;

3) forming a compound 7 with a constructional formula

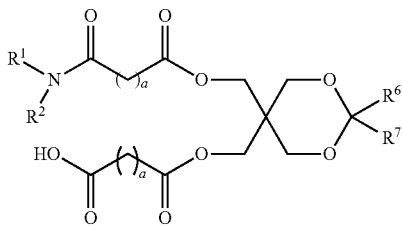

by reacting the compound 6 with 4-dimethylaminopyridine, deacid reagent and the compound 4 in aprotic organic solvent under 25-70° C. for 24-48 h, following washing in turn with acidic water and water, and then purifying through column chromatography, wherein the molar ratio between the compound 6,4-dimethylaminopyridine, the deacid reagent and the compound 4 is 1:0.4-1:1-6:2-5, and a is 2 or 3;

4) forming a compound 8 with a constructional formula

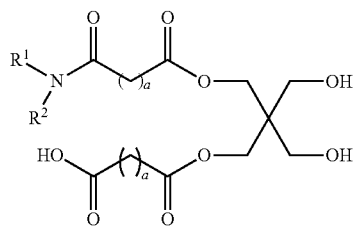

by reacting the compound 7 with hydrogen in the presence of catalyst in a mixed reaction solvent of tetrahydrofuran and methanol or ethanol under 25-80° C. for 12-48 h, wherein the molar ratio of the compound 7 to the catalyst is 1:0.4-0.6, hydrogen pressure is 1.0-1.2 MPa, the volume ratio of tetrahydrofuran to methanol or ethanol is 3-4:1, the catalyst is palladium/carbon or palladium hydroxide/carbon;

5) forming a compound 10 with a constructional formula

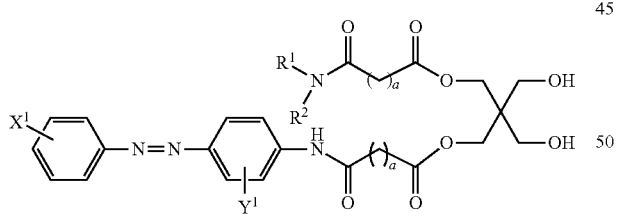

by reacting a compound 9 with a constructional formula

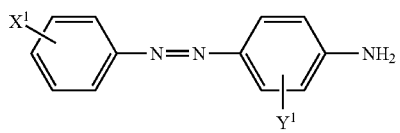

with the compound 8 and N,N'-dicyclohexylcarbodiimide in aprotic organic solvent under 25-45° C. for 24-60 h, wherein $X^1$ is —H, —$CH_3$, $CH_3O$—, halogen or —$NO_2$, $Y^1$ is —H, —$CH_3$, $CH_3O$— or halogen, and the molar ratio between the compound 8, N,N'-dicyclohexylcarbodiimide and the compound 9 is 1:1.2-1.5:1.1-2;

6) forming a hybrid lipid compound with a constructional formula

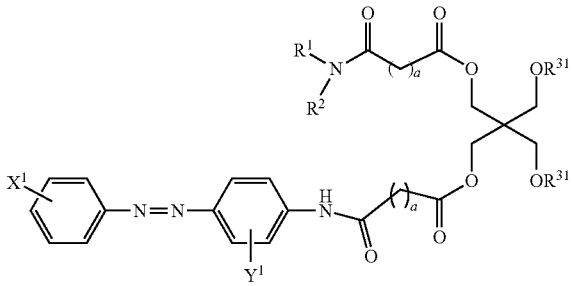

by reacting a compound 11 with a constructional formula

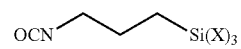

with the compound 10 and dibutyltin dilaurate in aprotic organic solvent under 40-70° C. for 48-72 h, wherein the molar ratio between the compound 10, the compound 11 and dibutyltin dilaurate is 1:2-4:0.2-0.8, $R^{31}$ is —CONH($CH_2$)$_3$Si(X)$_3$, in which X is ethoxy or methoxy;

or forming a compound 12 with a constructional formula

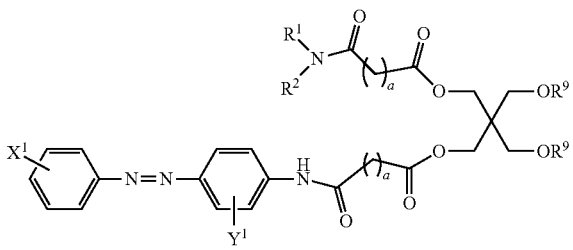

by reacting the compound 10 with 4-dimethylaminopyridine, deacid reagent and the compound 4 in aprotic organic solvent under 25-70° C. for 24-48 h, following washing in turn with acidic water and water, then purifying through column chromatography, wherein $R^9$ is —CO($CH_2$)$_2$COOH or —CO($CH_2$)$_3$COOH, the molar ratio between the compound 10, 4-dimethylaminopyridine, the deacid reagent and the compound 4 is 1:0.8-2:3-8:4-8;

finally, forming a hybrid lipid with a constructional formula

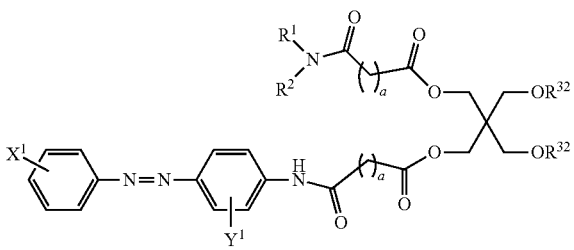

by reacting a compound 13 with a constructional formula

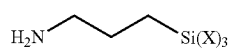

with the compound 12 and N,N'-dicyclohexylcarbodiimide in aprotic organic solvent under 25-40° C. for 24-36 h, wherein $R^{32}$ is —CO(CH$_2$)$_2$CONH(CH$_2$)$_3$Si(X)$_3$ or —CO(CH$_2$)$_3$CONH(CH$_2$)$_3$Si(X)$_3$, in which X is ethoxy or methoxy, and the molar ratio between the compound 12, N,N'-dicyclohexylcarbodiimide and the compound 13 is 1:1-2:1.5-2.0.

11. A method for making the hybrid lipid compound of claim 4 comprises following steps:
1) forming a compound 15 with a constructional formula

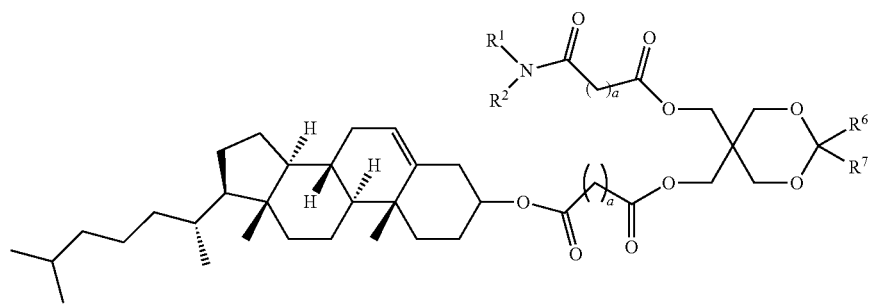

by reacting a compound 14 a constructional formula

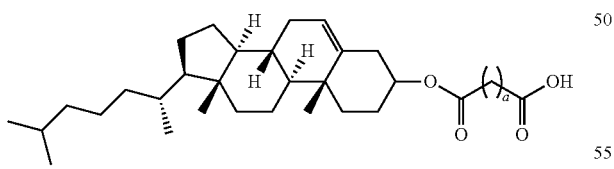

with the compound 6, N,N'-dicyclohexylcarbodiimide and 4-dimethylaminopyridine in polar organic solvent under 50-80° C. for 12-36 h, wherein the molar ratio between the compound 6, N,N'-dicyclohexylcarbodiimide, 4-dimethylaminopyridine and the compound 14 is 1:1-3:0.8-1.2:1-3, a is 2 or 3, $R^1$ is $C_6$-$C_{18}$ alkyl, $R^2$ is $C_6$-$C_{18}$ alkyl, $R^6$ is phenyl or —CH$_3$ and $R^7$ is —H or —CH$_3$;

2) forming a compound 16 with a constructional formula

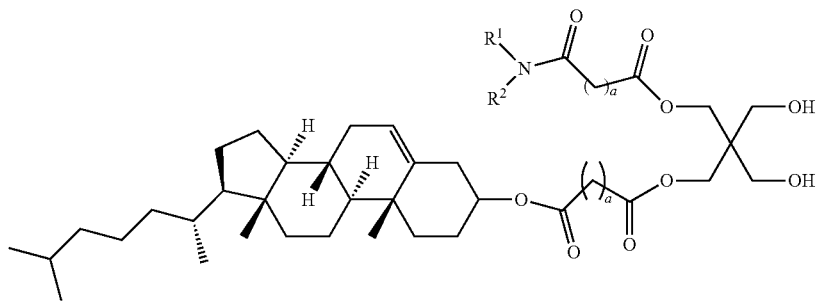

by reacting the compound 15 with hydrogen in the presence of catalyst in a mixed reaction solvent of tetrahydrofuran and methanol or ethanol under 25-80° C. for 12-48 h, wherein the molar ratio of the compound 15 to catalyst is 1:0.4-0.6, hydrogen pressure is 1.0-1.2 MPa, the volume ratio of tetrahydrofuran to methanol or ethanol is 3-4:1, the catalyst is palladium/carbon or palladium hydroxide/carbon;

3) forming a hybrid lipid compound with a constructional formula

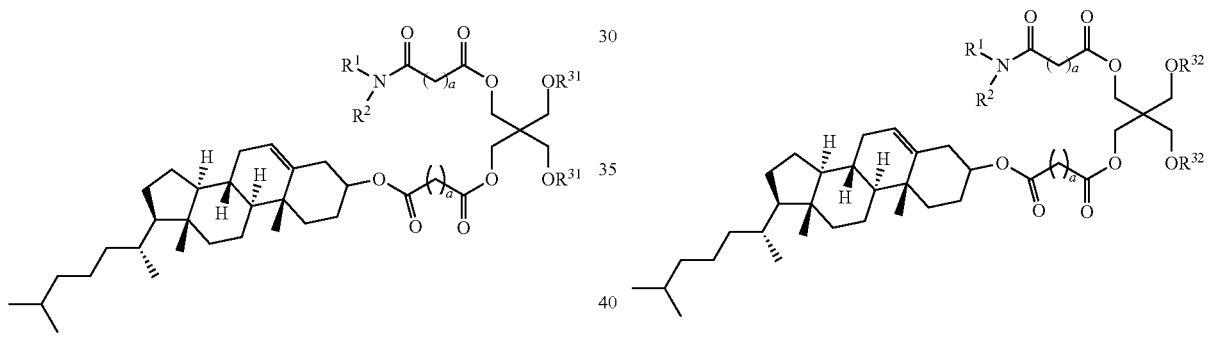

by reacting the compound 16 with the compound 11 and dibutyltin dilaurate in aprotic organic solvent under 40-70° C. for 48-72 h, wherein $R^{31}$ is —CONH$(CH_2)_3Si(X)_3$, in which X is ethoxy or methoxy, the molar ratio between the compound 16, the compound 11 and dibutyltin dilaurate is 1:2-4:0.2-0.8;

4) forming a compound 17 with a constructional formula

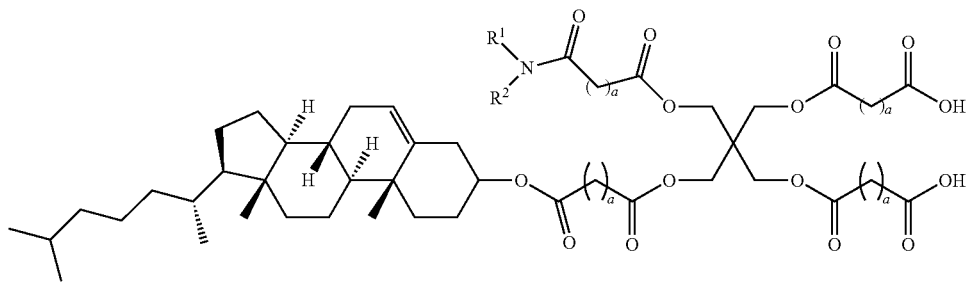

by reacting the compound 16 with 4-dimethylaminopyridine, deacid reagent and the compound 4 in aprotic organic solvent under 25-70° C. for 24-48 h, following washing in turn with acidic water and water, then purifying through column chromatography, wherein the molar ratio between the compound 16, 4-dimethylaminopyridine, the deacid reagent and the compound 4 is 1:0.8-2:3-8:4-8, and a is 2 or 3;

5) forming a hybrid lipid compound with a constructional formula by reacting the compound 17 with the compound 13 and N,N'-dicyclohexylcarbodiimide in aprotic organic solvent under 25-40° C. for 24-36 h, wherein $R^{32}$ is —CO$(CH_2)_2CONH(CH_2)_3Si(X)_3$ or —CO$(CH_2)_3CONH(CH_2)_3Si(X)_3$, in which X is ethoxy or methoxy, and the molar ratio between the compound 17, N,N'-dicyclohexylcarbodiimide and the compound 13 is 1:1-2:2.0-2.5.

12. A method for making the hybrid lipid compound of claim 5 comprises following steps:

1) forming a compound 19 with a constructional formula

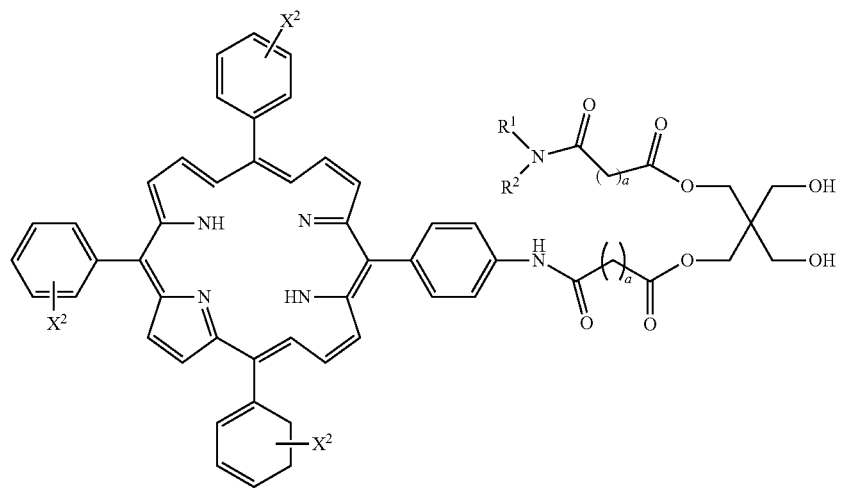

by reacting the compound 18 with a constructional formula

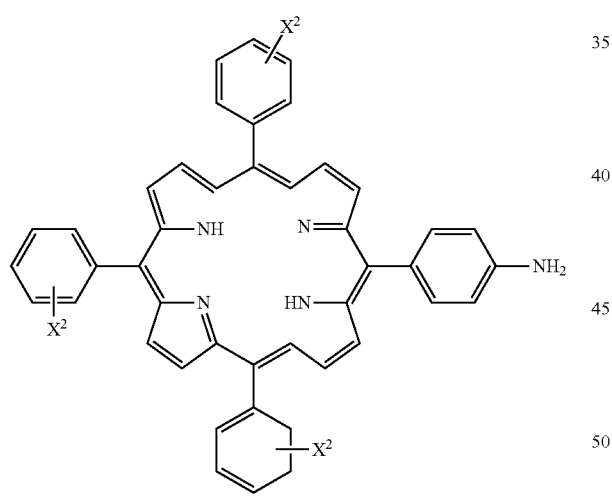

with the compound 8 and N,N'-dicyclohexylcarbodiimide in aprotic organic solvent under 25-45° C. for 24-72 h, wherein the molar ratio between the compound 8, N,N'-dicyclohexylcarbodiimide and the compound 18 is 1:1.2-1.5:1.1-2, a is 2 or 3, $X^2$ is —H, —$CH_3$, $CH_3O$— or halogen, $R^1$ is $C_6$-$C_{18}$ alkyl, and $R^2$ is $C_6$-$C_{18}$ alkyl;

2) forming a hybrid lipid compound 20 with a constructional formula

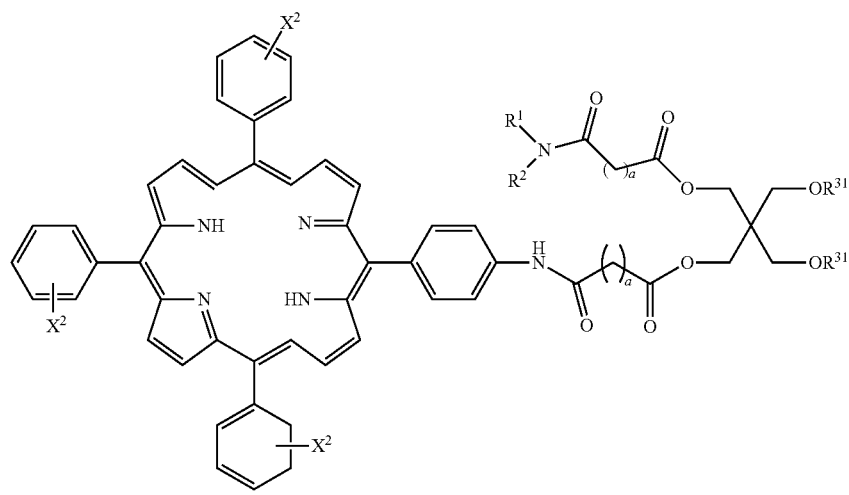

by reacting the compound 11 with the compound 19 and dibutyltin dilaurate in aprotic organic solvent under 40-80° C. for 36-72 h, wherein $R^{31}$ is —CONH$(CH_2)_3Si(X)_3$, in which X is ethoxy or methoxy, the molar ratio between the compound 19, the compound 11 and dibutyltin dilaurate is 1:2-5:0.2-1.0;

3) forming a compound 21 with a constructional formula

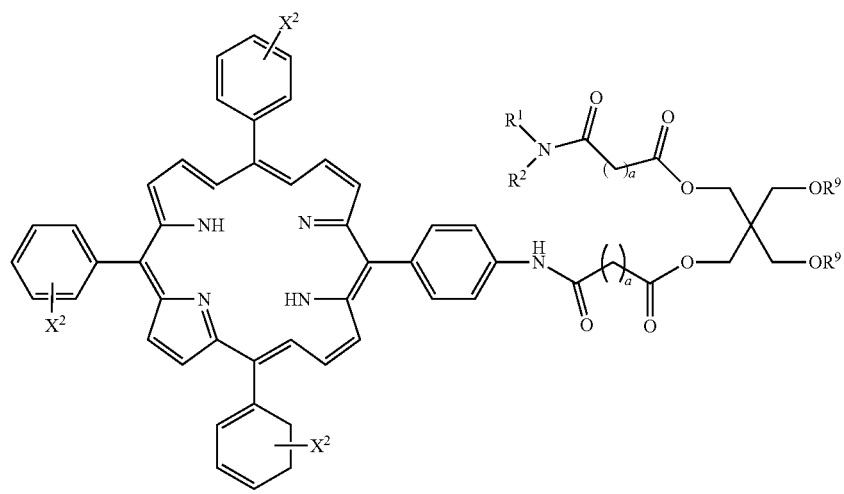

by reacting the compound 19 with 4-dimethylaminopyridine, deacid reagent and the compound 4 in aprotic organic solvent under 25-70° C. for 48-48 h, following washing in turn with acidic water and water, then purifying through column chromatography, wherein $R^9$ is —CO(CH$_2$)$_2$COOH or —CO(CH$_2$)$_3$COOH, the molar ratio between the compound 19, 4-dimethylaminopyridine, the deacid reagent and the compound 4 is 1:0.8-2:3-9:3-10, the deacid agent is triethylamine or pyridine;

4) forming a hybrid lipid compound 22 with a constructional formula

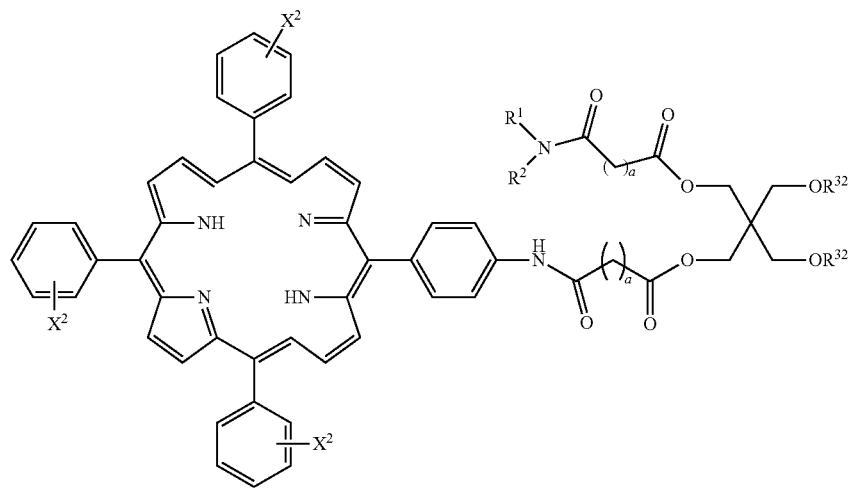

by reacting the compound 21 with the compound 13 and N,N'-dicyclohexylcarbodiimide in aprotic organic solvent under 25-45° C. for 24-48 h, wherein $R^{32}$ is —CO$(CH_2)_2$CONH$(CH_2)_3$Si$(X)_3$ or —CO$(CH_2)_3$CONH$(CH_2)_3$Si$(X)_3$, in which X is ethoxy or methoxy, and the molar ratio between the compound 21, N,N'-dicyclohexylcarbodiimide and the compound 13 is 1:1-2:1.5-2.0;

5) forming a hybrid lipid compound with a constructional formula

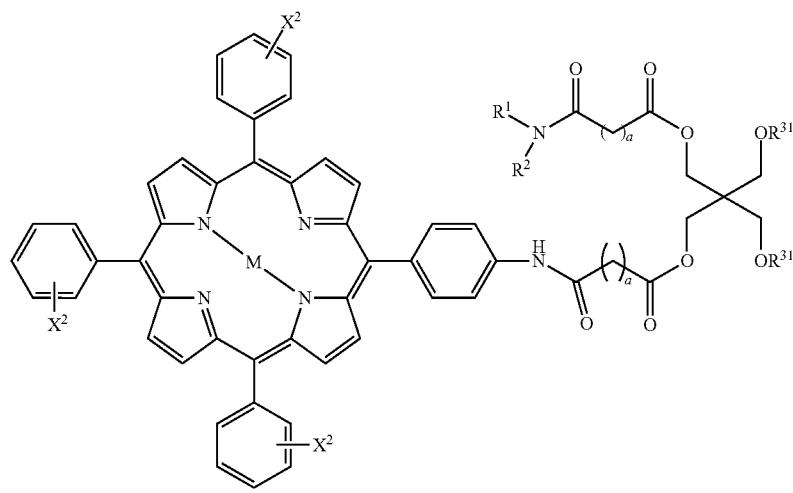

by reacting a Metal salts 23 with a constructional formula MY with the compound 20 in organic solvent under 25-180° C. for 2-48 h, following removing reaction solvent in vacuum, later washing, the crude product was then purified by column chromatography, wherein the molar ratio the compound 20 and the compound 23 is 1:5-25, $R^{31}$ is —CONH$(CH_2)_3$Si$(X)_3$, in which X is ethoxy or methoxy;

or forming a hybrid lipid compound with a constructional formula

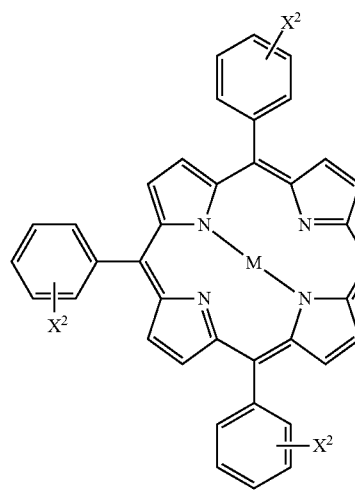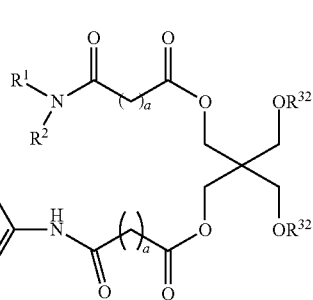

by reacting a Metal salts 23 a constructional formula MY with the compound 22 under 25-180° C. for 2-48 h, following removing reaction solvent in vacuum, later washing, the crude product was then purified by column chromatography, wherein the molar ratio of the compound 22 and the compound 23 is 1:5-25, $R^{32}$ is —CO$(CH_2)_2$CONH$(CH_2)_3$Si$(X)_3$ or —CO$(CH_2)_3$CONH$(CH_2)_3$Si$(X)_3$, in which X is ethoxy or methoxy; $X^2$ is —H, —$CH_3$, $CH_3$O— or halogen, M is the metal ion coordinated with porphyrin ring, and Y is the anion which formed metal salts with M.

13. A method for making the hybrid lipid compound of claim 6 comprises following steps:
1) forming a compound 2 with a constructional formula

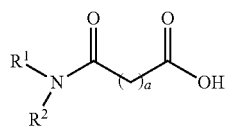

by reacting a compound 1 with a constructional formula

with a compound 4 a constructional formula

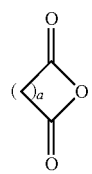

in polar organic solvent under 25-70° C. for 24-48 h, following washing in turn with acidic water and water, then recrystallizing, wherein the molar ratio of the compound 1 to the compound 4 is 1:1.5-4, a is 2 or 3, $R^1$ is $C_6$-$C_{18}$ alkyl, and $R^2$ is $C_6$-$C_{18}$ alkyl;

2) forming a compound 25 with a constructional formula

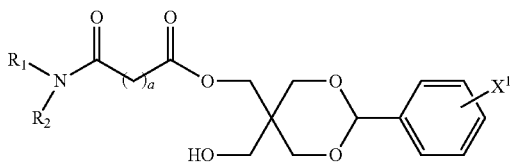

by reacting a compound 24 with a constructional formula

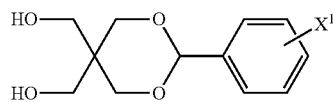

with the compound 2, N,N'-dicyclohexylcarbodiimide and 4-dimethylaminopyridine in polar organic solvent under 50-80° C. for 12-36 h, wherein X1 is —H, —$CH_3$, $CH_3$O—, halogen or —$NO_2$, the molar ratio between the compound 2, N,N'-dicyclohexylcarbodiimide, 4-dimethylaminopyridine and the compound 24 is 1:1-3:0.8-1.2:3-6;
3) forming a hybrid lipid compound with a constructional formula

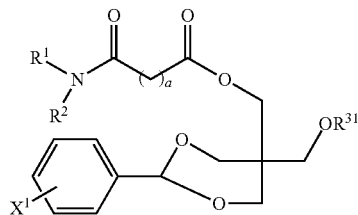

by reacting the compound 25, the compound 11 and dibutyltin dilaurate in aprotic organic solvent under 40-70° C. for 48-72 h, wherein $R^{31}$ is —CONH$(CH_2)_3$Si$(X)_3$, in which X is ethoxy or methoxy, and the molar ratio between the compound 25, the compound 11 and dibutyltin dilaurate is 1:1-2:0.2-0.8;

4) forming a compound 26 with a constructional formula

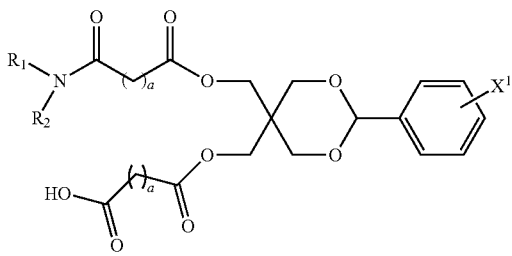

by reacting the compound 25 with 4-dimethylaminopyridine, deacid reagent and the compound 4 in aprotic organic solvent under 25-70° C. for 24-48 h, following washing in turn with acidic water and water, then recrystallizing, wherein the molar ratio between the compound 25, 4-dimethylaminopyridine, the deacid agent and the compound 4 is 1:0.4-1:1-6:2-5;

5) forming a hybrid lipid compound with a constructional formula

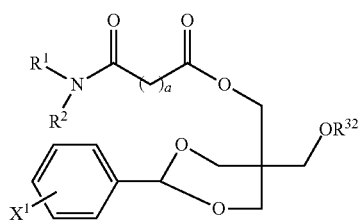

by reacting the compound 26 with the compound 13 and N,N'-dicyclohexylcarbodiimide in aprotic organic solvent, under 25-40° C. for 24-36 h, wherein $R^{32}$ is —CO(CH$_2$)$_2$CONH(CH$_2$)$_3$Si(X)$_3$ or —CO(CH$_2$)$_3$CONH(CH$_2$)$_3$Si(X)$_3$, in which X is ethoxy or methoxy; and the molar ratio between the compound 26, N,N'-dicyclohexylcarbodiimide and the compound 13 is 1:1-2:1.1-1.5.

14. A method for making the hybrid lipid compound of claim 7 comprises following steps:

1) forming a compound 27 with a constructional formula

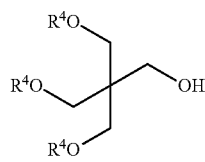

by reacting pentaerythritol and alkyl bromide with a constructional formula of $R^4$—Br in alkaline condition through nucleophilic substitution reaction, wherein the molar ratio of pentaerythritol to alkyl bromide is 1:3, and $R^4$ is $C_6$-$C_{18}$ alkyl;

2) forming a hybrid lipid compound with a constructional formula

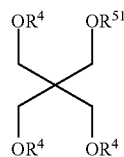

by reacting the compound 27 with 3-isocyanatopropyltriethoxysilane or 3-isocyanatopropyltrimethoxysilane through nucleophilic reactions, wherein $R^{51}$ is —CONH(CH$_2$)$_3$Si(X)$_3$, in which X is ethoxy or methoxy;

or forming a hybrid lipid compound with a constructional formula

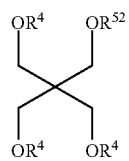

by reacting the compound 27 with 6-Bromohexanoyl chloride through esterification reaction, following reacting with dimethylamine gas saturated tetrahydrofuran solution through nucleophilic reaction, and then reacting with 3-Bromopropyltriethoxysilane or 3-Bromopropyltrimethoxysilane through nucleophilic reaction, wherein $R^{52}$ is —CO(CH$_2$)$_5$N(CH$_3$)$_2$(CH$_2$)$_3$Si(X)$_3$Y, in which X is ethoxy or methoxy and Y is halogenated group;

or forming a hybrid lipid compound with a constructional formula

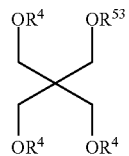

by reacting the compound 27 with succinic anhydride or glutaric anhydride through nucleophilic reaction, following reacting with 3-aminopropyltriethoxysilane or 3-aminopropyltrimethoxysilane through nucleophilic reaction, wherein $R^{53}$ is —CO(CH$_2$)$_2$CONH(CH$_2$)$_3$Si(X)$_3$ or —CO(CH$_2$)$_3$CONH(CH$_2$)$_3$Si(X)$_3$, in which X is ethoxy or methoxy.

15. A method for making the hybrid lipid compound of claim 8 comprises following steps:

1) forming a compound 8 with a constructional formula

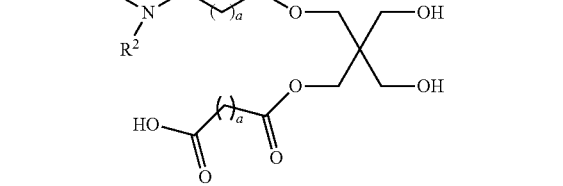

by reacting the compound 26 with hydrogen in the presence of catalyst in a mixed reaction solvent of tetrahydrofuran and methanol or ethanol under 25-80° C. for 12-48 h, wherein the molar ratio of the compound 26 to the catalyst is 1:0.4-0.6, hydrogen pressure is 1.0-1.2 MPa, the volume ratio of tetrahydrofuran to methanol or ethanol is 3-4:1, the catalyst is palladium/carbon or palladium hydroxide/carbon, a is 2 or 3, $R^1$ is $C_6$-$C_{18}$ alkyl, and $R^2$ is $C_6$-$C_{18}$ alkyl;

2) forming a hybrid lipid compound 28 with a constructional formula

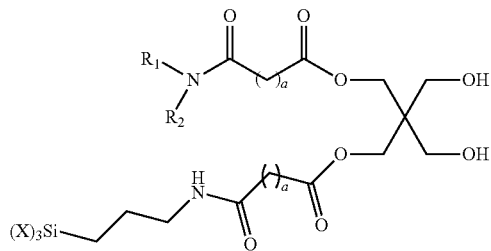

by reacting the compound 13 with a constructional formula

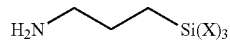

with the compound 8 and N,N-dicyclohexylcarbodiimide in aprotic organic solvent under 25-40° C. for 24-36 h, wherein the molar ratio between the compound 8, N,N'-dicyclohexylcarbodiimide and the compound 13 is 1:1-2:1.1-1.5, and X is ethoxy or methoxy;

3) forming a hybrid lipid compound with a constructional formula

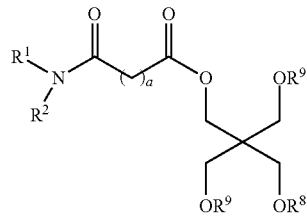

by reacting the compound 28 with deacid reagent, 4-dimethylaminopyridine and the compound 4 in aprotic organic solvent under 25-70° C. for 24-48 h, following washing in turn with acidic water and water, then purifying through column chromatography, wherein $R^9$ is —CO(CH$_2$)$_2$COOH or —CO(CH$_2$)$_3$COOH, $R^8$ is —CO(CH$_2$)$_2$CONH(CH$_2$)$_3$Si(X)$_3$ or —CO(CH$_2$)$_3$CONH(CH$_2$)$_3$Si(X)$_3$, in which X is ethoxy or methoxy, a is 2 or 3, and the molar ratio of compound 28, 4-dimethylaminopyridine, the deacid reagent and the compound 4 is 1:0.4-1:1-6:4-8.

* * * * *